(12) United States Patent
Herrmann et al.

(10) Patent No.: US 11,751,832 B2
(45) Date of Patent: Sep. 12, 2023

(54) CTA LARGE VESSEL OCCLUSION MODEL

(71) Applicants: GE Precision Healthcare LLC, Waukesha, WI (US); Partners Healthcare System, Inc., Boston, MA (US); The General Hospital Corporation, Boston, MA (US); The Brigham and Women's Hospital, Inc., Boston, MA (US)

(72) Inventors: Markus Daniel Herrmann, Boston, MA (US); John Francis Kalafut, Pittsburgh, PA (US); Bernardo Canedo Bizzo, Boston, MA (US); Christopher P. Bridge, Cambridge, MA (US); Michael Lev, Newton, MA (US); Charles J. Lu, Cambridge, MA (US); James Hillis, Cambridge, MA (US)

(73) Assignees: GE Precision Healthcare LLC, Waukesha, WI (US); Partners HealthCare System, Inc., Boston, MA (US); The General Hospital Corporation, Boston, MA (US); The Brigham and Women's Hospital, Inc., Boston, MA (US)

( * ) Notice: Subject to any disclaimer, the term of this patent is extended or adjusted under 35 U.S.C. 154(b) by 323 days.

(21) Appl. No.: 17/083,761

(22) Filed: Oct. 29, 2020

(65) Prior Publication Data

US 2021/0236080 A1 Aug. 5, 2021

Related U.S. Application Data

(60) Provisional application No. 63/086,368, filed on Oct. 1, 2020, provisional application No. 62/967,849, filed on Jan. 30, 2020.

(51) Int. Cl.
  *A61B 6/00* (2006.01)
  *A61B 6/03* (2006.01)
  (Continued)

(52) U.S. Cl.
  CPC .............. *A61B 6/507* (2013.01); *A61B 6/032* (2013.01); *A61B 6/501* (2013.01); *A61B 6/504* (2013.01);
  (Continued)

(58) Field of Classification Search
  CPC ......... A61B 6/032; A61B 6/507; A61B 6/501; A61B 6/504; A61B 6/5217;
  (Continued)

(56) References Cited

PUBLICATIONS

Sheth et al. 2019 Stroke 50 3093-3100; with supplemental material (Year: 2019).*

(Continued)

*Primary Examiner* — Keith M Raymond
*Assistant Examiner* — Patrick M Mehl
(74) *Attorney, Agent, or Firm* — Amin, Turocy & Watson, LLP

(57) ABSTRACT

Systems and techniques that facilitate automated localization of large vessel occlusions are provided. In various embodiments, an input component can receive computed tomography angiogram (CTA) images of a patient's brain. In various embodiments, a localization component can determine, via a machine learning algorithm, a location of a large vessel occlusion (LVO) in the patient's brain based on the CTA images. In various instances, the location of the LVO can comprise a laterality and an occlusion site. In various aspects, the laterality can indicate a right side or a left side of the patient's brain, and the occlusion site can indicate an internal carotid artery (ICA), an M1 segment of a middle cerebral artery (MCA) or an M2 segment of an MCA. In various cases, a visualization component can generate and (Continued)

display to a user a three-dimensional maximum intensity projection (MIP) reconstruction of the patient's brain based on the CTA images to facilitate visual verification of the LVO by the user.

20 Claims, 32 Drawing Sheets

(51) Int. Cl.
    *G06T 7/70*     (2017.01)
    *G06N 20/20*     (2019.01)
    *G16H 30/20*     (2018.01)

(52) U.S. Cl.
    CPC ........... *A61B 6/5217* (2013.01); *G06N 20/20* (2019.01); *G06T 7/70* (2017.01); *G16H 30/20* (2018.01); *G06T 2207/10081* (2013.01); *G06T 2207/20081* (2013.01); *G06T 2207/20084* (2013.01); *G06T 2207/20132* (2013.01); *G06T 2207/30101* (2013.01)

(58) Field of Classification Search
    CPC . G06T 2207/20081; G06T 2207/30101; G06T 2207/10081; G06T 2207/20084; G06T 7/70; G06T 2207/20132; G06N 20/20; G16H 30/20
    See application file for complete search history.

(56) References Cited

PUBLICATIONS

Amukotuwa et al. 2019 Stroke 50:3431-3438; with supplement material (Year: 2019).*
You et al. 2019 arxiv.1905.09049 7pages; internet access https://doi.org/10.48550/arxiv.1905.09049 (Year: 2019).*
Robben et al. 2020 Med. Imag. Analysis 59:101589 9 pages; ePub Oct. 15, 2019 (Year: 2019).*
Vargas et al. 2019 World Neurosurgery 124:e10-e16 (Year: 2019).*
Pathak et al. 2018 in Progress in Computing, Analytics and Networking, Advances in Intelligent Systems and Computing 710 p. 491-499 (Year: 2018).*
"Viz LVO," Viz AI, https://www.viz.ai/ischemic-stroke, last accessed on Oct. 29, 2020, 9 pages.
"Rapid CTA," iSchemaView, https://www.rapidai.com/rapid-cta, last accessed on Oct. 29, 2020, 7 pages.
"e-CTA" Brainomix, https://www.brainomix.com/e-cta/, last accessed on Oct. 29, 2020, 4 pages.
"Aidoc LVO module," Aidoc, https://www.aidoc.com/blog/stroke-ai-package/, last accessed on Oct. 29, 2020, 3 pages.

* cited by examiner

FIG. 7B

CTA LARGE VESSEL OCCLUSION MODEL

CROSS-REFERENCE TO RELATED APPLICATIONS

This application claims priority to U.S. Provisional Patent Application Ser. No. 62/967,849 filed on Jan. 30, 2020, entitled "CTA LARGE VESSEL OCCLUSION MODEL," and U.S. Provisional Patent Application Ser. No. 63/086,368 filed on Oct. 10, 2020, entitled "CTA LARGE VESSEL OCCLUSION MODEL." The entirety of the aforementioned applications are incorporated by reference herein.

BACKGROUND

The subject disclosure relates generally to detection of large vessel occlusions, and more specifically to automated localization of large vessel occlusions in patients' brains based on computed tomography angiograms.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate automated localization of large vessel occlusions are described.

According to one or more embodiments, a system is provided. The system can comprise a memory that can store computer-executable components. The system can further comprise a processor that can be operably coupled to the memory and that can execute the computer-executable components stored in the memory. In various embodiments, the computer-executable components can comprise an input component that can receive computed tomography angiogram (CTA) images of a patient's brain. In various aspects, the computer-executable components can further comprise a localization component that can determine, via a machine learning algorithm, a location of a large vessel occlusion (LVO) in the patient's brain based on the CTA images. In various instances, the location of the LVO can comprise a laterality and an occlusion site. In various cases, the laterality can indicate a right side or a left side of the patient's brain, and the occlusion site can indicate an internal carotid artery (ICA), an M1 segment of a middle cerebral artery (MCA), or an M2 segment of an MCA. In various embodiments, the computer-executable components can further comprise a visualization component that can generate and display to a user a three-dimensional maximum intensity projection (MIP) reconstruction of the patient's brain based on the CTA images to facilitate visual verification of the LVO by the user. In various aspects, the visualization component can highlight the LVO in the three-dimensional MIP reconstruction.

According to one or more embodiments, the above-described system can be implemented as a computer-implemented method.

According to one or more embodiments, the above-described system can be implemented as a computer program product for facilitating automated localization of LVOs, the computer program product comprising a computer readable memory having program instructions embodied therewith, the program instructions executable by a processing component to cause the processing component to perform various acts.

DESCRIPTION OF THE DRAWINGS

FIGS. 7A-7B illustrate exemplary, non-limiting experimentation results of a multi-classification model that facilitates automated localization of large vessel occlusions in accordance with one or more embodiments described herein.

DETAILED DESCRIPTION

Figure 1A:
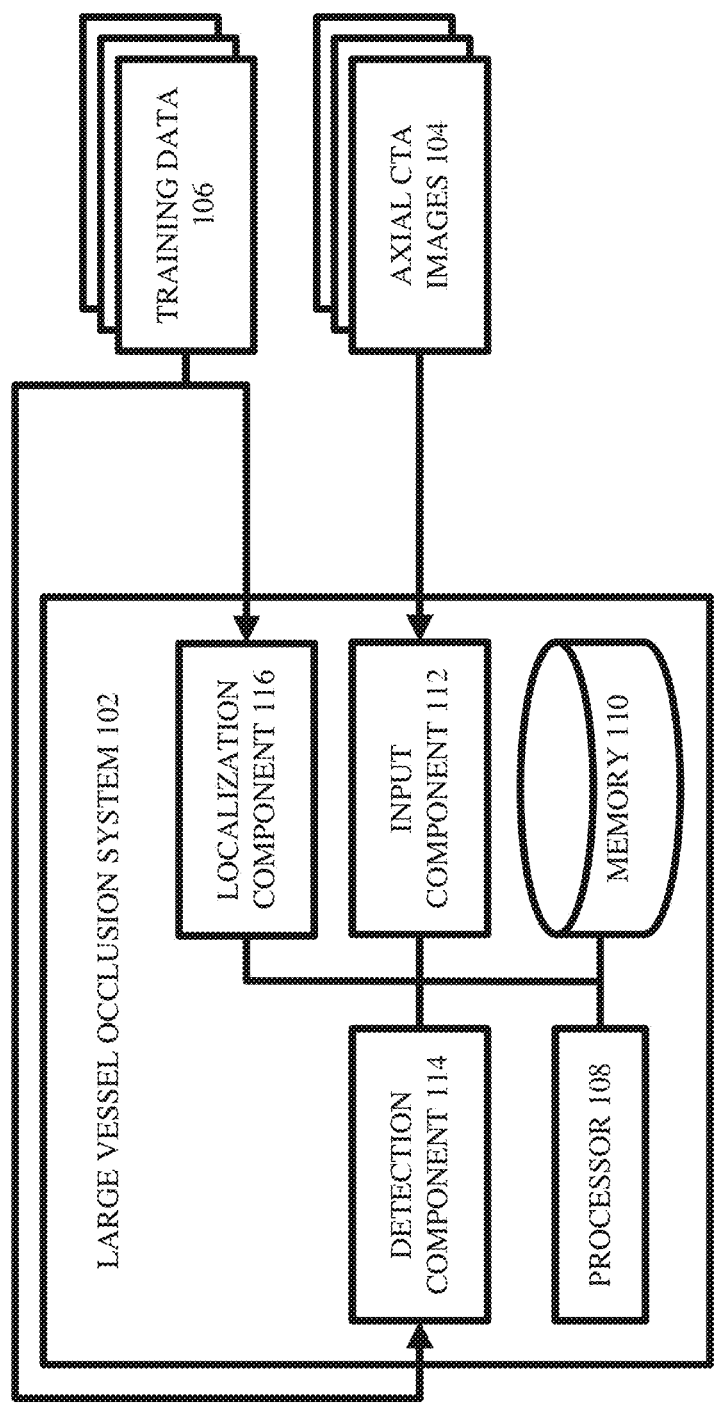
FIGS. 1A-1B illustrate a block diagram of an example, non-limiting system that facilitates automated localization of large vessel occlusions in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Stroke is a medical condition in which brain cells die and/or are damaged due to insufficient blood supply. There are two primary types of stroke: ischemic stroke, where the insufficient blood supply is caused by lack of blood flow in the brain due to arterial occlusions/blockages, and hemorrhagic stroke, where the insufficient blood supply is caused by bleeding in the brain. In the case of ischemic stroke, knowing the presence and/or location of intracranial large vessel occlusions (LVO), as well as the status (e.g., robust vs. malignant) of the collateral circulation, can be critical for properly performing patient triage and making appropriate endovascular treatment decisions. Indeed, time can be of the essence when dealing with ischemic stroke victims, and endovascular therapy can generally be performed only at large, fully-equipped stroke centers rather than smaller, less specialized medical centers. Moreover, different types of LVOs can require different types of treatment, and so on. Thus, being able to quickly, efficiently, and accurately detect and/or localize LVOs in a patient's brain is advantageous (e.g., rapidly detecting and localizing LVOs in small medical centers allows sooner transportation to large stroke centers and thus sooner treatment).

Head computed tomography angiography (CTA) is generally the modality of choice for detecting and localizing LVOs. CTA is a computed tomography technique that utilizes injected contrast agents to visualize arterial and/or venous vessels throughout the body in order to search for occlusions (e.g., full and/or partial blockages and/or constrictions of blood vessels, and so on). In the case of ischemic stroke, a series of axial CTA images of a patient's brain can be generated and examined for LVOs by an attending medical professional (e.g., physician, nurse, and so on). However, manual examination of CTA images can be time-consuming, inefficient, inconsistent, and/or inaccurate (e.g., human physicians and nurses can perform suboptimal manual examinations when under time pressure, when overworked and/or overwhelmed, due to mere human error, and so on). Thus, systems/techniques for automatically analyzing CTA images are advantageous.

Although some systems/techniques exist for automatically detecting the presence of LVOs in patients' brains, such systems/techniques provide only a binary output (e.g., LVO detected or LVO not detected), rather than more granularly identifying a specific type and/or location of LVO (e.g., LVO detected in M2 segment of right MCA, and so on). Since different types/locations of LVOs can require different treatment protocols, systems/techniques that can automatically determine where a detected LVO is in the patient's brain can significantly save time, improve patient triage, and/or expedite treatment decision-making by attending medical professionals. Moreover, existing systems/techniques generally do not provide automated maximum intensity projection (MIP) reconstructions (e.g., three-dimensional visualization volumes of the vascular tree of the patient's brain) that can be used by attending medical professionals to visually verify the LVO localization and/or to visually check the status of collateral circulation. Indeed, since attending medical professionals can, at times, wish to visually verify for themselves LVO localization results, systems/techniques that facilitate automated LVO localization and that also automatically generate and display MIP reconstructions that highlight, mark, and/or otherwise visually emphasize the localized LVOs are advantageous.

Various embodiments of the subject innovation can address these issues in the prior art. One or more embodiments described herein include systems, computer-implemented methods, apparatus, and/or computer-program products that can facilitate automated localization of large vessel occlusions (LVOs). In various instances, the subject innovation can receive (e.g., via electronic and/or digital communication) a series of axial CTA images of a patient's brain. In various aspects, the subject innovation can determine (e.g., can localize) a location of a large vessel occlusion in the patient's brain based on the CTA images. In various instances, the location of the LVO can comprise a laterality (e.g., right half of patient's brain, left half of patient's brain, and so on) and an occlusion site (e.g., an internal carotid artery (ICA) of the patient's brain, an M1 segment of a middle cerebral artery (MCA) of the patient's brain, an M2 segment of an MCA of the patient's brain, a posterior cerebral artery (PCA) of the patient's brain, any other identifiable and/or desired segment in the vascular tree of the patient's brain, and so on).

Specifically, the subject innovation can, in various embodiments, employ a trained convolutional neural network having residual bottleneck blocks (e.g., ResNet) and/or having dense blocks (e.g., DenseNet) to facilitate such localization. In various cases, the trained convolutional neural network can receive as input the series of CTA images of the patient's brain (e.g., a series of two-dimensional pixel matrices representing the CTA images), and can produce as output a scalar value that indicates a localization and/or classification of a detected LVO (e.g., a first scalar value can indicate an LVO at a first location in the patient's brain, a second scalar value can indicate an LVO at a second location in the patient's brain, and so on). In various instances, the convolutional neural network can be trained to localize LVOs in n different locations in the patient's brain, where n can be any suitable and/or desired positive integer representing n desired locations of interest in the vascular tree of the brain. In such cases, the convolutional neural network can produce a single scalar output that can take on n+1 possible values (e.g., a unique value for each of the n different locations in the patient's brain, and one other value to indicate that no LVO is detected in the patient's brain). For example, in various embodiments, a scalar output value of 0 can indicate no LVO detected at all, a scalar output value of 1 can indicate an LVO in the right ICA, a scalar output value of 2 can indicate an LVO in the left ICA, a scalar output value of 3 can indicate an LVO in the right M1 segment of the MCA, a scalar output value of 4 can indicate an LVO in the right M2 segment of the MCA, a scalar output value of 5 can indicate an LVO in the left M1 segment of the MCA, and so on. In various aspects, the trained convolutional neural network can produce two scalar outputs rather than one scalar output (e.g., a first scalar output indicating laterality such as right or left; and a second scalar output indicating occlusion site such as ICA, M1 segment of MCA, M2 segment of MCA, PCA, and so on). In various instances, the trained convolutional neural network can produce three scalar outputs (e.g., a first scalar output indicating whether an LVO is detected at all, a second scalar output indicating laterality, and a third scalar output indicating occlusion site). In various embodiments, any suitable technique for numerically indicating and/or representing the location of a detected LVO can be implemented.

In some cases, the trained convolutional neural network can take as input a cropped unilateral region of a series of CTA images representing a right laterality and a left laterality of a patient's brain, and the trained convolutional neural network can generate as output two scalar values for each laterality. In various aspects, a first scalar value can denote a prediction/determination that an LVO is present or absent in the given laterality (e.g., the first scalar can represent a probability that the given laterality has an LVO), and a second scalar value can denote a prediction/determination of a subtype localization of the LVO (e.g., ICA, MCA-1, MCA-2). In various aspects, the second scalar value can be considered as relevant when the first scalar value indicates that an LVO is present in the given laterality, and the second scalar value can be considered as irrelevant when the first scalar value indicates that an LVO is not present in the given laterality. In various aspects, the trained convolutional neural network can be executed on each laterality (e.g., right, left) of each patient, and an overall prediction for each patient can be obtained by taking the maximal predicted scalar value from among all the scalar values generated for both the right and left literalities.

In various embodiments, the subject innovation can generate and display to a user (e.g., to an attending medical professional) a three-dimensional maximum intensity projection (MIP) reconstruction of the patient's brain, based on the CTA images, to facilitate visual verification of the LVO by the user. That is, various instances of the subject innovation can automatically localize (e.g., determine location of) an LVO in a patient's brain based on received CTA images of the patient's brain, and can also stitch together the received CTA images into a three-dimensional volume (e.g., the MIP reconstruction) which can visually represent the vascular tree of the patient's brain in three-space (e.g., in an x-y-z coordinate system). In various aspects, any suitable two-dimensional projection of the MIP reconstruction (e.g., of the three-dimensional volume) can be displayed to a user (e.g., attending medical professional). In some cases, the user can verify the localized LVO by manually checking any desired two-dimensional projections (e.g., slices) of the MIP reconstruction. For example, the user can, in some instances, check different projections (e.g., different two-dimensional slices) of the reconstructed volume in order to verify the localized LVO (e.g., the user can check an x-y projection of the volume, an x-z projection of the volume, a y-z projection of the volume, any other suitable two-dimensional projection of the volume as desired, and so on in order to get different views of the vascular tree and thus of the LVO). In some instances, the subject innovation can highlight the LVO in the MIP reconstruction in order to allow the user to more easily visually perceive the LVO. For instance, the subject innovation can, in various embodiments, mark the localized LVO in the MIP reconstruction (e.g., circle the localized LVO, point an arrow toward the localized LVO, place a star or asterisk by the localized LVO, and so on), change the color of voxels surrounding and/or representing the localized LVO (e.g., display the localized LVO in gradations of red, yellow, green, any other desired/suitable color, and so on), and/or otherwise visually emphasize the localized LVO so as to make visual acquisition of the localized LVO more easy for the user. By highlighting the localized LVO, the user can quickly spot the localized LVO (e.g., in order to verify whether the user agrees with the inference/determination of the subject innovation) and can avoid spending time considering/analyzing irrelevant portions of the vascular tree of the patient's brain. In various aspects, the user can use the three-dimensional MIP reconstruction in order to manually view and/or evaluate the status of collateral circulation in the patient's brain (e.g., robust collateral circulation vs. malignant collateral circulation, and so on), since treatment decisions can sometimes depend on collateral circulation status.

In some embodiments, the subject innovation can receive feedback from the user based on the user's consideration of the MIP reconstruction (e.g., the user can indicate agreement and/or disagreement with the localization/determination of the subject innovation). In some instances, the subject innovation can learn from the user's feedback (e.g., supervised training where the user's feedback identifies a correct label/classification/localization for the given input CTA images, such that the parameters, weights, and/or biases of the trained convolutional neural network are adjusted, such as through backpropagation, in view of the user's feedback).

Although the herein disclosure mainly discusses embodiments of the subject innovation as detecting/localizing LVOs in human brains, this is exemplary and non-limiting. In various aspects, embodiments of the subject innovation can be trained to detect/localize any other vascular occlusions in any suitable body part of interest (e.g., brain, lungs, kidneys, neck, heart) in any suitable patient (e.g., human or animal).

Various embodiments of the subject innovation can be employed to use hardware and/or software to solve problems that are highly technical in nature (e.g., to facilitate automated localization of large vessel occlusions), that are not abstract and that cannot be performed as a set of mental acts by a human. Further, some of the processes performed can be performed by a specialized computer for carrying out defined tasks related to automated LVO localization (e.g., generating CTA images, analyzing the CTA images via a trained neural network; classifying the CTA images via the trained neural network, and so on). In various aspects, the subject innovation can provide technical improvements to the field of automated LVO localization, by automatically determining a specific and/or granular location (e.g., laterality and/or occlusion site) of an LVO within a patient's brain, rather than simply outputting a binary result that indicates only the mere presence of an LVO at some unspecified location in the patient's brain. Such embodiments can provide accurate, reliable, and efficient LVO localization, which can allow medical service providers to more quickly and effectively make treatment and patient-triage decisions than can existing LVO detection systems. Moreover, embodiments of the subject innovation can generate and display MIP reconstructions which allow users to visually verify automatically localized LVOs as desired as well as to manually evaluate collateral circulation. Such systems/techniques thus constitute a concrete and tangible technical improvement in the prior art.

Figure 1B:
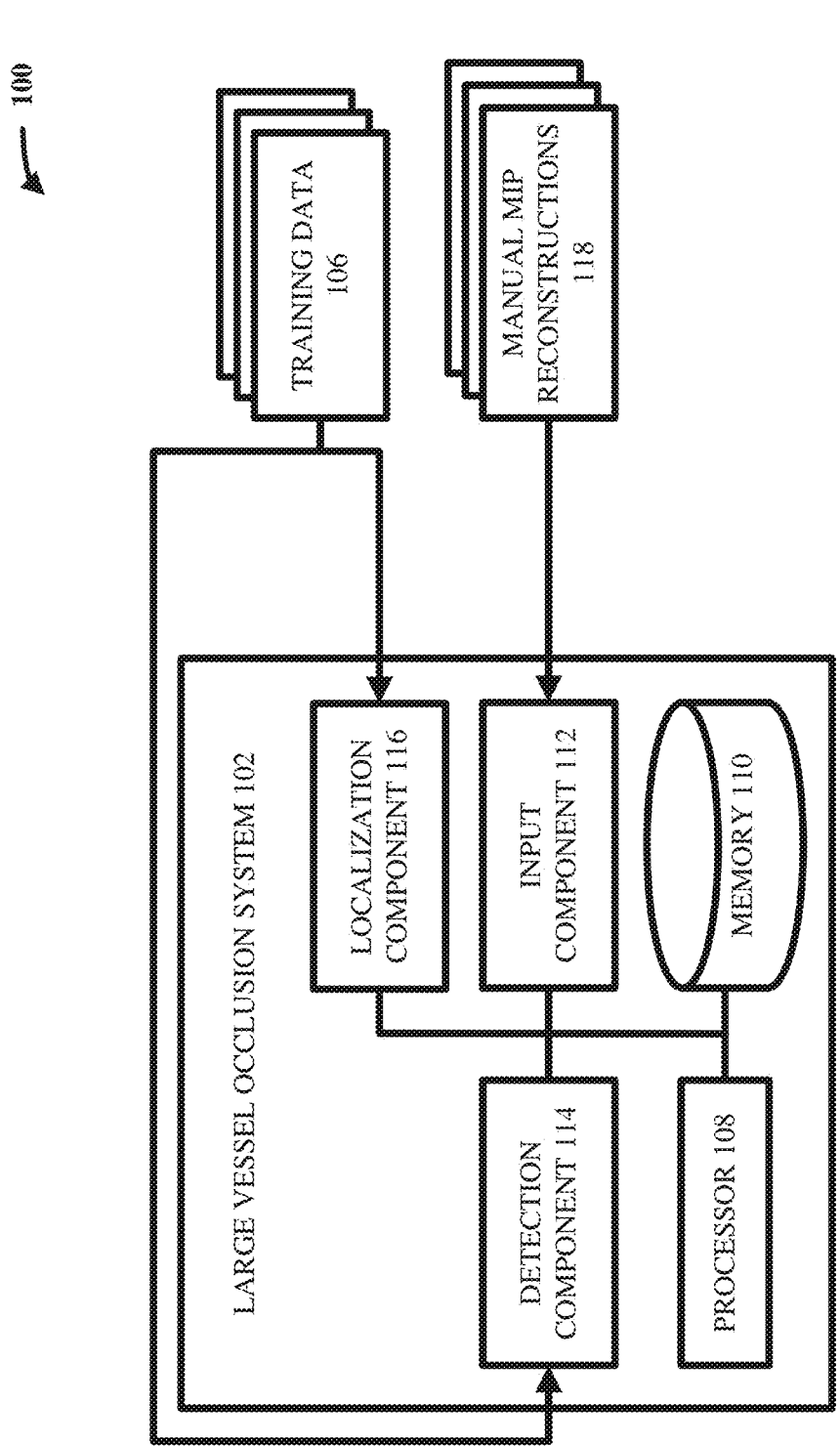

FIGS. 1A-1B illustrate a block diagram of an example, non-limiting system 100 that can facilitate automated localization of large vessel occlusions in accordance with one or more embodiments described herein. As shown, the large vessel occlusion system 102 (hereinafter referred to as LVO system 102) can, in various embodiments, localize one or more LVOs in a patient's brain by analyzing a series, set, and/or collection of axial CTA images 104 corresponding to the particular patient's brain. In various instances, the axial CTA images 104 can correspond to a particular patient and can be generated via any suitable computed tomography angiography techniques (e.g., introducing contrast agent/dye into a patient's bloodstream and using X-rays to visualize the contrast agent in the patient's circulatory system and/or vascular trees). In various instances, the axial CTA images 104 can comprise a plurality of two-dimensional computed tomography angiogram images taken at different positions (e.g., at regular intervals such as every 1 mm, at irregular intervals, and so on) along an axial direction (e.g., spinal direction) of the patient. That is, in various embodiments, the LVO system 102 can receive as input multiple CTA images of a single patient's brain, each of the images representing a different cross-sectional slice of the patient's brain along the axial direction, where each cross-sectional slice is substantially orthogonal to the axial direction. Based on these multiple CTA images, the LVO system 102 can determine/infer a location of an LVO in the patient's brain. For instance, the LVO system 102 can, in some embodiments, receive as input a 28×512×512 pixel array, representing 28 different images of the particular patient's brain taken at 28 different positions along the axial/spinal direction of the particular patient, where each image comprises 512×512 pixels. In various other embodiments, the axial CTA images 104 can comprise a single CTA image of a patient's brain. That is, in various embodiments, the LVO system 102 can receive as input a single CTA image of the patient's brain, the image representing a cross-sectional slice of the patient's brain along the axial direction, where the cross-sectional slice is substantially orthogonal to the axial direction. Based on this single CTA image, the LVO system 102 can determine/infer a location of an LVO in the patient's brain. For instance, the LVO system 102 can, in some embodiments, receive as input a 1×512×512 pixel matrix, representing 1 image of the patient's brain along the axial/spinal direction of the patient, where the image comprises 512×512 pixels.

In various embodiments, each CTA image in the axial CTA images 104 can be any suitable and/or desired shape and can comprise any suitable and/or desired number of pixels (e.g., 512×512 is exemplary and non-limiting; in some cases, 180×180 pixels can be implemented; in other cases, any suitable size can be implemented). In embodiments where the axial CTA images 104 comprise a plurality of images, any suitable and/or desired number of images can be used (e.g., the number 28 is exemplary and non-limiting; in some cases, 100 images can be implemented; in other cases, any suitable number of images can be implemented).

Although the herein description refers to the axial CTA images 104 as depicting images of a patient's brain (e.g., depicting the patient's skull and the contrast agent within the vascular tree of the patient's brain), it should be appreciated that, in various embodiments, the axial CTA images 104 can depict any suitable and/or desired portion of the circulatory system of the patient (e.g., the LVO system 102 can be implemented to detect vascular occlusions in any suitable and/or desired body part, such as brain, lungs, kidneys, heart, neck, and so on).

As shown in FIG. 1B, in various embodiments, rather that receiving the axial CTA images 104, the input component 112 can receive manual MIP reconstructions 118 (e.g., maximum intensity projection images of a patient created with manual input from a medical professional, such as a physician, nurse, technologist, and so on). In such embodiments, the LVO system 102 can analyze the manual MIP reconstructions 118 in order to detect/localize LVOs in a patient rather than analyzing the axial CTA images 104 directly. Although the remaining figures depict the axial CTA images 104, it is to be appreciated that the remaining figures and associated discussions can, in various aspects, be applied to embodiments of the subject innovation that receive the manual MIP reconstructions 118.

In various embodiments, the LVO system 102 can be trained on training data 106. In various cases, the training data 106 can be a collection of CTA images that have been labeled, annotated, and/or classified by experts (e.g., by physicians, nurses, and so on) and/or that otherwise are known to exhibit particular LVOs, and so on. In such cases, the training data 106 can be used to facilitate supervised training (e.g., via backpropagation, and so on) of the LVO system 102. In various instances, other forms of training of the LVO system 102 can be facilitated using the training data 106 (e.g., unsupervised learning, reinforcement learning, and so on). In various aspects, the training data 106 can mirror and/or correspond to the axial CTA images 104. For instance, if the LVO system 102 is structured/designed to receive as input only a single CTA image of a patient's brain, then the axial CTA images 104 can comprise only a single image of a patient's brain, and the training data 106 can comprise a collection of single images of different patients' brains. In such cases, each single image in the collection of single images can have a known label (e.g., a known LVO localization). Similarly, if the LVO system 102 is instead structured/designed to receive as input a set of images of a patient's brain (e.g., 28 cross-sectional views of one patient's brain), then the axial CTA images 104 can comprise a set of images of a single patient's brain, and the training data 106 can comprise a collection of sets of images, each set corresponding to a different patient's brain. In such cases, each set of images in the collection can have a known label (e.g., a known LVO localization).

In various aspects, the more robust, complete, and/or realistic the training data 106 is, the more effective the LVO system 102 can become (e.g., more effective training can yield more effective machine learning models). In various experiments, the inventors of the subject innovation collected a total dataset of 3584 head CTA studies from between January 2005 and September 2018 from appropriate radiology archives. Each head CTA was labeled/annotated with presence, absence, and/or location of LVO. Specifically, there were approximately 1608 (45%) that were positive for LVO. During the experiments, the total CTA dataset was randomly split into a training dataset (2860, or about 80%), a validation dataset (379, or about 10%), and a test dataset (345, or about 10%). The demographics of the total dataset were approximately 50% female and 50% male, with a mean and standard deviation age of 64+18 years.

In various embodiments, the training data 106 can be considered as comprising pairs of features and labels (e.g., the training data 106 can comprise a plurality of features, with each different feature representing one or more CTA images of a different patient's brain, and where each feature has a corresponding label indicating whether and/or where the images in that feature depict an LVO). In some cases, the features can comprise axial CT angiogram images (and/or automatically registered CT THINS images, as explained with respect to FIGS. 21-26), where the images can be selected based on DICOM data elements (e.g., modality: "CT"; series description; SOP Class UID: "1.2.840.10008.5.1.4.1.1"; Image Type: ["DERIVED", . . . , . . . , "MIP"]; Slice Thickness: 28-32 millimeters; Image Orientation Patient: [1, 0, 0, 0, 1, 0]; and so on). In various cases, the images can be sorted based on DICOM data elements (e.g., Image Orientation Patient; Image Position Patient; and so on). In various aspects, each feature can comprise 28 images of a patient's brain (e.g., middle slice+/−14 slices, where each slice can be 1 mm in thickness). In various embodiments, each feature can have an associated label, indicating the presence, absence, and/or location of an LVO depicted in that feature. In various cases, the label can comprise and/or be derived from a cardiovascular analysis report. For instance, the labels can be annotated findings described in free-text reports after review of images by neuroradiologists. In some cases, the label can include a laterality (e.g., left, right) and an occlusion sight (e.g., ICA, M1 of MCA, M2 of MCA, PCA, and so on).

In various embodiments, the axial CTA images 104 can be considered as a single feature (e.g., comprising one or more CTA images of a single patient's brain), which the LVO system 102 is required to label/classify (e.g., to determine and/or infer a location of an LVO depicted in the axial CTA images 104). In some embodiments, the LVO system 102 can be trained to identify a plurality of LVOs in a single patient's brain (e.g., if the axial CTA images 104 depict multiple LVOs at multiple locations in a single brain). The training data 106 can be structured accordingly (e.g., labeled to identify all LVOs in every patient's brain) to facilitate such multi-LVO localization.

In various embodiments, preprocessing of the training data 106 and/or the axial CTA images 104 can be performed to improve operation. For instance, during training, validation, testing, and/or inference, unsigned pixel intensities can be mapped to signed intensities in Hounsfield unit (HU), intensities can be clipped below value in [0, 200] and/or above value in [1000, 5000], and intensities can be cast to floating points and rescaled to [−1, 1]. In other cases, during training, validation, testing, and/or inference, unsigned pixel intensities can be mapped to multiple channels of Hounsfield unit (HU) window levels, and intensities can be cast to floating points and rescaled to [−1, 1]. In various embodiments, preprocessing during training, validation, testing, and/or inference can include: implementing lateral registered THINS with padding of 20 pixels on each side in x-axis and/or y-axis; can include three window levels (e.g., 100±150, 150±350, 300±450); center cropping the images to 80×145×145 pixels; and/or implementing a mirror crop to get both literalities.

Figure 2:
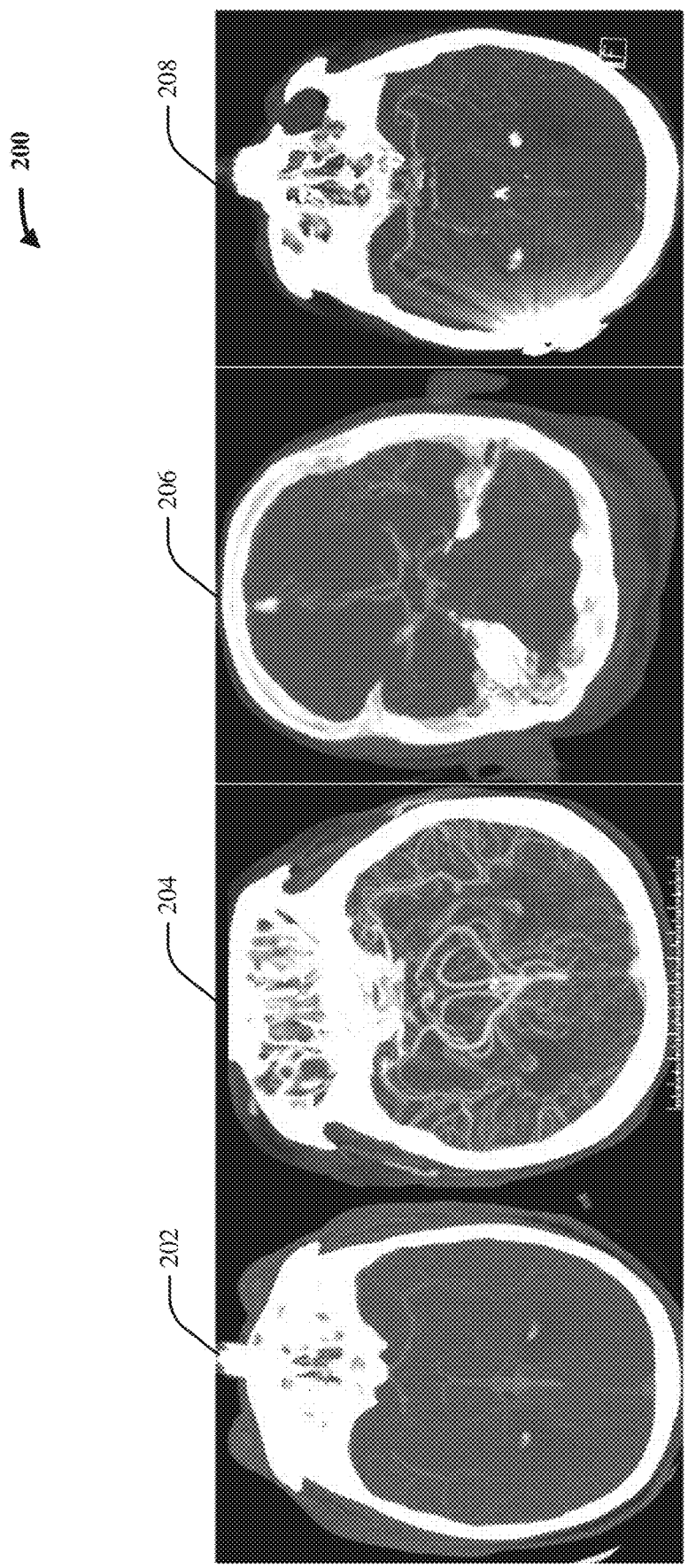
FIG. 2 illustrates exemplary, non-limiting images depicting CTA heterogeneity in accordance with one or more embodiments described herein.

In various embodiments, augmentation of the training data 106 can be performed to improve operation (e.g., to appropriately reflect real-world heterogeneity in the training data 106). FIG. 2 illustrates exemplary, non-limiting images depicting CTA heterogeneity in accordance with one or more embodiments described herein. Specifically, image 202 is an exemplary depiction of a CTA image of a patient's brain that was acquired too early (e.g., before the contrast agent had a chance to sufficiently diffuse through the patient's vascular tree). Image 204 is an exemplary depiction of a CTA image of a patient's brain that was acquired too late. Image 206 is an exemplary depiction of a CTA image of a patient's brain that was acquired using suboptimal angulation. Image 208 is an exemplary depiction of a CTA image of a patient's brain that includes metallic artifacts. The real-world heterogeneities depicted in FIG. 2 and/or other heterogeneities can distort CTA images, which can impede evaluation of CTA images by the LVO system 102. In order to help make the LVO system 102 robust (e.g., able to accurately localize LVOs despite the presence of image distortions and/or other artifacts), random augmentation can be performed on the training data 106. Such augmentation can enhance training efficacy of the LVO system 102. In various aspects, random augmentation can include randomly choosing a lateral input (e.g., right/left), introduction of random noise from various probability distributions (e.g., Gaussian, Poisson, Gamma), in-plane rotation on one or more CTA images by a random degree (e.g., rotation about the z-axis by some random degree sampled from range [−10, 10]), in-plane translation by a random offset (e.g., translation along x-axis and/or y-axis by random offsets in millimeter sampled from range [−10, 10]), out-of-plane translation by a random offset (e.g., translation along z-axis by random offsets in instance number sampled from range [−1, 1]), random pixel intensity offset between [−30, 30]-[−50, 50], padded crop between [80-100]×[180-200]×[180-200], random crop of 80×145×145, and/or scaling by a random factor (e.g., scaling factor randomly sampled from range [0.95, 1.05], scaling factor randomly sampled from range [0.85, 1.15]). In various embodiments, such random augmentation of the training data 106 can approximate real-world heterogeneity. Training the LVO system 102 on such data can result in a more robust LVO system 102 (e.g., LVO system 102 able to accurately localize LVOs notwithstanding distortions and/or artifacts in the CTA images).

In various embodiments, the LVO system 102 can comprise a processor 108 (e.g., computer processing unit, microprocessor, and so on) and a computer-readable memory 110 that is operably and/or operatively and/or communicatively connected/coupled to the processor 108. The memory 110 can store computer-executable instructions which, upon execution by the processor 108, can cause the processor 108 and/or other components of the LVO system 102 (e.g., input component 112, detection component 114, localization component 116, and so on) to perform one or more acts. In various embodiments, the memory 110 can store computer-executable components (e.g., input component 112, detection component 114, localization component 116, and so on), and the processor 108 can execute the computer-executable components.

In various embodiments, the LVO system 102 can comprise an input component 112. The input component 112 can, in various instances, electronically receive the axial CTA images 104. In various embodiments, the input component 112 can be any suitable device communicatively coupled, via a wired and/or wireless connection, to a CT scanning apparatus, such that when the CT scanning apparatus generates the axial CTA images 104, the CT scanning device can electronically communicate/transfer, via a wired and/or wireless connection, the axial CTA images 104 to the input component 112 for analysis. In various embodiments, the input component 112 can perform the above-mentioned preprocessing of the training data 106 and/or the axial CTA images 104, and/or can perform the above-mentioned random augmentation of the training data 106 during training.

In various embodiments, the LVO system 102 can comprise a detection component 114. The detection component 114 can, in various instances, detect an LVO depicted in the axial CTA images 104. In various aspects, the detection component 114 can employ a binary machine learning model (e.g., a neural network, any other suitable artificial intelligence paradigm, and so on), which can receive as input the axial CTA images 104 and produce as output a binary result indicating that the axial CTA images 104 do or do not depict an LVO. If the detection component 114 determines that the axial CTA images 104 do not depict an LVO, such result can be communicated to the user. If the detection component 114 determines that the axial CTA images 104 do depict an LVO, subsequent processing of the axial CTA images 104 by the LVO system 102 can be performed. In various instances, the detection component 114 (e.g., the binary model of the detection component 114) can be trained on the training data 106 to detect presence/absence of LVOs.

In various embodiments, the LVO system 102 can comprise a localization component 116. The localization component 116 can, in various instances, localize (e.g., determine and/or infer a location of) an LVO depicted in the axial CTA images 104. In various aspects, the localization component 116 can employ a multi-classification model (e.g., a neural network, any other suitable artificial intelligence paradigm, and so on), which can receive as input the axial CTA images 104 and produce as output a non-binary result indicating a location of an LVO within a patient's brain. As explained above, the detection component 114 can analyze the axial CTA images 104 to determine whether any LVO is depicted at all. If the detection component 114 determines that an LVO is present in the axial CTA images 104, the localization component 116 can analyze the axial CTA images 104 in order to determine/infer the location of the LVO within the vascular tree of the patient's brain (e.g., LVO in right/left ICA, LVO in M1 segment of right/left MCA, LVO in proximal M2 segment of right/left MCA, LVO in distal M2 segment of right/left MCA, LVO in M3 segment of right/left MCA, LVO in right/left PCA, any other desired vascular locations, such as A1, P1, Basilar, Vertebral, and so on). In various instances, the localization component 116 (e.g., the multi-classification model employed by the localization component 116) can be trained on the training data 106 to determine/infer location of detected LVOs.

In various embodiments, the localization component 116 can be trained to identify more than one LVO in the axial CTA images 104. For instance, if the patient has both an LVO in the right ICA and an LVO in the M1 segment of the left MCA, the localization component 116 can, in various instances, be trained to localize both of the depicted LVOs (e.g., the localization component 116 can output a scalar result indicating that multiple LVOs were detected and/or indicating where the multiple LVOs are located). Such multi-LVO localization can be facilitated by appropriately labeling the sets of images in the training data 106.

Although the figures show the LVO system 102 as having both the detection component 114 and the localization component 116, various embodiments of the subject innovation can lack the detection component 114. In such embodiments, the LVO system 102 need not first determine whether the axial CTA images 104 depict an LVO before attempting to localize the LVO. Instead, the localization component 116 (e.g., the multi-classification model of the localization component 116) can, in various instances, be trained to both detect and localize LVOs in the axial CTA images 104.

As a non-limiting and exemplary summary of FIGS. 1A-1B, consider the following example. Suppose that the LVO system 102 is trained on the training data 106 to localize LVOs in a patient's brain in six possible locations: right or left ICA, M1 segment of right or left MCA, and M2 segment of right or left MCA. In such case, the detection component 114 can, in some embodiments, be trained to output a 0 if no LVO is detected in the axial CTA images 104, and to output a 1 if an LVO is detected in the axial CTA images 104. Moreover, the localization component 116 can, in some embodiments, be trained to output a 1 to indicate that the LVO is detected in the left ICA, a 2 to indicate that an LVO is detected in the right ICA, a 3 to indicate that an LVO is detected in the M1 segment of the left MCA, a 4 to indicate that the LVO is detected in the M1 segment of the right MCA, a 5 to indicate that the LVO is detected in the M2 segment of the left MCA, or a 6 to indicate that the LVO is detected in the M2 segment of the right MCA. Suppose moreover that the patient in question has an LVO in the M1 segment of the left MCA. Then, the axial CTA images 104 of the patient's brain can be generated using any suitable techniques known in the art (e.g., CT scanning machinery in combination with injected contrast material). The input component 112 can electronically receive the axial CTA images 104 and perform any suitable preprocessing as necessary/desired. The detection component 114 can then analyze the axial CTA images 104 via a trained binary classification machine learning model to determine whether an LVO is depicted at all in the axial CTA images 104. Since an LVO is indeed depicted in the axial CTA images 104, the detection component 114 can output a scalar value of 1, indicating that an LVO is detected. The localization component 116 can then analyze the axial CTA images 104 via a trained multi-classification machine learning model to determine/infer where the LVO is located within the patient's brain. Since the LVO is depicted as being in the M1 segment of the left MCA, the localization component 116 can output a scalar value of 3. In this way, fast, efficient, and accurate LVO localization can be facilitated by the LVO system 102.

As another non-limiting example, the localization component 116 can be fed CTA images of each laterality of a patient, and can generate as output two scalar values for each laterality. In various aspects, a first scalar value can denote a prediction/determination that an LVO is present or absent in the given laterality (e.g., the first scalar can represent a probability that the given laterality has an LVO), and a second scalar value can denote a prediction/determination of a subtype localization of the LVO (e.g., ICA, MCA-1, MCA-2). As mentioned above, the second scalar value can be considered as relevant when the first scalar value indicates that an LVO is present in the given laterality, and the second scalar value can be considered as irrelevant when the first scalar value indicates that an LVO is not present in the given laterality.

As another non-limiting example, suppose that the LVO system 102 lacks the detection component 114. In such case, the localization component 116 can, in various embodiments, be trained on the training data 106 to both detect and localize LVOs in the axial CTA images 104. In some cases, the localization component 116 can output a single scalar value that indicates the granular location of the detected LVO. For instance, the localization component 116 can be trained to output a scalar value of 0 to indicate that no LVO is detected in the axial CTA images 104, a value of 1 to indicate that an LVO is detected in the right ICA, a 2 to indicate that an LVO is detected in the left ICA, a 3 to indicate that an LVO is detected in the M1 segment of the right MCA, a 4 to indicate that an LVO is detected in the M2 segment of the right MCA, a 5 to indicate that an LVO is detected in the M1 segment of the left MCA, or a 6 to indicate that an LVO is detected in the M2 segment of the left MCA. Suppose moreover that the patient in question has an LVO in the left ICA. Then, the axial CTA images 104 of the patient's brain can be generated using any suitable techniques known in the art (e.g., CT scanning machinery in combination with injected contrast material). The input component 112 can electronically receive the axial CTA images 104 and perform any suitable preprocessing as necessary/desired. The localization component 116 can then analyze the axial CTA images 104 via a trained multi-classification machine learning model to determine/infer whether an LVO is detected at all and, if detected, where the LVO is located within the patient's brain. Since the LVO is depicted as being in the left ICA, the localization component 116 can output a scalar value of 2. In this way, fast, efficient, and accurate LVO localization can be facilitated by the LVO system 102.

In various cases, the localization component 116 can output multiple scalar results, each one indicating a different aspect of the detected/localized LVOs (e.g., a first scalar output binarily indicating presence or absence of an LVO, a second scalar output binarily indicating right or left side of the patient's brain, and a third scalar output indicating occlusion site). In some cases, the localization component 116 can be trained to detect LVOs in m different locations, and can thus be designed to output m scalar results, with each scalar result corresponding to one of the m locations and binarily indicating whether an LVO is located/detected in that location of the patient's brain (e.g., a first scalar that is either 0 or 1 to indicate the presence or absence of an LVO in the right ICA, a second scalar that is either 0 or 1 to indicate the presence or absence of an LVO in the left ICA, a third scalar that is either 0 or 1 to indicate the presence or absence of an LVO in the right M1, a fourth scalar that is either 0 or 1 to indicate the presence or absence of an LVO in the left M1, and so on). Such embodiments can, in some cases, be used to facilitate multi-LVO localization (e.g., localizing multiple LVO's in a single patient's brain).

Figure 3:
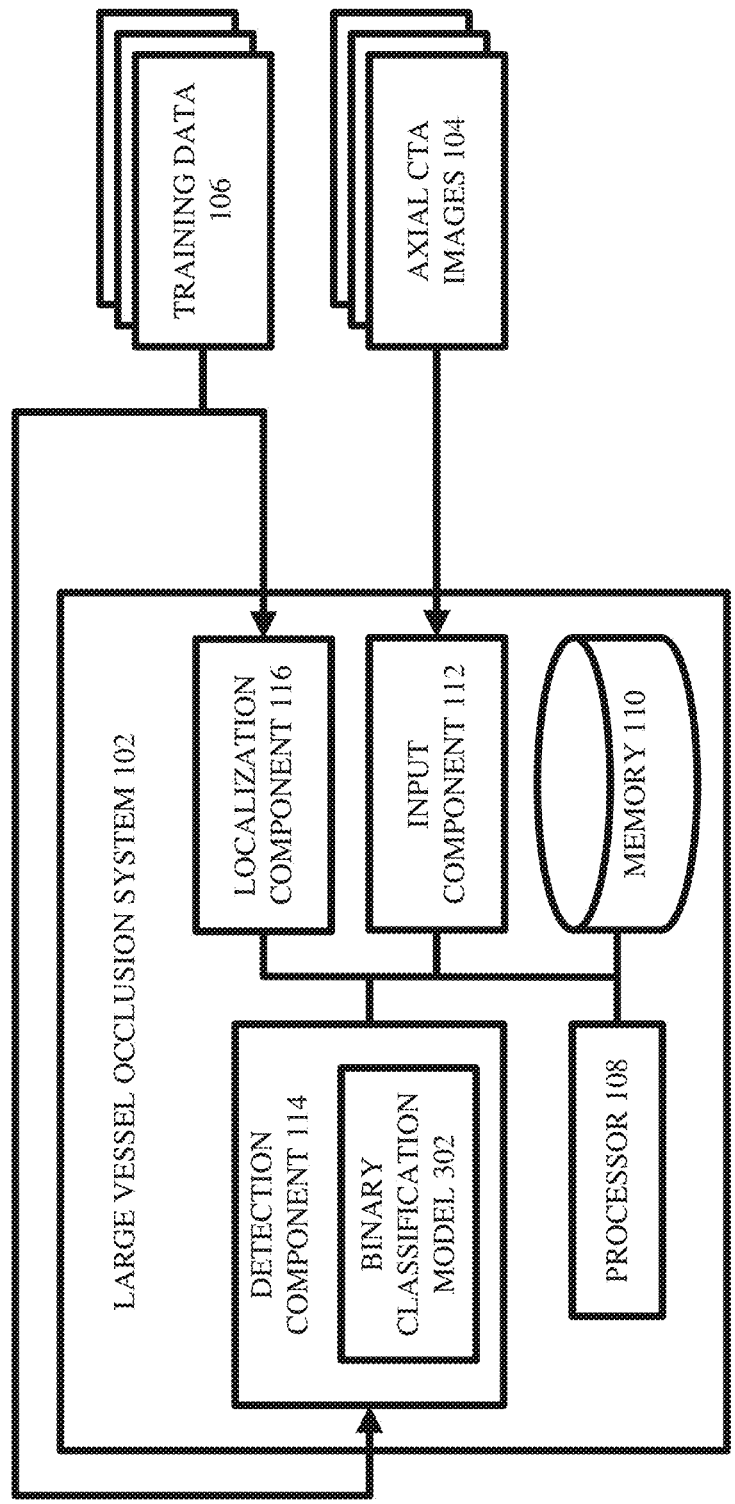
FIG. 3 illustrates a block diagram of an example, non-limiting system including a binary classification model that facilitates automated localization of large vessel occlusions in accordance with one or more embodiments described herein.

FIG. 3 illustrates a block diagram of an example, non-limiting system 300 including a binary classification model that can facilitate automated localization of large vessel occlusions in accordance with one or more embodiments described herein. The system 300 can, in various embodiments, comprise the same components as the system 100, and can further comprise a binary classification model 302.

In various instances, the binary classification model 302 can be a three-dimensional convolutional neural network including residual bottleneck blocks and/or including dense blocks that can receive as input the axial CTA images 104 and output a binary result (e.g., indicating LVO presence or absence). In various instances, the binary classification model 302 can be any suitable machine learning, deep learning, and/or pattern recognition model known in the art that can be trained (e.g., supervised learning, unsupervised learning, reinforcement learning, and so on) to perform binary classification tasks with algorithms (e.g., neural networks, support vector machines, logistic regression, and so on).

To facilitate some of the above-described machine learning aspects of various embodiments of the subject innovation, consider the following discussion of artificial intelligence. Various embodiments of the present innovation herein can employ artificial intelligence (AI) to facilitate automating one or more features of the present innovation. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute, and so on) of the present innovation, components of the present innovation can examine the entirety or a subset of the data to which it is granted access and can provide for reasoning about or determine states of the system, environment, and so on from a set of observations as captured via events and/or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes and/or systems (e.g., support vector machines, neural networks, expert systems, Bayesian belief networks, fuzzy logic, data fusion engines, and so on) in connection with performing automatic and/or determined action in connection with the claimed subject matter. Thus, classification schemes and/or systems can be used to automatically learn and perform a number of functions, actions, and/or determinations.

A classifier can map an input attribute vector, z=(z1, z2, z3, z4, zn), to a confidence that the input belongs to a class, as by f(z)=confidence(class). Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence, any of which can be employed. Classification as used herein also is inclusive of statistical regression that is utilized to develop models of priority.

Figure 4A:
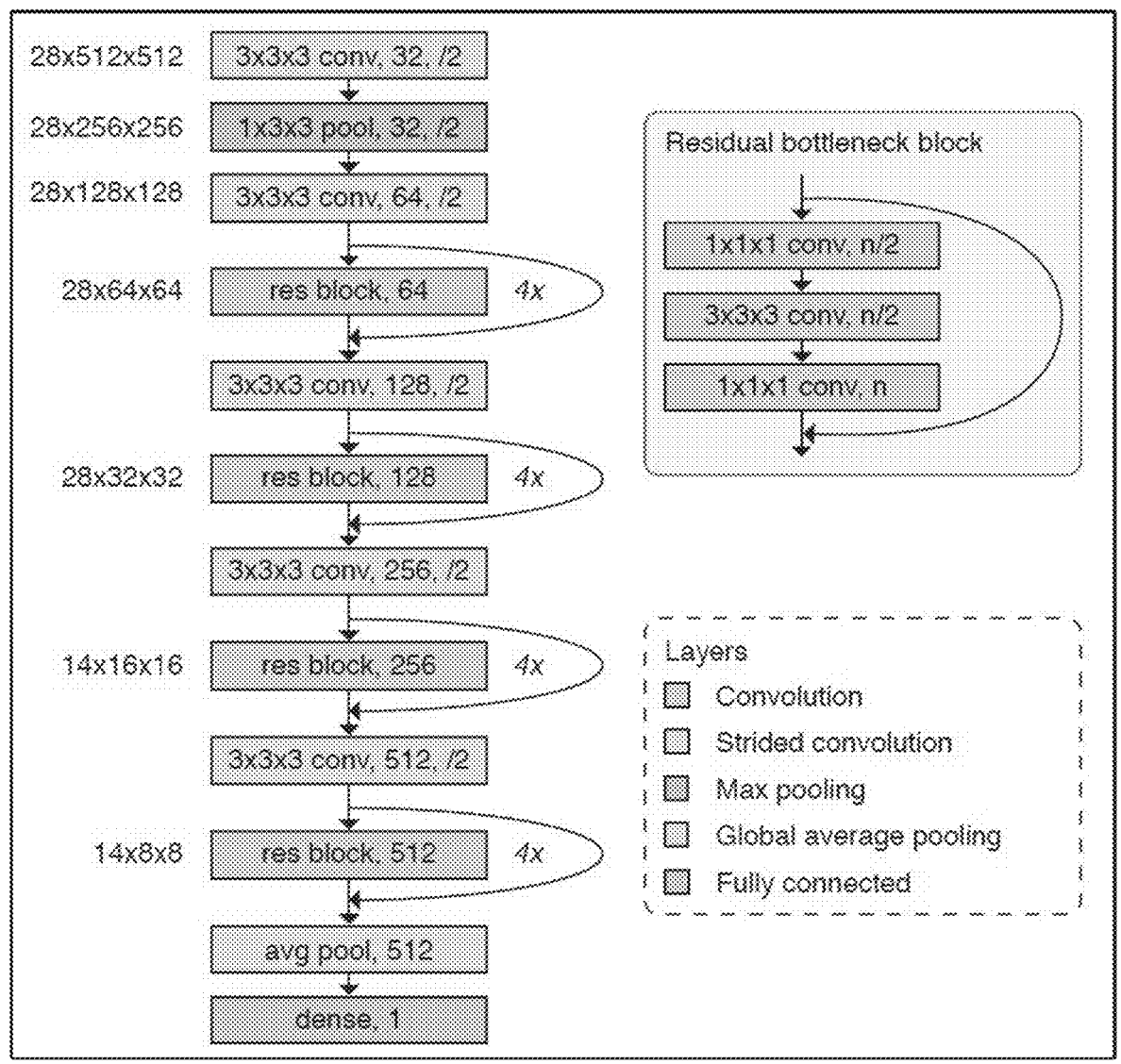
FIGS. 4A-4B illustrate block diagrams of example, non-limiting neural network architectures that facilitate automated localization of large vessel occlusions in accordance with one or more embodiments described herein.
Figure 4B:
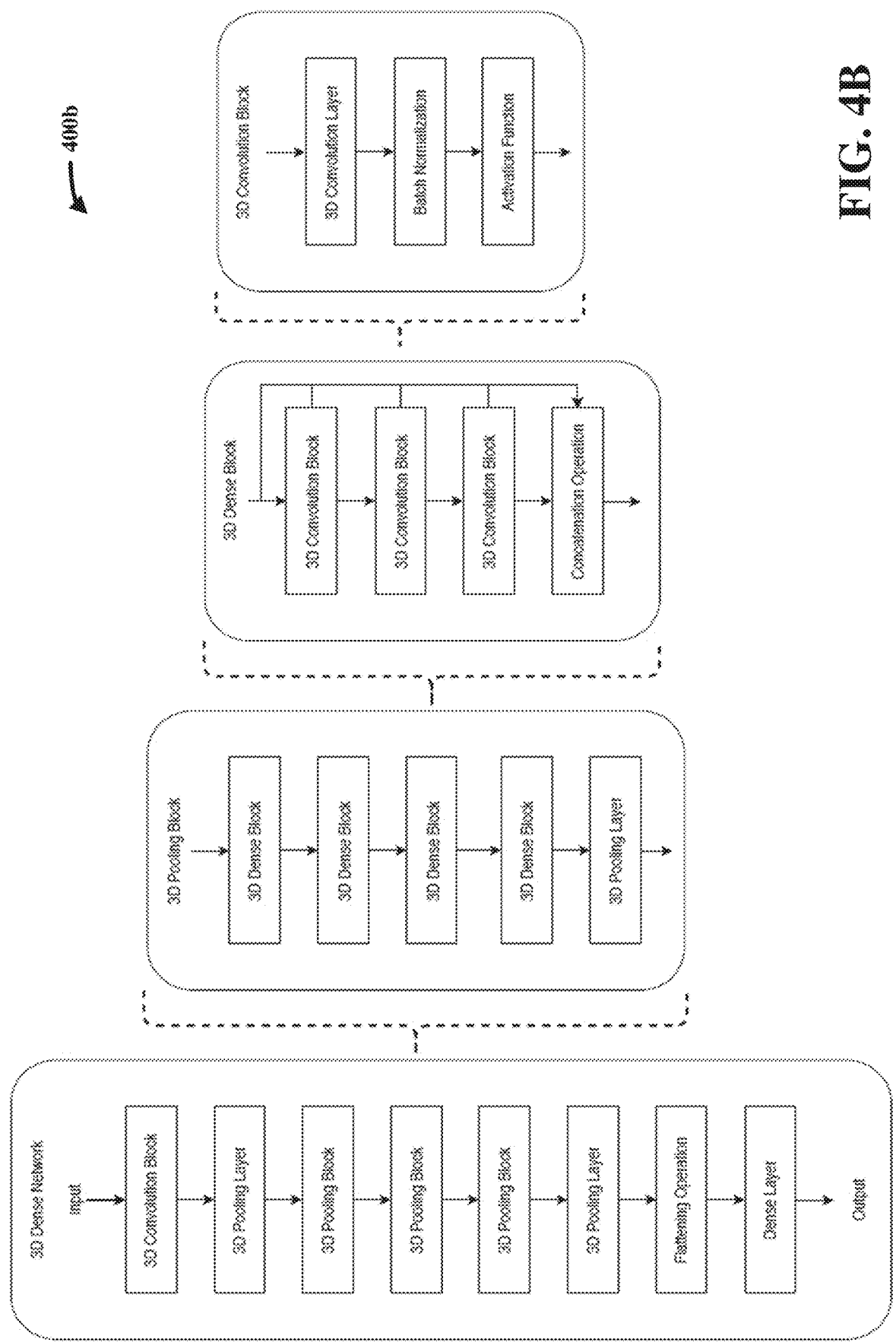

FIGS. 4A-4B illustrate block diagrams of example, non-limiting neural network architectures that can facilitate automated localization of large vessel occlusions in accordance with one or more embodiments described herein. Those having ordinary skill in the art will appreciate that FIGS. 4A-4B can apply to binary classification models (e.g., detecting the presence or absence of an LVO), to multi-class classification models (e.g., detecting the laterality and/or localization of an LVO), and/or to hybrid models (e.g., detecting presence or absence of an LVO, and if an LVO is determined to be present, then detecting the laterality and/or localization). Accordingly, the below description pertaining to FIGS. 4A-4B include some discussion of binary classification as well as some discussion of laterality and/or localization.

In various instances, the exemplary architectures 400a and/or 400b can be used to construct and/or implement the binary classification model 302.

As shown in FIG. 4A, in various embodiments, the binary classification model 302 can exhibit a neural network architecture 400a that first includes receiving a 28×512×512 input pixel array (e.g., corresponding to 28 different CTA slices depicting the patient's brain) and scaling it down by a factor of 2 (e.g., from 28×512×512 to 28×256×256) using a strided convolution layer (e.g., with a 3×3×3 convolution kernel/filter). As shown, a max pooling layer (e.g., with a 1×3×3 convolution kernel/filter) can be used to again scale down the array by a factor of 2 (e.g., from 28×256×256 to 28×128×128). Next, a series of alternating strided convolution layers (e.g., with 3×3×3 convolution kernels/filters) and residual bottleneck blocks can be included to continue analyzing/scaling down the array. In various instances, each residual bottleneck block can include a first convolutional layer having a 1×1×1 kernel/filter, a second convolutional layer having a 3×3×3 kernel/filter, and a third convolutional layer having a 1×1×1 kernel/filter. After the final residual bottleneck block, the array can be received by a global average pooling layer, and a final scalar value can be outputted indicating whether an LVO was detected. In various embodiments, the architecture 400a can be considered as an adapted 3D ResNet architecture, including three dimensional convolutions, batch normalization, and leaky ReLU activation. In various instances, the architecture 400a can be 53 layers deep with residual connections, can include two-dimensional iterative downsampling, and can be 32-512 channels wide.

As shown in FIG. 4B, in various embodiments, the binary classification model 302 can exhibit a neural network architecture 400b that first includes receiving a 90×145×145 input pixel array (e.g., corresponding to 90 different CTA slices depicting the patient's brain) and scaling it down by a factor of 2 (e.g., from 90×145×145 to 45×72×72) using a 3D convolutional block (e.g., with a 3×3×3 convolution kernel/filter). As shown, a series of 3D pooling blocks (e.g., any suitable number of 3D pooling blocks) can be implemented, where each 3D pooling block can comprise a series of 3D dense blocks (e.g., any suitable number of 3D dense blocks). As shown in FIG. 4B, each 3D dense block can comprise a series of 3D convolution blocks (e.g., any suitable number of 3D convolution blocks), where the original input of the 3D dense block is fed to each of its constituent 3D convolution blocks. As shown, each 3D convolution block can comprise a 3D convolution layer, a batch normalization layer, and an activation function layer. In various embodiments, the architecture 400b can be considered as an adapted 3D DenseNet architecture, including three dimensional convolutions, batch normalization, and ReLU activation. In various instances, the architecture 400b can be 50 layers deep, 96 layers deep, and/or any other suitable number of layers deep with dense connections; can include 3 downsampling pooling layers and/or any other suitable number of downsampling pooling layers; can include 32-64 initial channel filters; can include a growth rate of 32-64; and/or can include a compression value of 0.5. In various aspects, the architecture 400b can receive as input three-dimensional registered unilateral regions with 3 different window levels and can produce as output scalar values for binary detection of LVOs and/or can also produce as output "hemi" laterality loss and/or multiclass vessel prediction (e.g., for embodiments that detect localization).

In various embodiments, the binary classification model 302 can be an ensemble of sub-models. For instances, a plurality of binary classification sub-models can be trained on the training data 106, each sub-model being a neural network and/or any other suitable machine learning classification paradigm, with the sub-models having different architectures and/or hyperparameters from each other. The performance of these sub-models can be evaluated after training on a validation data set, and the top performing sub-models can be selected (e.g., based on Area Under the Curve of Receiver Operating Characteristics (AUC of ROC) as the evaluation metric). The top performing sub-models can be ensembled together by using majority vote of their prediction results of each sub-model and using that result as the final output of the binary classification model 302. Lateralization and localization outputs can be ensembled in similar manner. In various embodiments, the sub-models' outputs can be combined and/or ensembled via any suitable mathematical and/or statistical technique. In various cases, the user can choose a decision threshold such that sensitivity of the ensemble is greater than and/or equal to 90%. In various embodiments, such ensembling can be advantageous due to the black-box nature of neural networks and other machine learning models. Since differently structured machine learning models can pick up on different characteristics of input data and thus each be better suited to detecting different types of LVOs, ensembling the binary classification model 302 can result in more robust and accurate LVO detections.

In various embodiments, the following hyperparameters for optimization can be used when the architecture 400*a* is implemented. Adam optimization can be implemented. Learning rate can be within [7.0e-06, 14.0e-06] with exponential decay with base 0.98 and exponent step/200. Loss function can be focal loss based on categorical cross entropy between predicted probabilities and ground truth labels. Regularization can be L2 norm [0.07, 0.53], with dropout [0.02, 0.13].

In various embodiments, the following hyperparameters for optimization can be used when the architecture 400*b* is implemented. AdamW optimization can be implemented with beta parameters (0.9, 0.99) and AMSgrad correction and weight decay between 0.05-0.15. Learning rate can be 0.0001-0.000001 with plateau scheduler of 15-20 patience, cooldown of 5, and reduction of 0.5×. In some cases, hemisphere or "hemi" loss can be self-supervised loss to predict laterality of input images. Loss function can include cross entropy for detection/hemi with weighting 0.95 in favor of positive class and weighted cross-entropy for multiclass (negative, ICA, M1, M2) with weighting between [0.01, 0.3, 0.4, 0.29] respectively. In various aspects, batch-normalization regularization can be implemented.

Figure 5A:
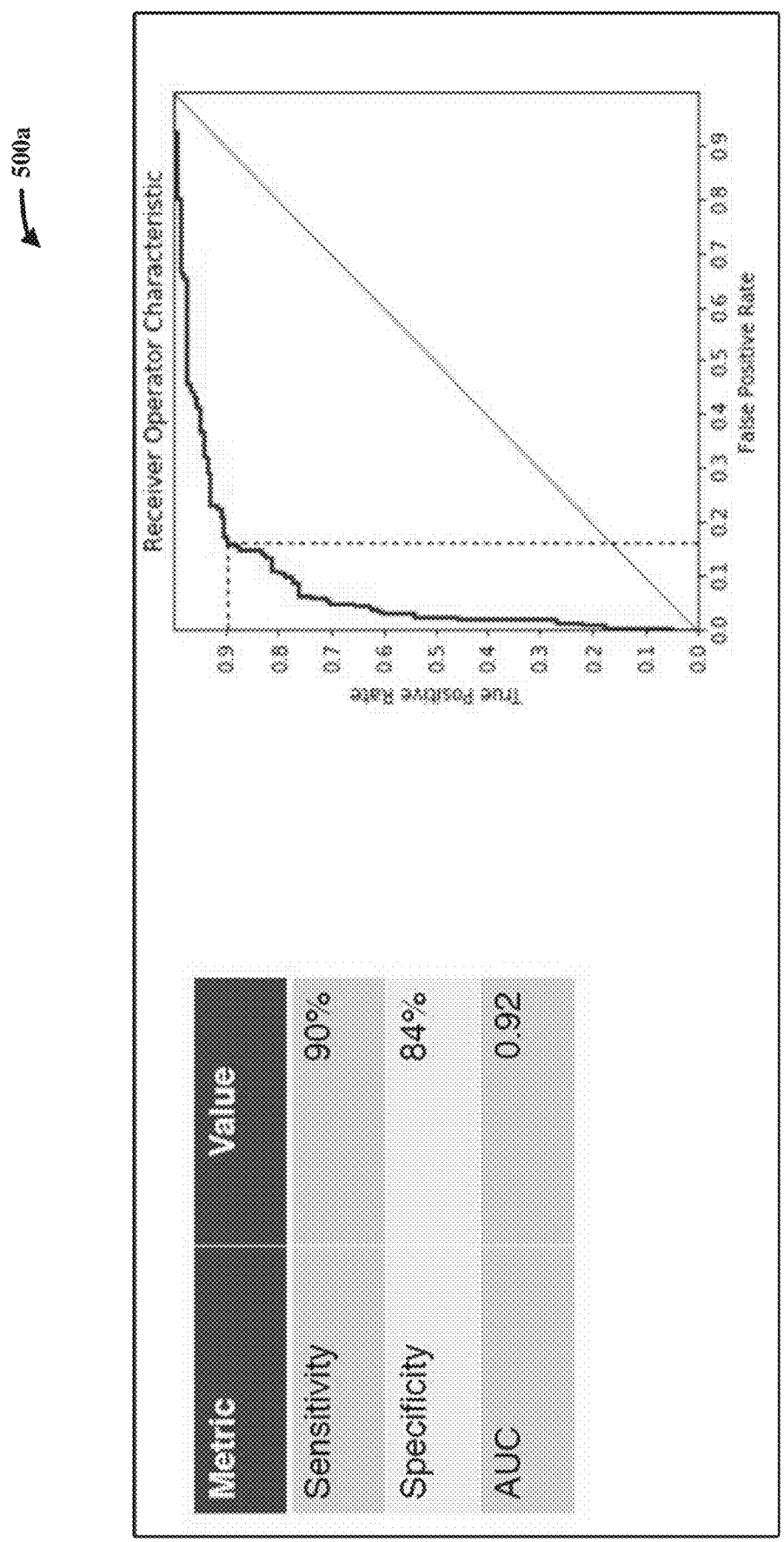
FIGS. 5A-5B illustrate exemplary, non-limiting experimentation results of a binary classification model that facilitates automated localization of large vessel occlusions in accordance with one or more embodiments described herein.
Figure 5B:
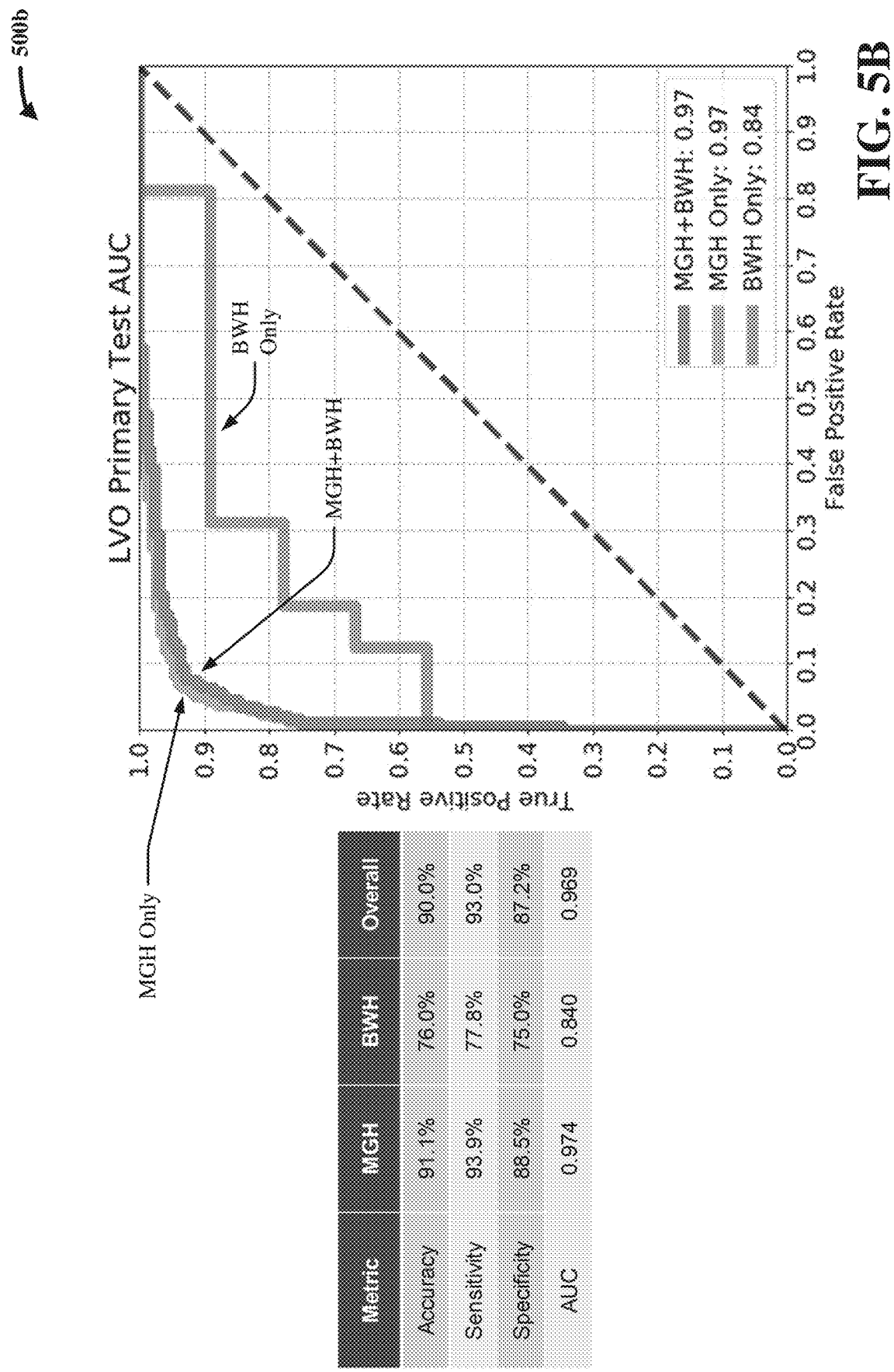

FIGS. 5A-5B illustrate exemplary, non-limiting experimentation results of a binary classification model that can facilitate automated localization of large vessel occlusions in accordance with one or more embodiments described herein. Experiments regarding the binary classification model 302 performed by the inventors of the subject innovation yielded results as depicted in FIGS. 5A-5B.

First, consider FIG. 5A, which shows results associated with the binary classification model 302 when the architecture 400*a* is implemented. As shown in the results, a fully trained embodiment of the binary classification model 302, which was trained, validated, and tested on the dataset described above, yielded a sensitivity (e.g., true positive rate) of 90%, a specificity (e.g., true negative rate) of 84%, and an AUC of 0.92. Specifically, an embodiment of the binary classification model 302 was tested on a test set consisting of 352 random samples, with 154 positive samples and 198 negative samples. The binary classification model 302 correctly classified 138 of the 154 positive samples and 166 of the 198 negative samples. This particular embodiment of the binary classification model 302 thus had 16 false negative results and 32 false positive results. Of the true positive findings, 5.8% were located in the ICA, 36.2% were located in an M2 segment of the MCA, 13.8% were located in an M1 segment of the MCA, 16.7% were located in both the M1 and M2 segments of the MCA, and 27.5% were located in both the ICA and the MCA. Of the false negative findings, 31.2% were in the ICA, 31.2% were in the M2 segment of the MCA, 12.5% were in the M1 segment of the MCA, 6.2% were in both the M1 and M2 segments of the MCA, and 18.8% were in both the ICA and the MCA. Of the true positive results, 48.6% exhibited right laterality, and 51.4% exhibited left laterality. Of the false negative results, 31.2% exhibited left laterality, and 68.8% exhibited right laterality. Of the true positive results, 37% exhibit equivocal collaterals, 38.4% exhibited normal collaterals, and 24.6% exhibited low collaterals. Of the false negative results, 18.8% exhibited equivocal collaterals, 75% exhibited normal collaterals, and 6.2% exhibited low collaterals. Of the true positive results, 3.6% were deemed non-obvious occlusions by medical professionals, and 96.4% were deemed obvious occlusions. Of the false negative results, 23.5% were deemed non-obvious occlusions, and 76.5% were deemed obvious occlusions. Of the true negative results, 92.2% involved 0 reported occlusions at non-LVO finding sites (e.g., distal M2, M3, A1, P1, Basilar, Vertebral), 5.4% involved 1 reported occlusion at non-LVO finding sites, 1.8% involved 2 reported occlusions at non-LVO finding sites, and 0.6% involved 3 reported occlusions at non-LVO finding sites. Of the false positive results, 71.9% involved 0 reported occlusions at non-LVO finding sites, 21.9% involved 1 reported occlusion at non-LVO finding sites, and 6.2% involved 2 reported occlusions at non-LVO finding sites. Of the true negative results, 95.2% involved 0 reported stenosis at non-LVO finding sites, 2.4% involved 1 reported stenosis at non-LVO finding sites, 1.2% involved 2 reported stenosis at non-LVO finding sites, and 1.2% involved 3 reported stenosis at non-LVO finding sites. Of the false positive results, 68.8% involved 0 reported stenosis at non-LVO finding sites, 3.1% involved 1 reported stenosis at non-LVO finding sites, 3.1% involved 2 reported stenosis at non-LVO finding sites, 12.5% involved 3 reported stenosis at non-LVO finding sites, 3.1% involved 4 reported stenosis at non-LVO finding sites, 3.1% involved 5 reported stenosis at non-LVO finding sites, and 6.2% involved 6 reported stenosis at non-LVO finding sites.

Now, consider FIG. 5B, which shows results associated with the binary classification model 302 when the architecture 400*b* is implemented. As mentioned above, various embodiments of the invention were tested/validated on 3584 studies, and such 3584 studies were obtained from two different data sources (e.g., two different hospital environments). These two different data sources are indicated as MGH and BWH in FIG. 5B. Specifically, 3036 studies (e.g., about 85%) came from MGH, where 47% were LVO-positive, and 548 studies (e.g., about 15%) can from BWH, where 35% were LVO-positive. As shown, FIG. 5B depicts the results for each data source individually, as well as the overall results for the data sources combined. As shown, various embodiments of the binary classification model 302 implementing the architecture 400*b* achieved an overall accuracy of 90%, an overall sensitivity of 93%, an overall specificity of 87.2%, and an overall AUC of 0.969.

Figure 6:
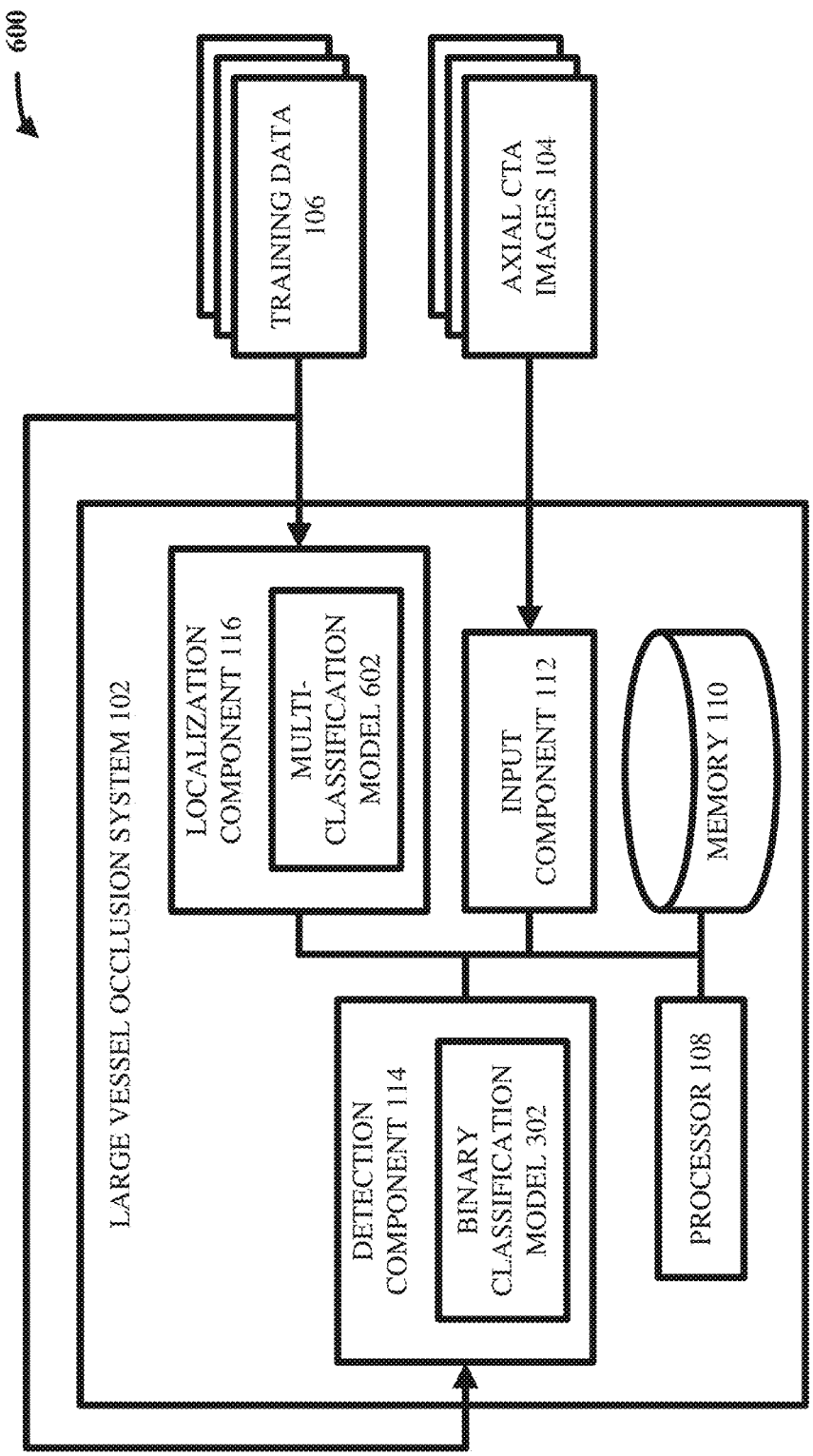
FIG. 6 illustrates a block diagram of an example, non-limiting system including a multi-classification model that facilitates automated localization of large vessel occlusions in accordance with one or more embodiments described herein.

FIG. 6 illustrates a block diagram of an example, non-limiting system 600 including a multi-classification model that can facilitate automated localization of large vessel occlusions in accordance with one or more embodiments described herein. The system 600 can, in various embodiments, comprise the same components as the system 300, and can further comprise a multi-classification model 602.

In various instances, the multi-classification model 602 can be a three-dimensional convolutional neural network including residual bottleneck blocks that can receive as input the axial CTA images 104 and output a polychotomous scalar result (e.g., indicating laterality and/or occlusion site of a detected LVO). In various aspects, as mentioned above, a plurality of scalar outputs can be generated by the multi-classification model 602, each scalar output representing a different aspect/characteristic of the detected LVO, and/or each scalar output binarily representing the presence/absence of an LVO at various locations of interest. In various instances, the multi-classification model 602 can be any suitable machine learning, deep learning, and/or pattern recognition model known in the art that can be trained (e.g., supervised learning, unsupervised learning, reinforcement learning, and so on) to classify images (e.g., neural networks, support vector machines, logistic regression, and so on).

In various embodiments, much of the above description of artificial intelligence and neural network architectures (e.g., as in FIGS. 4A-4B) can be applied to the multi-classification model 602. That is, in various instances, the multi-classification model 602 can be a 3D convolutional neural network having residual bottleneck blocks, the multi-classification model 602 can be a 3D convolutional neural network having dense blocks, the multi-classification model 602 can be an ensemble of sub-models, each having different architectures and/or hyperparameters from each other, and so on.

Figure 7A:
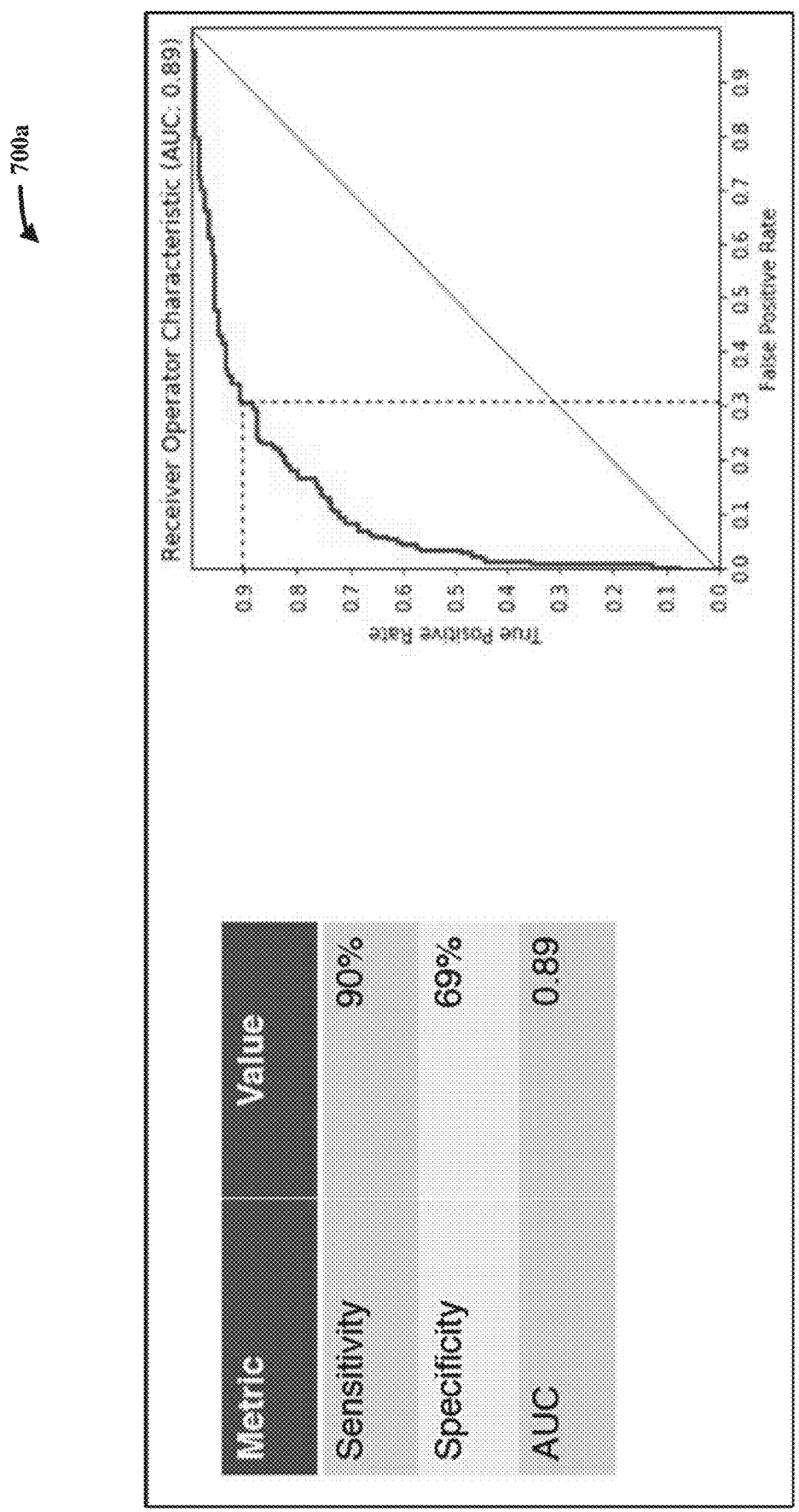
Figure 7B:
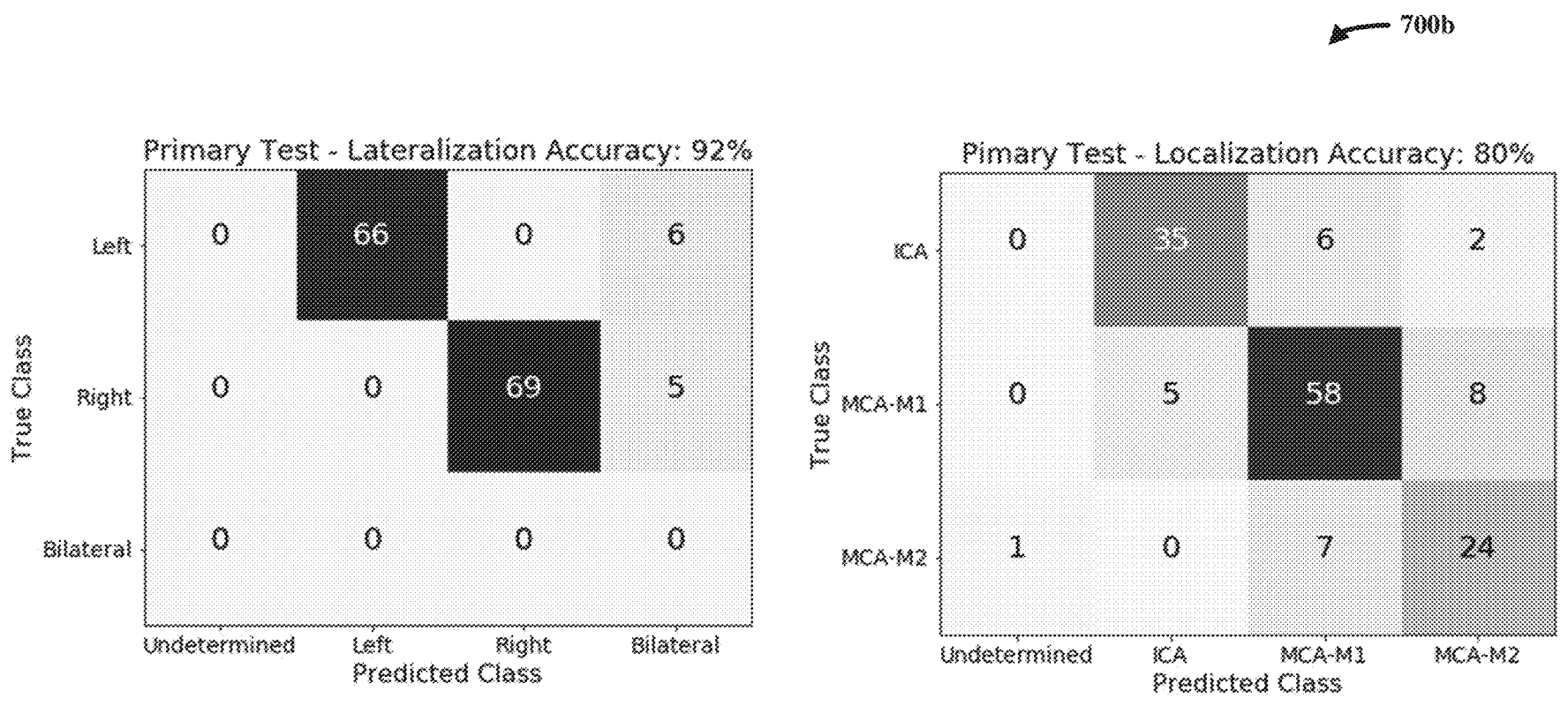

FIGS. 7A-7B illustrate exemplary, non-limiting experimentation results of a multi-classification model that can facilitate automated localization of large vessel occlusions in accordance with one or more embodiments described herein. Experiments regarding the multi-classification model 602 performed by the inventors of the subject innovation yielded results as depicted in FIGS. 7A-7B.

First, consider FIG. 7A, which shows results associated with the multi-classification model 602 when the architecture 400a is implemented As shown in the results, a fully trained embodiment of the multi-classification model 602, which was trained, validated, and tested on the dataset described above, yielded a sensitivity (e.g., true positive rate) of 90%, a specificity (e.g., true negative rate) of 69%, and an AUC of 0.89. Specifically, an embodiment of the multi-classification model 602 was tested on a test set consisting of 352 random samples, with 154 positive samples and 198 negative samples. The multi-classification model 602 correctly classified 139 of the 154 positive samples and 137 of the 198 negative samples. This particular embodiment of the multi-classification model 602 thus had 15 false negative results and 61 false positive results. This embodiment of the multi-classification model 602 misclassified the laterality of 11 LVOs (e.g., the model was correct about the presence of an LVO, but was incorrect about the laterality) and misclassified the occlusion site of 10 LVOs (e.g., the model was correct about the laterality, but incorrect as to the segment of the vascular tree that was occluded). Note that some of this data included multiple LVOs in multiple occlusion sites. Of the true positive findings, 5.8% were located in the ICA, 35.3% were located in an M2 segment of the MCA, 14.4% were located in an M1 segment of the MCA, 16.5% were located in both the M1 and M2 segments of the MCA, and 28.1% were located in both the ICA and the MCA. Of the false negative findings, 33.3% were in the ICA, 40.0%% were in the M2 segment of the MCA, 6.7% were in the M1 segment of the MCA, 6.7% were in both the M1 and M2 segments of the MCA, and 13.3% were in both the ICA and the MCA. Of the true positive results, 50.4% exhibited right laterality, and 49.6% exhibited left laterality. Of the false negative results, 53.3% exhibited left laterality, and 46.7% exhibited right laterality. Of the true positive results, 36.7% exhibit equivocal collaterals, 38.8% exhibited normal collaterals, and 24.5% exhibited low collaterals. Of the false negative results, 20.0% exhibited equivocal collaterals, 73.3% exhibited normal collaterals, and 6.7% exhibited low collaterals. Of the true negative results, 92.0% involved 0 reported occlusions at non-LVO finding sites (e.g., distal M2, M3, A1, P1, Basilar, Vertebral), 5.1% involved 1 reported occlusion at non-LVO finding sites, 2.2% involved 2 reported occlusions at non-LVO finding sites, and 0.7% involved 3 reported occlusions at non-LVO finding sites. Of the false positive results, 82.0% involved 0 reported occlusions at non-LVO finding sites, 14.8% involved 1 reported occlusion at non-LVO finding sites, and 3.3% involved 2 reported occlusions at non-LVO finding sites. Of the true negative results, 94.9% involved 0 reported stenosis at non-LVO finding sites, 2.2% involved 1 reported stenosis at non-LVO finding sites, about 1.3% involved 2 reported stenosis at non-LVO finding sites, about 0.9% involved 3 reported stenosis at non-LVO finding sites, and about 0.7% involved 4 reported stenosis at non-LVO finding sites. Of the false positive results, 82.0% involved 0 reported stenosis at non-LVO finding sites, 3.3% involved 1 reported stenosis at non-LVO finding sites, 1.6% involved 2 reported stenosis at non-LVO finding sites, 8.2% involved 3 reported stenosis at non-LVO finding sites, 1.6% involved 5 reported stenosis at non-LVO finding sites, and 3.3% involved 6 reported stenosis at non-LVO finding sites.

Now, consider FIG. 7B, which shows results associated with the multi-classification model 602 when the architecture 400b is implemented. As mentioned above, various embodiments of the invention were tested/validated on 3584 studies, and such 3584 studies were obtained from two different data sources, denoted as MGH and BWH in FIG. 7B. As shown, FIG. 7B depicts the results for each data source individually, as well as the overall results for the data sources combined. As shown, various embodiments of the multi-classification model 602 implementing the architecture 400b achieved an overall lateralization accuracy of 92% (e.g., misclassified 6 out of 72 true left-laterality LVOs as bilateral LVOs, misclassified 5 out of 74 true right-laterality LVOs as bilateral LVOs) and achieved an overall localization accuracy of 80% (e.g., misclassified 6 out of 43 true ICA LVOs as MCA-M1 LVOs, misclassified 2 out of 43 true ICA LVOs as MCA-M2 LVOs, misclassified 5 out of 71 true MCA-M1 LVOs as ICA LVOs, misclassified 8 out of 71 true MCA-M1 LVOs as MCA-M2 LVOs, and misclassified 7 out of 31 true MCA-M2 LVOs as MCA-M1 LVOs).

Although not explicitly shown in the figures, some embodiments of the subject innovation can combine the binary classification model 302 and the multi-classification model 602 into one end-to-end, ensembled model. In various aspects, such an ensemble can include any suitable number of models (e.g., five models) that can receive as input an overall LVO study. In various aspects, the overall LVO study can contain both right laterality studies and left laterality studies (e.g., can include images of a right-half of a patient's brain and separate images of a left-half of a patient's brain). Each model in the ensemble can be structured as described above (e.g., with respect to FIGS. 4A-4B). In various aspects, the results of the ensemble can be analyzed in three steps: a binary detection step, a lateralization step, and a localization step.

In various instances, in the binary detection step, each model in the ensemble can run on each laterality study, and each model in the ensemble can produce as output a scalar value for each laterality study, which can indicate the probability (as determined by that particular model) that that particular laterality study contains an LVO. For example, if five models are included in the ensemble, then there can be a total of 10 of such scalar values (e.g., each model in the ensemble can generate two scalar values, one for the right laterality study and another for the left laterality study). If a scalar value is above any suitable predetermined threshold, then the scalar value can be considered as indicating the presence of an LVO in the given laterality study. On the other hand, if the scalar value is below the predetermined threshold, the scalar value can be considered as indicating the absence of an LVO in the given laterality study. In various aspects, for each model in the ensemble, a maximum scalar value can be obtained by taking the higher of the two scalar values generated for the two laterality studies (e.g., if a model in the ensemble generates a value of 0.64 for a right laterality study and a value of 0.56 for a left laterality study, then the value 0.64 can be taken as the maximum scalar value generated by that model for the overall LVO study). In various cases, a majority vote can then be applied to the maximum scalar values generated by the models of the ensemble to arrive at a binary classification for the overall LVO study (e.g., if a majority of the maximum scalar values generated by the models in the ensemble exceed the predetermined threshold, the overall LVO study can be determined to have an LVO. Otherwise, the overall LVO study can be determined to not have an LVO.

In various instances, in the lateralization step, the LVO-positive studies from the binary detection step can be considered. Specifically, each laterality study can be considered separately to determine how many models in the ensemble concluded that that laterality is positive for an LVO (e.g., if the scalar generated by a model for a right laterality study is above a predetermined threshold, that model can be considered as having concluded that the right laterality is LVO-positive). If a majority of the models determine that a given laterality has an LVO, then that laterality can be considered as LVO-positive. In some cases, the predetermined threshold applied in the lateralization step can be lower than the predetermined threshold applied during the binary detection step, which can help to reduce a number of false positives for binary detection.

In various aspects, in the localization step, LVO-positive laterality studies from the lateralization step can be considered. For each positive model in the lateralization step, probabilities can be assigned to any four classes (e.g., ICA, M1, M2, undetermined). However, in various aspects, any suitable number of classes can be implemented. That is, as mentioned above, each model in the ensemble can be configured to generate not only a scalar value binarily indicating presence or absence of an LVO, but can also generate scalar values that assign probabilities to different LVO localizations. In such cases, each model can predict the localization that has the highest probability (e.g., if a model predicts that a left laterality study is 40% likely to have an ICA LVO, 30% likely to have an MCA-M1 LVO, 10% likely to have an MCA-M2 LVO, and 20% unsure, then the model can be considered as determining that an ICA LVO is present). That is, each model in the ensemble can predict a particular localization, and then a majority vote can be taken among all the models in the ensemble. In such case, the localization with the most votes can win. In some cases, ties can be broken in the any suitable order of priority (e.g., undetermined takes priority over ICA, which takes priority over MCA-M1, which takes priority over MCA-M2).

Such an ensemble of models can be summarized as follows. The ensemble can contain any suitable number of models having any suitable structures and/or hyperparameters as mentioned above. Each model can be configured to receive as input a left-laterality study and a right-laterality study, to generate for each laterality study a first scalar value binarily indicating LVO presence or absence, and to assign for each laterality study probabilities and/or likelihoods for each possible localization (e.g., ICA, M1, M2, undetermined). The first scalar values generated by the ensemble can then be analyzed to determine whether or not the overall LVO study includes an LVO. Such analysis can include: (1) choosing for each model the maximum scalar value generated between the left-laterality study and the right-laterality study; (2) counting how many of the maximum scalar values exceed a predetermined threshold; and (3) determining that an LVO is present in the overall LVO study if a majority of the maximum scalar values exceed the predetermined threshold. If the overall LVO study is determined to have an LVO, the probabilities and/or likelihoods generated by the ensemble can then be analyzed to determine a laterality and/or localization for the overall LVO study. Such analysis can include: (1) considering overall LVO studies that were binarily determined to have an LVO present; (2) for each laterality and for each model in the ensemble, checking whether the model's scalar value for that laterality exceeds a predetermined threshold (e.g., can be lower than the binary predetermined threshold); (3) for each laterality, performing a majority vote to determine whether a majority of the models determined that the laterality is LVO-positive; (4) for each laterality that is LVO-positive and for each model in the ensemble, determining to which localization the model assigned a highest probability/likelihood; and (5) performing a majority vote of such maximum localization probabilities to determine an LVO localization for the overall LVO study.

Figure 8:
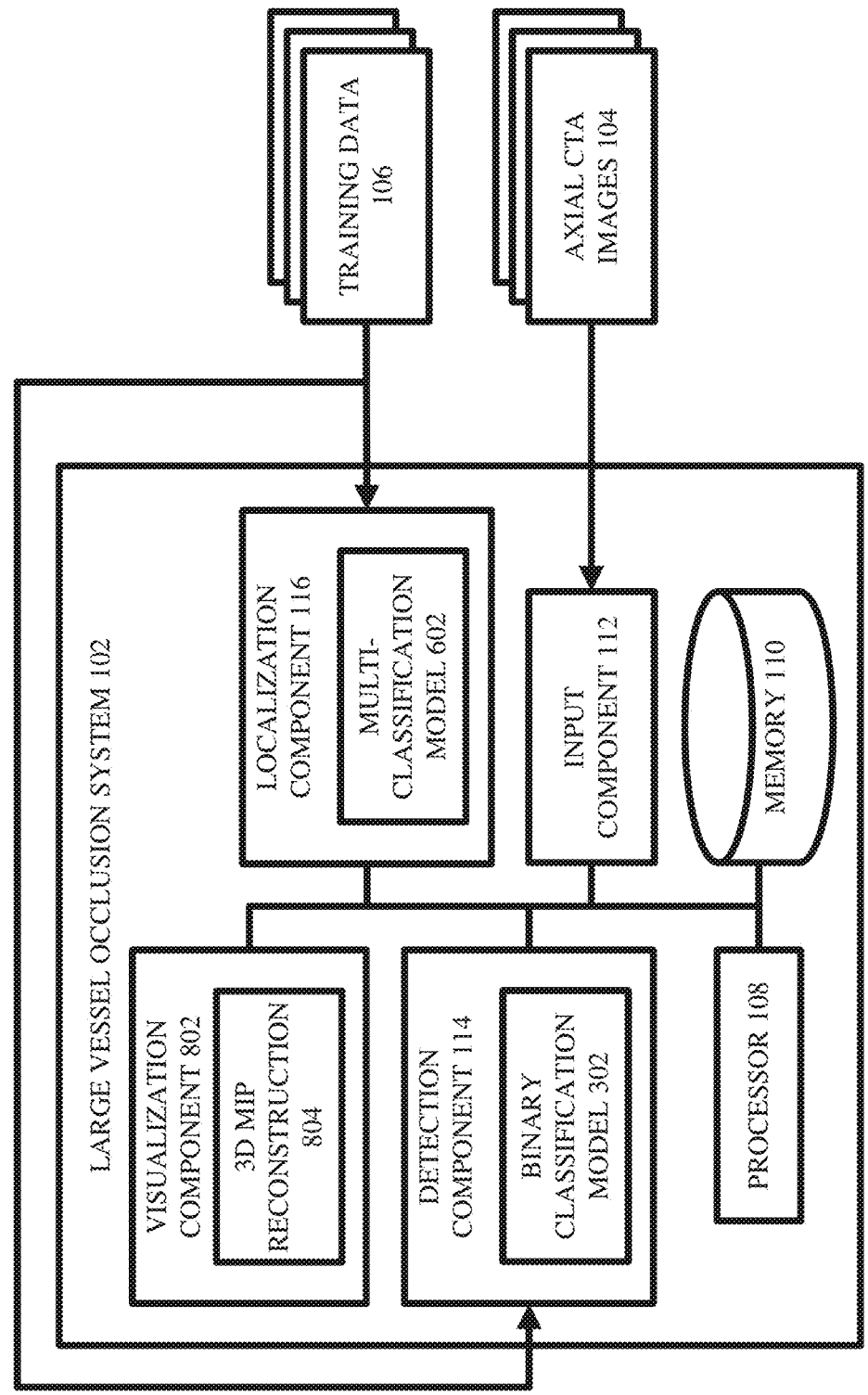
FIG. 8 illustrates a block diagram of an example, non-limiting system including a visualization component that facilitates automated localization of large vessel occlusions in accordance with one or more embodiments described herein.

FIG. 8 illustrates a block diagram of an example, non-limiting system 800 including a visualization component that can facilitate automated localization of large vessel occlusions in accordance with one or more embodiments described herein. The system 800 can, in various embodiments, comprise the same components as the system 600, and can further comprise a visualization component 802.

In various embodiments, the visualization component 802 can automatically generate a three-dimensional MIP reconstruction (e.g., the 3D MIP reconstruction 804) of the vascular tree of the patient's brain, based on the axial CTA images 104. In other words, the visualization component 802 can generate a three-dimensional graphical representation that visually depicts the patient's cerebral vascular tree in three-space, by stitching together the two-dimensional slices represented by the axial CTA images 104 (e.g., similar to constructing an entire loaf of bread by lining up in order the individual slices of the loaf of bread). In various embodiments, each image in the axial CTA images 104 can represent a 1 mm thickness of the patient's brain along an axial/spinal direction. Thus, in various embodiments, the visualization component 802 can generated the 3D MIP reconstruction 804 by stitching together and/or concatenating these individual 1 mm slices. In various other embodiments, the visualization component 802 can improve a signal-to-noise ratio of the 3D MIP reconstruction 804 by averaging the 1 mm slices into 5 mm slices (e.g., converting every five, consecutive, 1 mm CTA images in the axial CTA images 104 into a single, corresponding CTA image that contains the average pixel values of the original five images), and then stitching together those 5 mm slices into the 3D MIP reconstruction 804. In various embodiments, any suitable mathematical and/or statistical technique for generating a three-dimensional MIP volume based on a series of two-dimensional CTA images can be implemented.

In various embodiments, the visualization component 802 can display the 3D MIP reconstruction 804 to the user. For instance, the visualization component 802 can be communicatively coupled, via a wired and/or wireless connection, to a computer monitor (e.g., and/or to any other type of computerized display device, such as a mobile phone, a laptop, a PDA, a television screen, a projector, and so on). In various embodiments, the visualization component 802 can display any suitable and/or desired two-dimensional projection of the 3D MIP reconstruction 804 to the user (e.g., displaying any suitable x-y projection, any suitable y-z projection, any suitable x-z projection, a projection onto any other suitable and/or desired plane and/or surface, and so on). In some embodiments, the visualization component 802 can display an animation of the 3D MIP reconstruction (e.g., a rapid succession of two-dimensional projections to give the illusion of motion, and so on). For instance, the visualization component 802 can display the 3D MIP reconstruction 804 as rotating about a desired axis. In various aspects, the visualization component 802 can include a user interface that allows the user to select which two-dimensional projection of the 3D MIP reconstruction 804 the user would like to see and/or which animation the user desires. In various embodiments, any other suitable and/or desired way of visually displaying the 3D MIP reconstruction 804 to the user can be implemented.

In various instances, the 3D MIP reconstruction 804 can be leveraged by the user to manually visually verify the localization results generated by the localization component 116. For instance, the localization component 116 can determine/infer that an LVO is located at a proximal M2 segment in a right MCA of the patient's brain. The visualization component 802 can accordingly generate and display to the user (e.g., attending medical professional) the 3D MIP reconstruction 804 of the patient's brain. If the user so desires, the user can visually and manually evaluate the 3D MIP reconstruction 804 and determine for himself/herself whether he/she agrees with the determination/inference made by the localization component 116. This can be beneficial since it allows the user to easily and conveniently double-check the work of the LVO system 102 if the user believes such would be necessary and/or beneficial (e.g., to verify that the LVO system 102 is functioning appropriately, to provide a redundant safety check, and so on). Since the user can, in various embodiments, request any suitable and/or desired projection of the patient's brain from the 3D MIP reconstruction 804, the user can evaluate different views as desired of the purportedly localized LVO, thereby enhancing the user's manual evaluation. Being able to request any desired view/projection can improve the user's ability to manually determine whether an LVO is detected as well as to manually evaluate the status of collateral circulation in the patient's brain.

In various embodiments, the visualization component 802 can highlight and/or otherwise visually emphasize the localized LVO in the 3D MIP reconstruction 804 (e.g., and/or in two-dimensional projections of the 3D MIP reconstruction 804). For instance, the visualization component 802 can visually designate the purportedly localized LVO with a symbol (e.g., a circle, an arrow, a star, an asterisk, any/other desired shape, and so on). For example, if the localization component 116 infers/determines that an LVO is located at an M2 segment of a left MCA, the visualization component 802 can generate the 3D MIP reconstruction 804 and can accordingly encircle the M2 segment of the left MCA in any projection called by the user, such that the M2 segment of the left MCA visually stands out from the rest of the projection, which can result in the user more easily and quickly visually finding the M2 segment of the left MCA. As another example, the visualization component 802 can visually designate the purportedly localized LVO with a color (e.g., highlighting in red, yellow, orange, and/or any suitable/desired color the pixels/voxels that correspond to the localized LVO). So, if the localization component 116 determines/infers that an LVO is located at a right PCA, the visualization component 802 can generate the 3D MIP reconstruction 804 and accordingly highlight and/or otherwise visually designate via color the right PCA in any projection called by the user, such that the right PCA visually stands out from the rest of the projection, which can result in the user more quickly and easily visually finding the right PCA. Such highlighting and/or visual emphasis can help prevent the user from wasting time looking at irrelevant portions of the displayed projection.

As described above, in some embodiments, the subject innovation can analyze the axial CTA images 104 (or the manual MIP reconstructions 118) in order to detect/localize LVOs in a patient and can generate the 3D MIP reconstruction 804 based on the axial CTA images 104. However, in various embodiments, the subject innovation can generate the 3D MIP reconstruction 804 based on the axial CTA images 104 and can analyze the 3D MIP reconstruction 804 (e.g., via the detection component 114 and/or the localization component 116) in order to detect/localize LVOs in the patient. In such embodiments, the visualization component 802 can receive the axial CTA images 104 from the input component 112 and can accordingly generate the 3D MIP reconstruction 804. In such embodiments, the detection component 114 and/or the localization component 116 can then receive and analyze the 3D MIP reconstruction 804 (and/or any suitable/desired two-dimensional projections of the 3D MIP reconstruction 804), rather than receiving and analyzing the axial CTA images 104 (e.g., analyzing the automatically generated 3D MIP reconstruction 804 rather than analyzing raw CTA thin images directly, analyzing the automatically generated 3D MIP reconstruction 804 rather than analyzing manually created MIP reconstructions, and so on). In various experiments, the inventors of the subject innovation found that analyzing (e.g., via the binary classification model 302 and/or the multi-classification model 602) projections of the 3D MIP reconstruction 804 can yield more consistent detection/localization results as compared to analyzing the axial CTA images 104. That is, in various cases, performance benefits can be achieved by first generating the 3D MIP reconstruction 804 based on the axial CTA images 104 and then localizing LVOs by analyzing the 3D MIP reconstruction 804.

In various embodiments, the subject innovation can generate MIPs and/or localize LVOs based on intermediate thin slices, where intermediate thin slices can be modified/altered CTA images derived from the axial CTA images 104 (e.g., where the intermediate thin slices are registered, aligned, zoomed in/out, rotated, combined/concatenated, averaged, and/or otherwise suitably altered versions of the axial CTA images 104). In such cases, the input component 112 can generate such intermediate thin slices by modifying/altering the axial CTA images 104 as desired.

Figure 9:
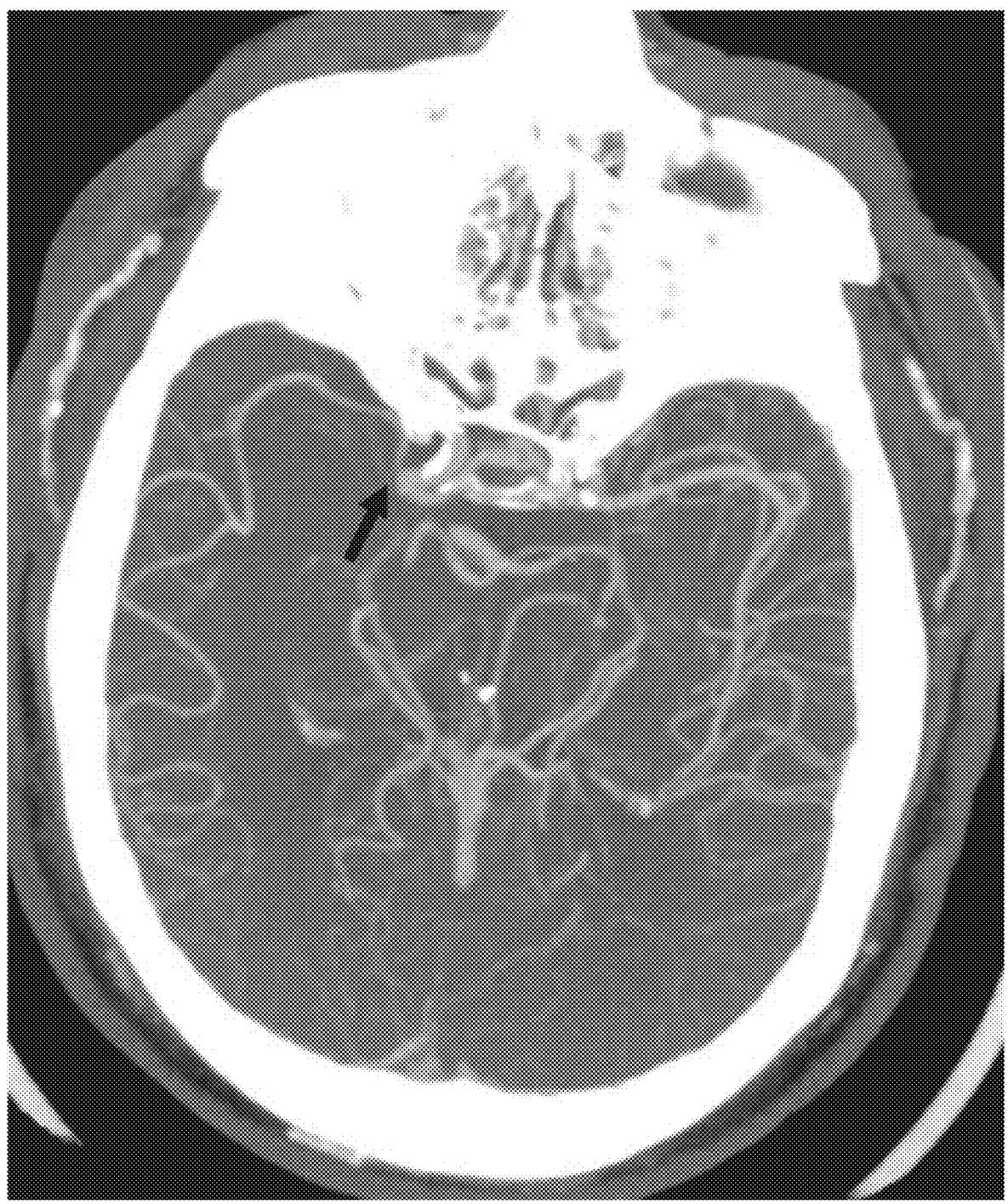
FIGS. 9-11 illustrate exemplary, non-limiting visualizations of localized LVOs in accordance with one or more embodiments described herein.
Figure 10:
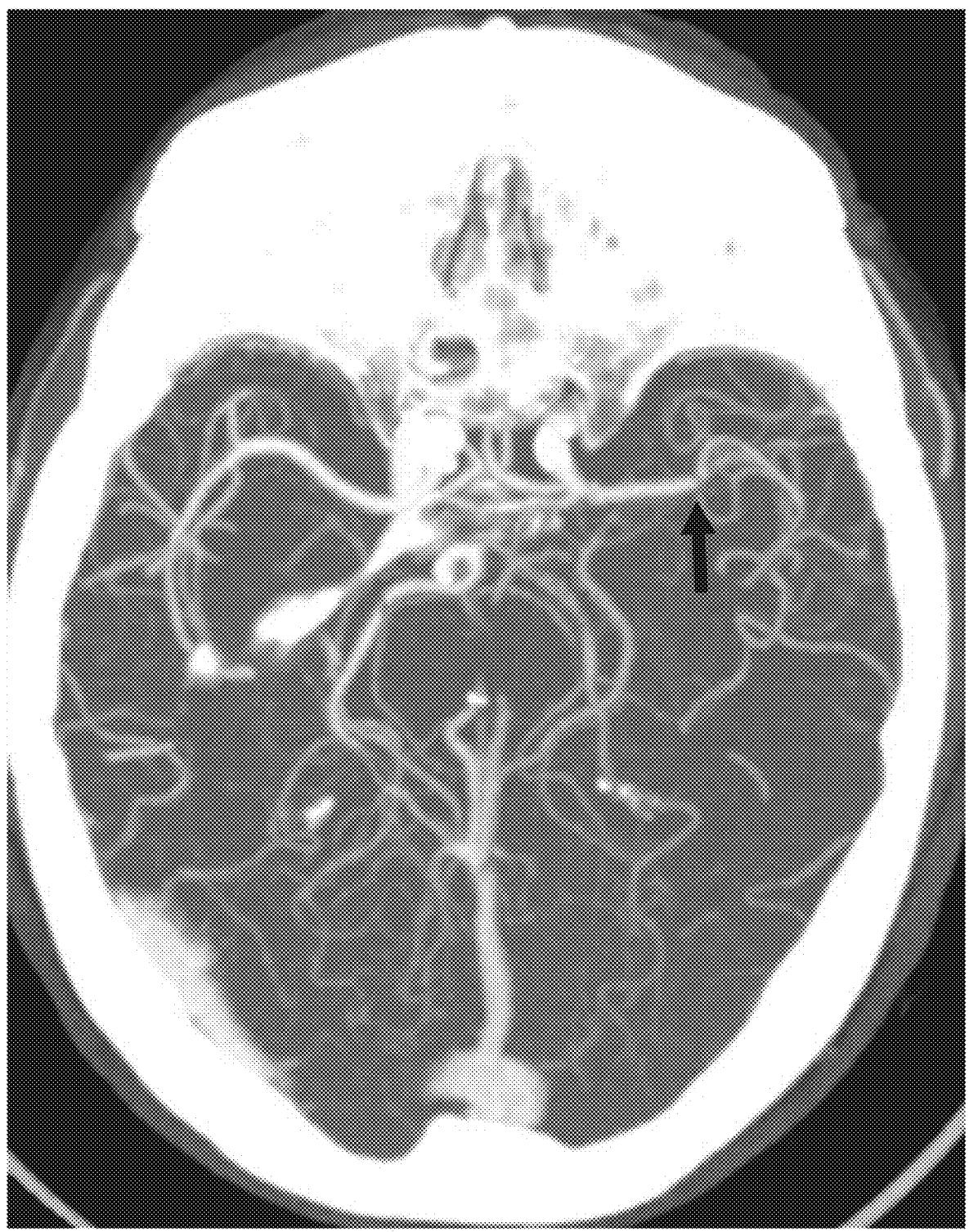
Figure 11:

FIGS. 9-11 illustrate exemplary, non-limiting visualizations of localized LVOs in accordance with one or more embodiments described herein.

FIG. 9 depicts an exemplary, non-limiting projection (e.g., x-y projection, with the z-axis parallel to the patient's spine) of a right M1 occlusion distal to an early branching anterior temporal. In various cases, the image in FIG. 9 can be generated by the visualization component 802 and displayed to the user so that the user can manually evaluate the patient's vascular tree to determine whether he or she agrees with the determination of the localization component 116. In various cases, the visualization component 802 can visually emphasize the localized LVO by circling it (not shown), pointing toward it with an arrow (shown), highlighting it with an eye-catching color (not shown), and so on. This can allow the user to quickly and easily visually perceive the vascular segment of interest. In various embodiments, any suitable technique for visually emphasizing the localized LVOs such that they are more easily and quickly perceived by the user can be implemented (e.g., circumscribing the LVO with any desired shape, highlighting/coloring the LVO with any desired color, pointing toward the LVO with any desired marking, and so on). FIG. 10 depicts a similar projection of a left M2 occlusion (e.g., again, visually emphasized with an arrow for ease of visual acquisition). FIG. 11 depicts a similar projection of a right distal ICA occlusion with some reconstitution (e.g., again, visually emphasized with an arrow).

Figure 12:
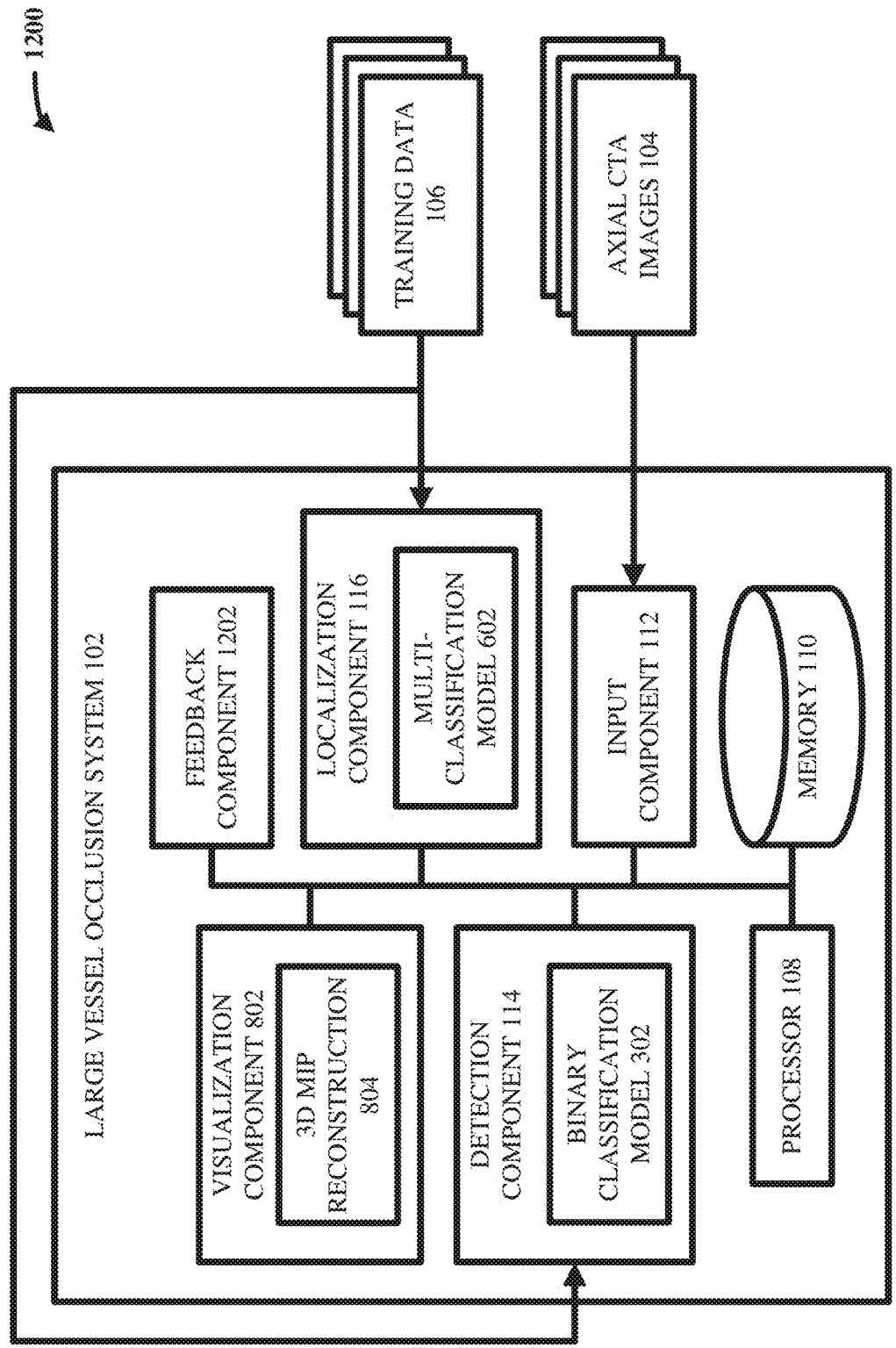
FIG. 12 illustrates a block diagram of an example, non-limiting system including a feedback component that facilitates automated localization of large vessel occlusions in accordance with one or more embodiments described herein.

FIG. 12 illustrates a block diagram of an example, non-limiting system 1200 including a feedback component that can facilitate automated localization of large vessel occlusions in accordance with one or more embodiments described herein. System 1200 can, in various embodiments, comprise the same components as the system 800, and can further comprise a feedback component 1202.

In various embodiments, the feedback component 1202 can be communicatively coupled, via a wired and/or wireless connection, to any suitable interface device to allow the user to provide substantially real-time feedback to the LVO system 102 during deployment of the LVO system 102. In various aspects, the feedback component 1202 can receive the user feedback and can accordingly modify/update the binary classification model 302 and/or the multi-classification model 602. That is, the visualization component 802 can generate the 3D MIP reconstruction 804 so that the user can manually verify the localization determination produced by the localization component 116. If desired, the user can provide feedback to the LVO system 102 via the feedback component 1202 (e.g., the user can indicate agreement and/or disagreement with the LVO determination of the localization component 116 by interacting with the feedback component 1202 via a keyboard, buttons, a touchscreen, voice recognition, and so on). In various cases, if the user disagrees with the determination of the localization component 116 (and/or with the detection component 114), the user can indicate a correct label/classification/localization for the patient in question (e.g., for the axial CTA images 104 that served as input for the LVO system 102). Based on this feedback, the feedback component 1202 can cause and/or initiate a recalibration of the parameters, weights, and/or biases of the binary classification model 302 and/or the multi-classification model 602 (e.g., via backpropagation, stochastic gradient descent, and so on). In this way, the LVO system 102 can continually learn in real-time from subject matter experts (e.g., from attending medical professionals). In other words, the feedback component 1202 can facilitate on-going supervised learning of the LVO system 102, even when the LVO system 102 is deployed in a real-world hospital setting.

Figure 13:
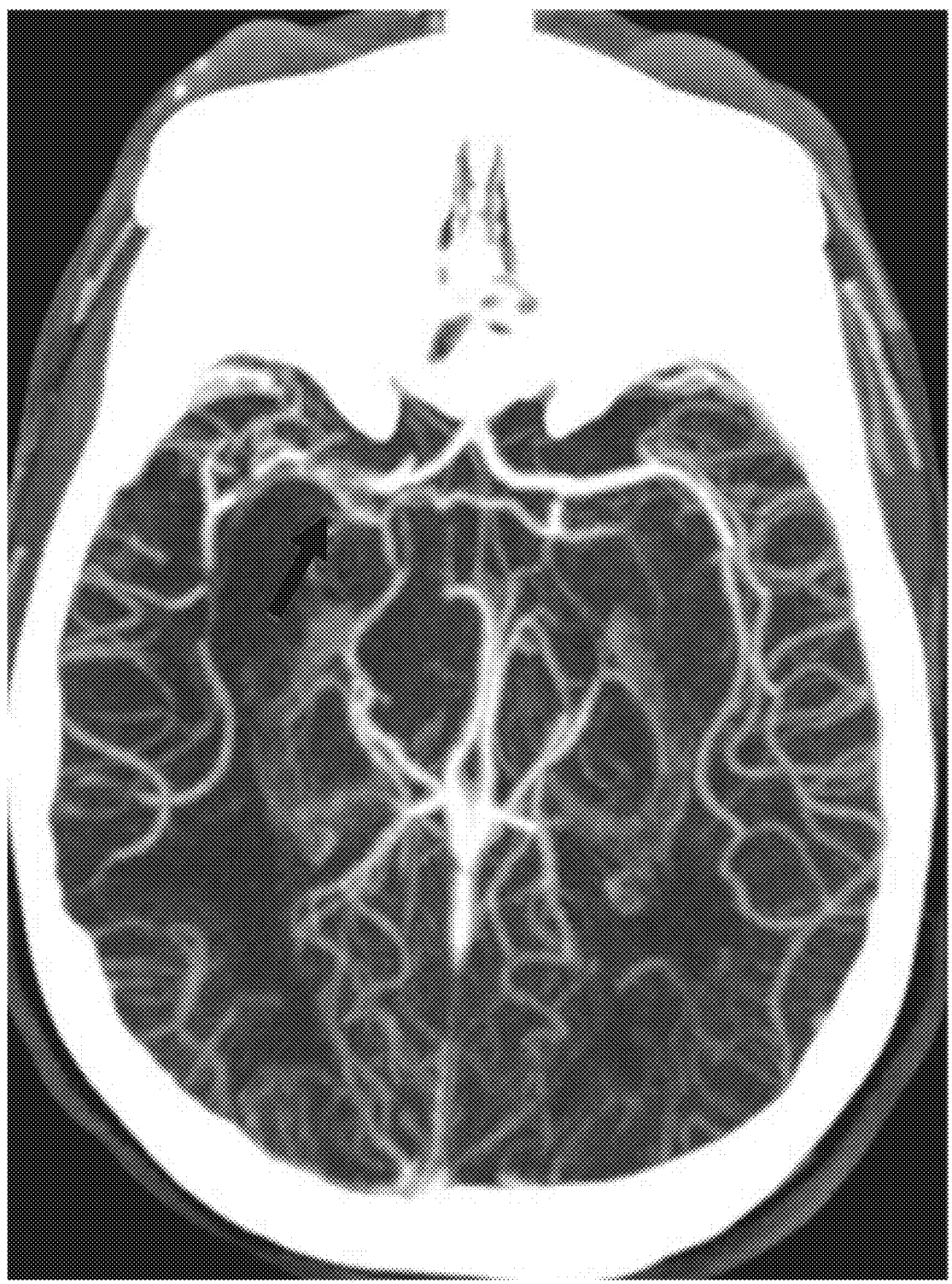
FIGS. 13-15 illustrate exemplary, non-limiting feedback from users regarding LVO localizations in accordance with one or more embodiments described herein.
Figure 14:
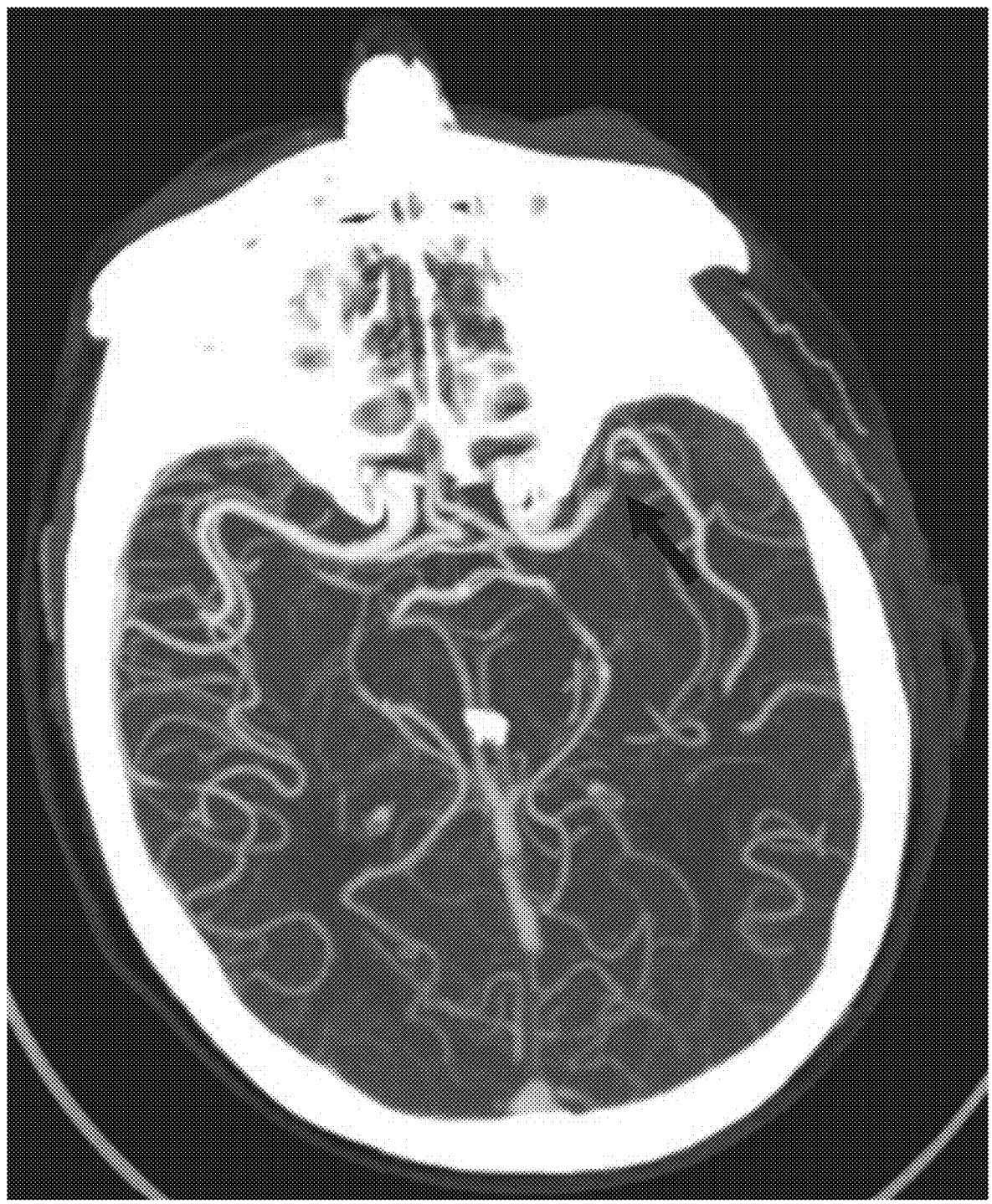
Figure 15:
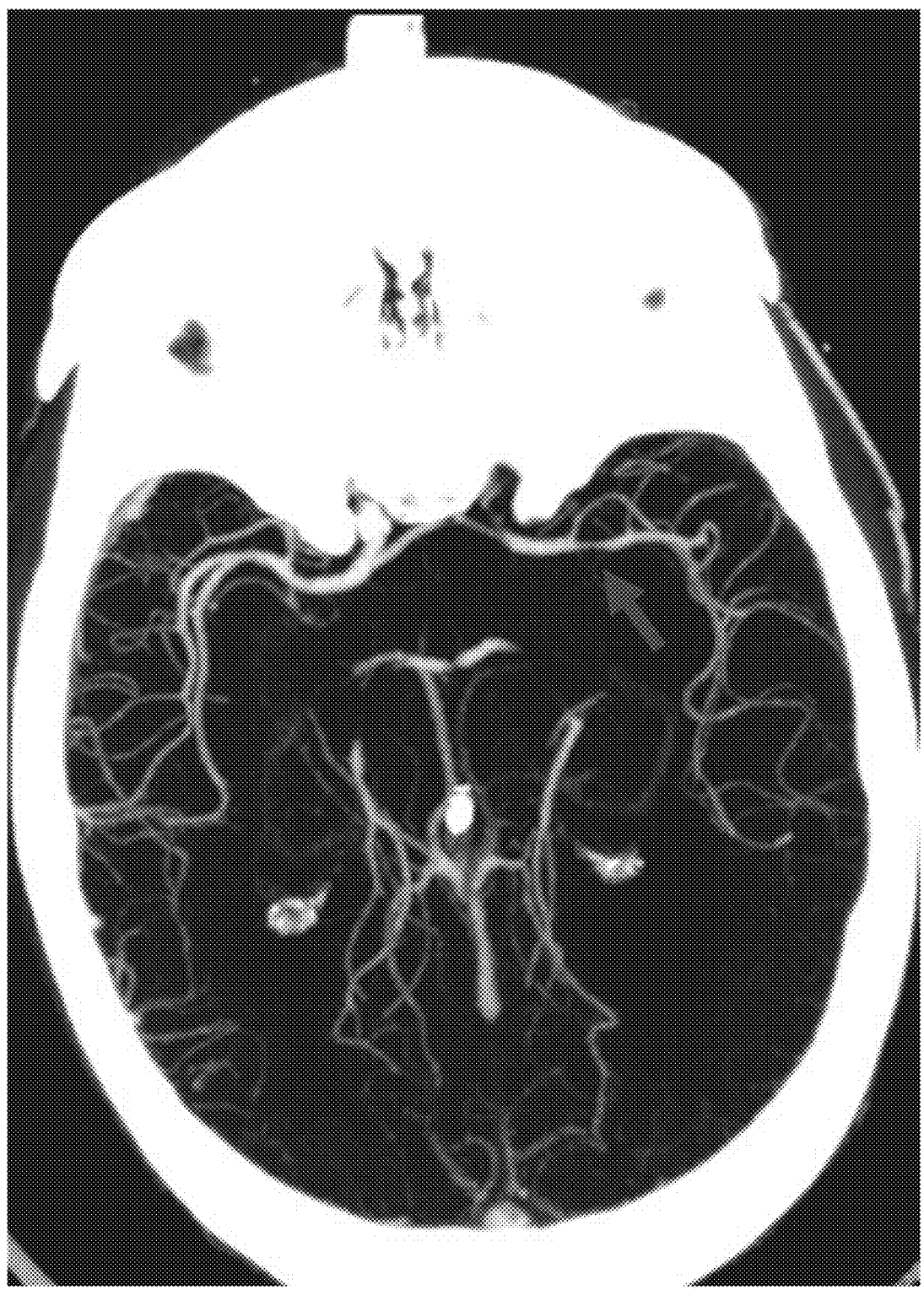

FIGS. 13-15 illustrate exemplary, non-limiting feedback from users regarding LVO localizations in accordance with one or more embodiments described herein. Note that the images depicted in FIGS. 13-15 can be CTA images that an implementation of the LVO system 102 incorrectly classified/localized (e.g., due to training and/or difficulty of diagnosis). Thus, any arrows added to FIGS. 13-15 are included solely for reader convenience and comprehension; any incorrect visual emphasis and/or overlays added by the visualization component 802 have been removed for ease of comprehension.

Specifically, FIG. 13 depicts an image of a nearly occlusive thrombus in the right M1 segment, denoted by the arrow. An embodiment of the LVO system 102 incorrectly labeled this an LVO of the right M1. In such case, the user can utilize the feedback component 1202 to indicate the proper label for this input image (e.g., no LVO detected). Similarly, FIG. 14 depicts an image of a near-occlusive filling defect within the distal left M1 segment. An embodiment of the LVO system 102 incorrectly labeled this an LVO of the left M1. In such case, the user can utilize the feedback component 1202 to indicate the proper label for this input image (e.g., no LVO detected). Similarly, FIG. 15 depicts an image of an interval recanalization of previous left M1 occlusion where segmental severe stenosis persists. An embodiment of the LVO system 102 incorrectly labeled this an LVO of the left M1. In such case, the user can utilize the feedback component 1202 to indicate the proper label for this input image (e.g., no LVO detected). Based on this feedback (e.g., based on these correct labels), the feedback component 1202 can facilitate an update and/or recalibration (e.g., backpropagation, gradient descent, and so on) of the multi-classification model 602 (and/or the binary classification model 302, as appropriate). Any suitable feedback (e.g., correct label) can be provided to the LVO system 102 by the user via the feedback component 1202. This can include correcting false positives caused by apparent occlusion (e.g., extensive intracranial atherosclerosis including apparent occlusion of an M2 vessel of the right MCA (proximal to the infarct) occlusion versus critical multifocal stenosis of the right PCA), false positives caused by multifocal severe stenosis and/or vasospasm, false negatives caused by calcific embolus, and so on.

Figure 16:
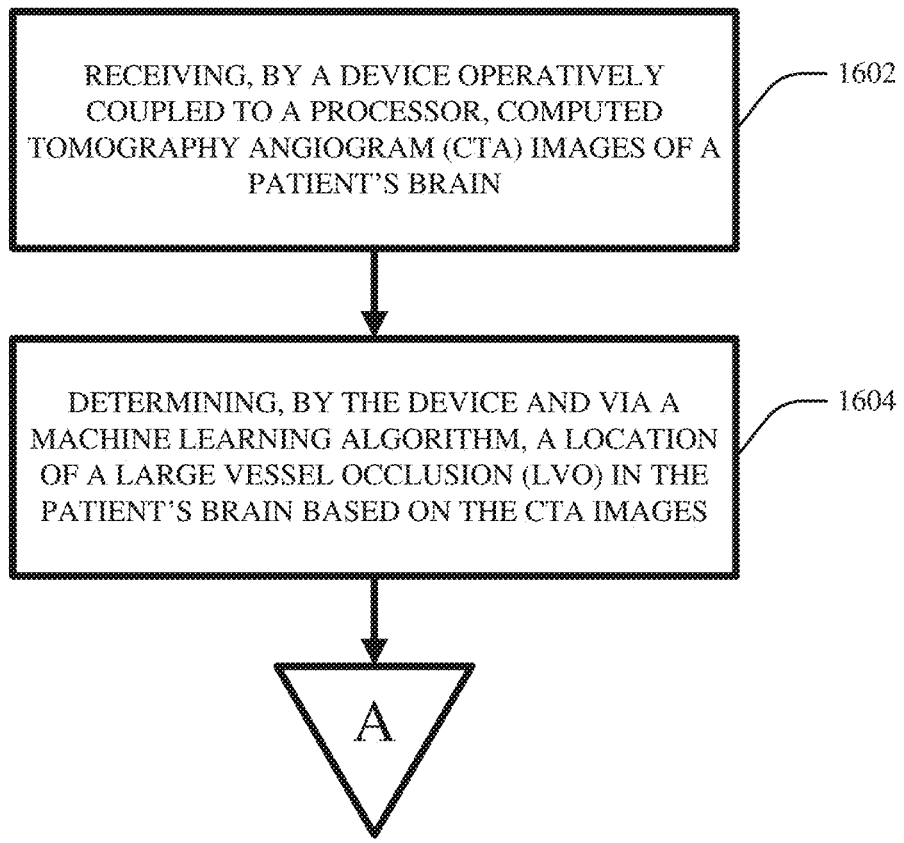
FIG. 16 illustrates a flow diagram of an example, non-limiting computer-implemented method that facilitates automated localization of large vessel occlusions in accordance with one or more embodiments described herein.

FIG. 16 illustrates a flow diagram of an example, non-limiting computer-implemented method 1600 that can facilitate automated localization of large vessel occlusions in accordance with one or more embodiments described herein.

In various embodiments, act 1602 can include receiving, by a device operatively coupled to a processor (e.g., input component 112), computed tomography angiogram (CTA) images (e.g., axial CTA images 104) of a patient's brain.

In various instances, act 1604 can include determining, by the device (e.g., localization component 116) and via a machine learning algorithm (e.g., multi-classification model 602), a location of a large vessel occlusion (LVO) in the patient's brain based on the CTA images.

Figure 17:
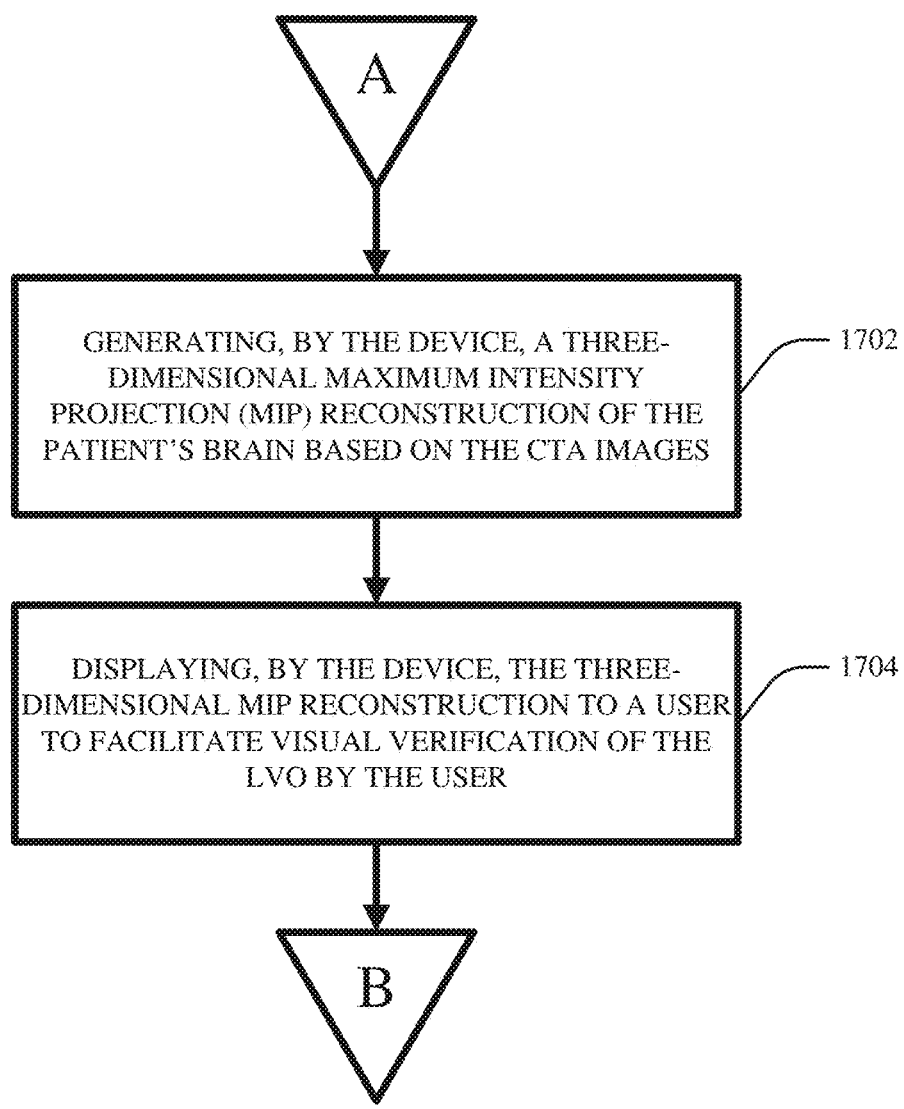
FIG. 17 illustrates a flow diagram of an example, non-limiting computer-implemented method including generating and displaying visualizations that facilitates automated localization of large vessel occlusions in accordance with one or more embodiments described herein.

FIG. 17 illustrates a flow diagram of an example, non-limiting computer-implemented method 1700 including generating and displaying visualizations that can facilitate automated localization of large vessel occlusions in accordance with one or more embodiments described herein. As shown, the computer-implemented method 1700 can, in various embodiments, comprise the same components as the computer-implemented method 1600, and can further comprise acts 1702 and 1704.

In various embodiments, act 1702 can include generating, by the device (e.g., visualization component 802), a three-dimensional maximum intensity projection (MIP) reconstruction (e.g., 3D MIP reconstruction 804) of the patient's brain based on the CTA images.

In various aspects, act 1704 can include displaying, by the device (e.g., visualization component 802), the three-dimensional MIP reconstruction to a user to facilitate visual verification of the LVO by the user.

Figure 18:
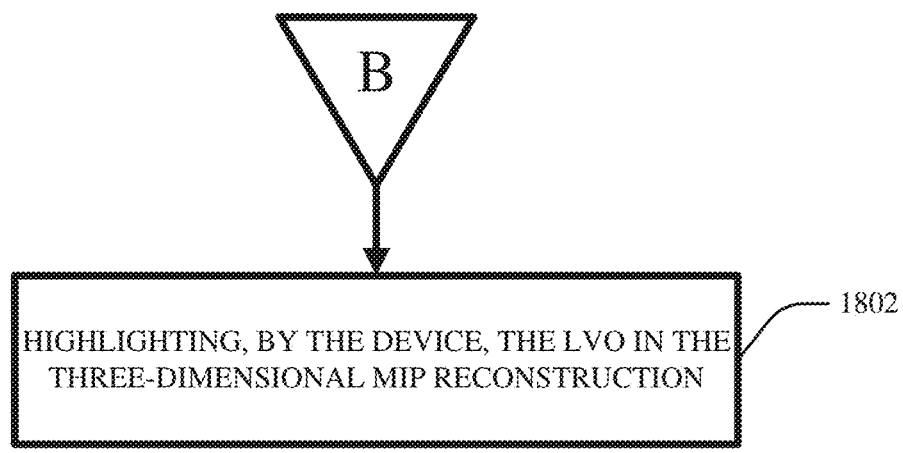
FIG. 18 illustrates a flow diagram of an example, non-limiting computer-implemented method including highlighting localized LVOs that facilitates automated localization of large vessel occlusions in accordance with one or more embodiments described herein.

FIG. 18 illustrates a flow diagram of an example, non-limiting computer-implemented method including highlighting localized LVOs that facilitates automated localization of large vessel occlusions in accordance with one or more embodiments described herein. As shown, the computer-implemented method 1800 can, in various embodiments, comprise the same components as the computer-implemented method 1700, and can further comprise act 1802.

In various embodiments, act 1802 can include highlighting, by the device (e.g., visualization component 802), the LVO in the three-dimensional MIP reconstruction.

Figure 19:
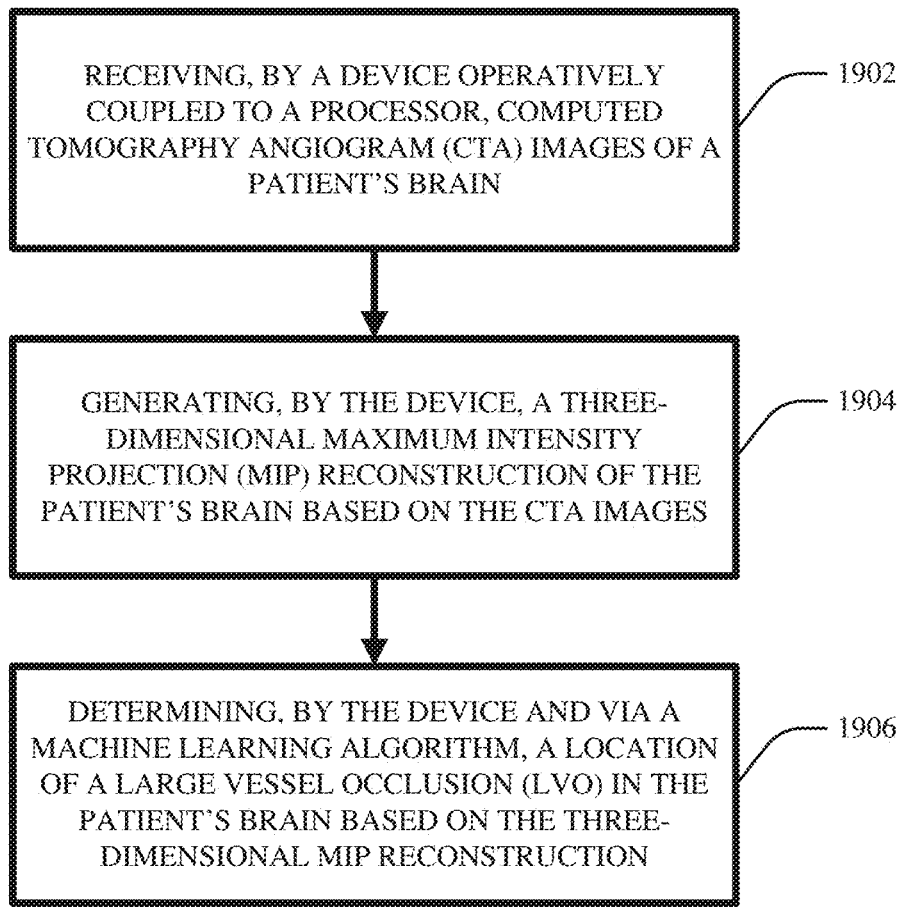
FIG. 19 illustrates a flow diagram of an example, non-limiting computer-implemented method that facilitates automated localization of large vessel occlusions in accordance with one or more embodiments described herein.

FIG. 19 illustrates a flow diagram of an example, non-limiting computer-implemented method 1900 that can facilitate automated localization of large vessel occlusions in accordance with one or more embodiments described herein.

In various embodiments, act 1902 can include receiving, by a device operatively coupled to a processor (e.g., input component 112), computed tomography angiogram (CTA) images (e.g., axial CTA images 104) of a patient's brain.

In various aspects, act 1904 can include generating, by the device (e.g., visualization component 802), a three-dimensional maximum intensity projection (MIP) reconstruction (e.g., 3D MIP reconstruction 804) of the patient's brain based on the CTA images.

In various instances, act 1906 can include determining, by the device (e.g., localization component 116) and via a machine learning algorithm (e.g., multi-classification model 602), a location of a large vessel occlusion (LVO) in the patient's brain based on the three-dimensional MIP reconstruction.

Figure 20:
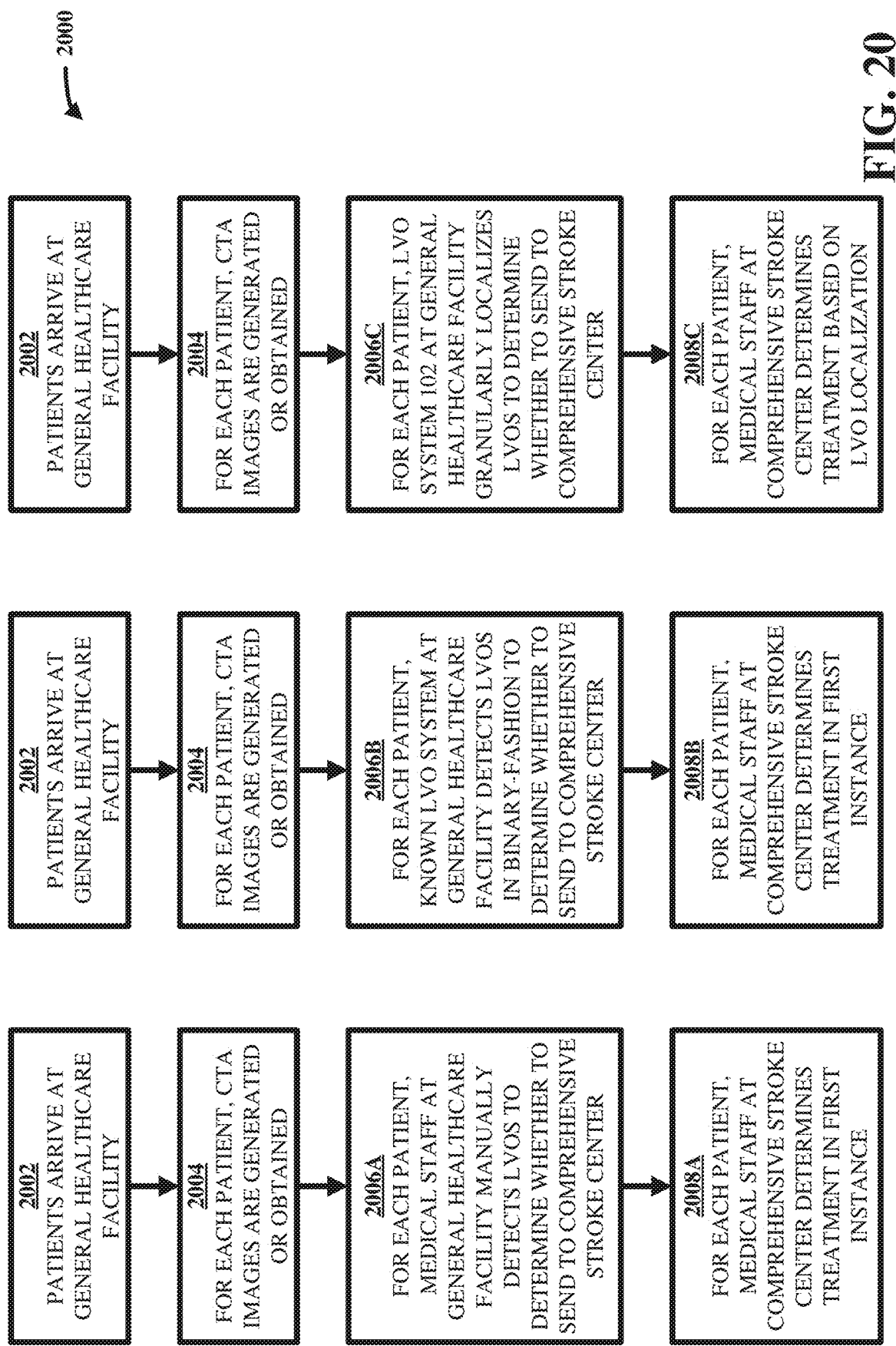
FIG. 20 compares clinical workflows that involve manual LVO detection and conventional automated LVO detection with an example, non-limiting clinical workflow that involves one or more embodiments of the subject innovation.

FIG. 20 compares clinical workflows that involve manual LVO detection and conventional automated LVO detection with an example, non-limiting clinical workflow that involves one or more embodiments of the subject innovation. As illustrated in FIG. 20 and as explained below, clinical workflows (e.g., real-world hospital environments) that implement embodiments of the subject innovation can experience significant benefits (e.g., reduced decision times, more accurate and/or more consistent LVO localization results, improved patient outcomes, and so on) as compared to clinical workflows that rely instead on manual LVO detection or conventional automated LVO detection.

In various aspects, the leftmost clinical workflow (e.g., comprising steps 2002, 2004, 2006A, and 2008A) can represent a clinical workflow that relies on manual LVO detection. At act 2002, patients can arrive (e.g., as walk-in patients, via emergency vehicles, and so on) at a general healthcare facility (e.g., a local hospital). At act 2004, for each patient, CTA images can be generated or obtained (e.g., generated by on-site CTA machinery, electronically or otherwise received from off-site CTA machinery, electronically or otherwise received from other healthcare facilities or databases, and so on). At act 2006A, for each patient, medical staff at the general healthcare facility can manually detect LVOs (e.g., by visually evaluating the CTA images) to determine whether to send the patient to a comprehensive stroke center. At act 2008A, for each transported patient, medical staff at the comprehensive stroke center can determine treatment in the first instance (e.g., determine the precise types, locations, and severities of LVOs in the patient so that an appropriate treatment can be administered, all without having the benefit of a prior granular LVO localization for verification or comparison purposes).

As mentioned above, small and/or general healthcare facilities often lack the equipment and resources required to appropriately address/treat LVOs. Instead, the necessary treatments (e.g., endovascular therapies) are generally available only at specialized stroke centers. Since the prospects of a positive clinical outcome decrease as the amount of time during which the patient goes untreated increases, and since transporting a patient from a general healthcare facility to a comprehensive stroke center can itself be quite time-consuming, it is paramount that LVOs are accurately detected at the general healthcare facility as quickly as possible. Unfortunately, manual detection of LVOs by medical staff can be time-consuming (e.g., it takes longer for humans to evaluate CTAs and/or MIPs than for trained machine learning algorithms to evaluate CTAs and/or MIPs), inaccurate (e.g., human error occurs more often than computer error, especially in high-stress hospital environments where medical staff are often working long hours and tending to multitudes of patients), and inconsistent (e.g., different medical practitioners can have different education and/or experience levels, such that manual LVO detection/localization varies by practitioner).

In various aspects, the middle clinical workflow (e.g., comprising steps 2002, 2004, 2006B, and 2008B) can represent a clinical workflow that relies on conventional automated LVO detection (e.g., binary LVO classification algorithms). As shown, acts 2002 and 2004 can be substantially the same as described above. At act 2006B, for each patient, a known (e.g., conventional) LVO system at the general healthcare facility can detect LVOs in binary-fashion (e.g., LVO detected, or LVO not detected) to determine whether to send the patient to a comprehensive stroke center. As shown, act 2008B can be substantially the same as act 2008A, where, for each transported patient, medical staff at the comprehensive stroke center can determine treatment in the first instance (e.g., determine the precise types, locations, and severities of LVOs in the patient so that an appropriate treatment can be administered, all without having the benefit of a prior granular LVO localization for verification or comparison purposes).

Although conventional LVO systems help to address some of the problems that plague manual LVO detection (e.g., less time consuming and removal of human error), they provide nothing more than a simple binary result that indicates either that an LVO was detected in the patient or that an LVO was not detected in the patient. Such a result provides no granular information about the detected LVO that can be used, leveraged, verified, or considered by subsequent medical staff at the comprehensive stroke center. As mentioned above, different types, locations, and/or severities of LVOs can require different treatments/therapies. Thus, knowing a granular localization of an LVO can aid in determining how best to address/treat it. Since conventional LVO systems do not provide such granular information, medical staff at the comprehensive stroke center are left to localize the LVO and evaluate status of collateral circulation in the first instance (e.g., on their own, from scratch, and so on). As explained below, embodiments of the subject innovation can address this shortcoming.

In various aspects, the rightmost clinical workflow (e.g., comprising steps 2002, 2004, 2006C, and 2008C) can represent a clinical workflow that implements one or more embodiments of the subject innovation. As shown, acts 2002 and 2004 can be substantially the same as described above. At act 2006C, for each patient, the LVO system 102 at the general healthcare facility can granularly localize LVOs to determine whether to send the patient to a comprehensive stroke center. As mentioned above, the LVO system 102 can, in some embodiments, perform such localization by analyzing automated 3D MIP reconstructions and/or projections of automated 3D MIP reconstructions, rather than directly analyzing raw CTA thin images or manually-created MIPs. As explained above, such analysis can result in accuracy and/or consistency benefits. At act 2008C, for each transported patient, medical staff at the comprehensive stroke center can determine treatment based on the LVO localization (e.g., since the LVO system 102 already granularly localized the LVO in the patient, the medical staff at the comprehensive stroke center can identify appropriate treatment/therapy without first having to localize the LVO). In some cases, the medical staff at the comprehensive stroke center can evaluate and/or verify the granular LVO localization generated by the LVO system 102 (e.g., by visually evaluating automated 3D MIP reconstructions generated/highlighted by the LVO system 102). Even in cases where the medical staff manually verify the LVO localization, it can require less time for them to do so since the LVO localization already identifies the specific location of interest in the patient's brain and/or other body part (e.g., laterality, occlusion site, and so on), meaning that the medical staff need not waste time evaluating irrelevant portions of the patient's CTAs or MIPs.

As shown, clinical workflows that implement one or more embodiments of the subject innovation experience substantial real-world benefits. Specifically, clinical workflows that involve embodiments of the subject innovation can experience reduced LVO detection/localization time, removal of human error, enhanced detection/localization consistency, and provision of granular localization information to be leveraged by the medical staff at the comprehensive stroke center. Such a clinical workflow can result in saved time, saved resources, and improved patient outcomes.

In various aspects, one or more of the following features can be implemented in various embodiments of the subject innovation. In various embodiments, the subject innovation can be trained to automatically determine, evaluate, and/or classify a severity of a detected/localized LVO in a patient. This can, in various cases, be facilitated by automatically evaluating status/profile of collateral circulation around the detected/localized LVO. A severity of an LVO can depend on the status of the collateral circulation corresponding to the LVO (e.g., an LVO that has sufficient/robust collateral circulation can be less serious than an LVO that has insufficient/malignant collateral circulation). In various aspects, the LVO system 102 can be trained to classify/evaluate collateral circulation if the training data 106 includes labels that indicate collateral status (e.g., supervised training). In various aspects, the LVO system 102 can be trained in an unsupervised or reinforcement learning fashion to evaluate collateral status. In various instances, the LVO system 102 can be trained to receive as input CTA images of a patient, and to provide as output a classification/evaluation of collateral circulation profile associated with detected/localized LVOs. As mentioned above, in some instances, the LVO system 102 can be trained to evaluate the 3D MIP reconstruction 804 (or projections thereof) in order to localize LVOs, rather than localizing LVOs by analyzing raw CTA images directly. Similarly, in some instances, the LVO system 102 can be trained to evaluate the 3D MIP reconstruction 804 (or projections thereof) in order to determine collateral status/profile of localized LVOs.

In various embodiments, the subject innovation can be trained to detect, localize, and/or evaluate other types of medical abnormalities in patients in addition to LVOs. For example, in some cases, the LVO system 102 can be trained to detect presence or absence of acute intracranial hemorrhage (ICH) on Non-Contrast Head CT (NCCT), which can be a key determinant in the triage of patients presenting with acute neurologic symptoms to ischemic or hemorrhagic stroke treatment pathways. In some aspects, the LVO system 102 can be trained to localize ICHs in patients and/or to provide further subtype characterization that can help to improve diagnostic speed and accuracy. In some instances, such subtype characterization can include intraparenchymal, subdural, epidural, intraventricular, subarachnoid, and so on. That is, in some instances, the LVO system 102 can be trained to receive as input NCCT series of a patient, and to produce as output detection/localization of ICH, and to further produce as output characterization of ICH into subtypes.

In various embodiments, the subject innovation can be trained to identify and/or quantify acute ischemic stroke on diffusion weighted imaging (DWI) and apparent coefficient map (ADC) based on magnetic resonance imaging (MRI). In such embodiments, the LVO system 102 can be trained to receive as input MRI DWI and ADC series corresponding to a patient, and can produce as output detection or localization of acute ischemic stroke in the patient. In some instances, the LVO system 102 can be trained to further produce as output image delineation and volume quantification of the detected or localized acute ischemic stroke.

Figure 21:
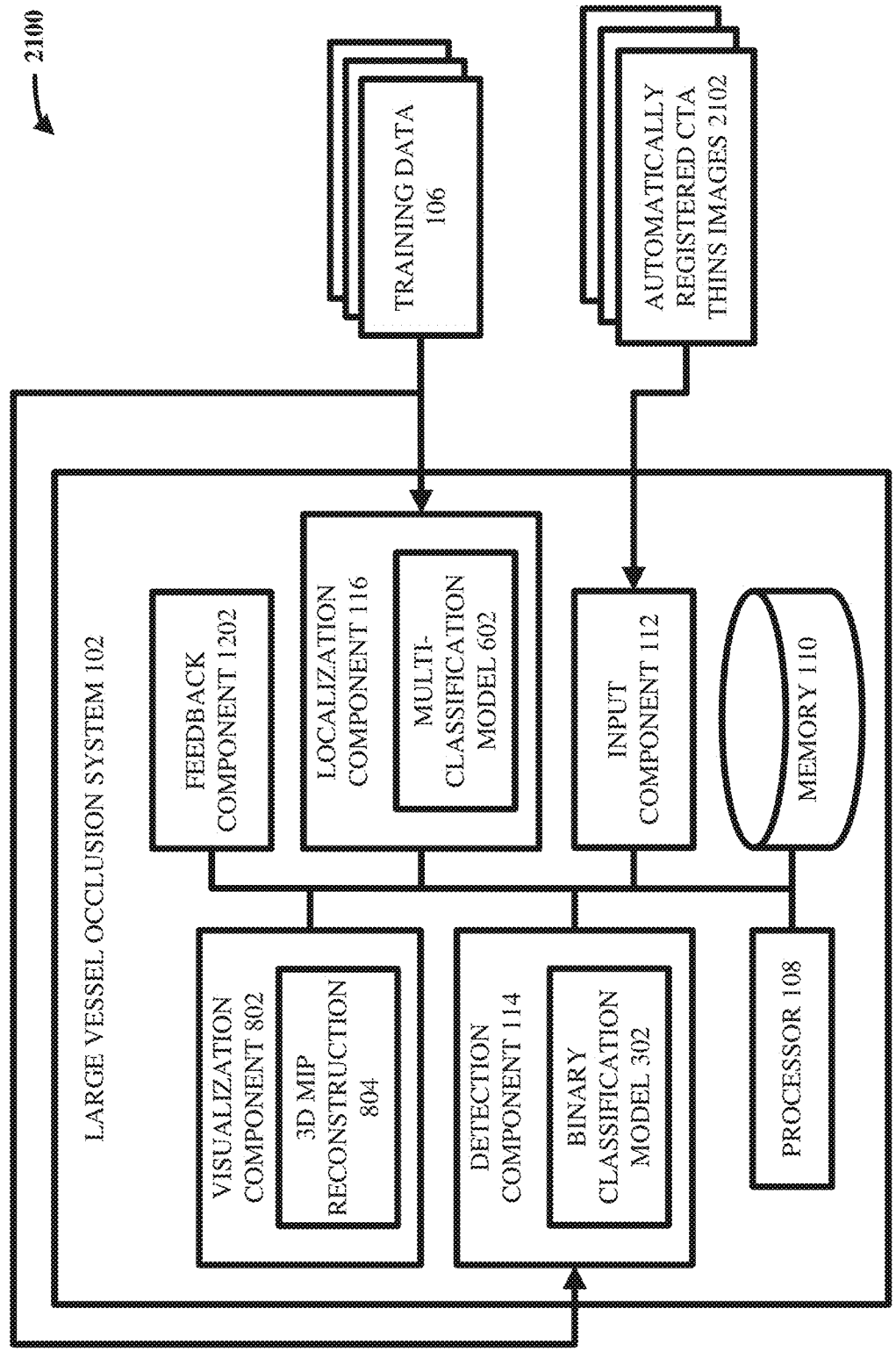
FIG. 21 illustrates a block diagram of an example, non-limiting system including automatically registered CTA THINS images that facilitates automated localization of large vessel occlusions in accordance with one or more embodiments described herein.

FIG. 21 illustrates a block diagram of an example, non-limiting system 2100 including automatically registered CTA THINS images that can facilitate automated localization of large vessel occlusions in accordance with one or more embodiments described herein. As shown, the system 2100 can, in some cases, comprise the same components as the system 800, and can further comprise automatically registered CTA THINS images 2102.

As explained above with respect to FIG. 8, in some cases, the LVO system 102 can automatically alter the axial CTA images 104 (e.g., preprocessing raw images) and can then perform LVO detection and/or localization on the altered images for improved results (e.g., the visualization component 802 can automatically generate the 3D MIP reconstruction 804 based on the axial CTA images 104, and the detection component 114 and/or the localization component 116 can execute on the 3D MIP reconstruction 804 rather that executing directly on the axial CTA images 104, which can provide more consistent detection/localization). In various other cases, however, the inventors of various embodiments of the subject innovation experimentally found that similar and/or better performance benefits can be achieved when the input component 112 directly receives automatically registered CTA THINS images 2102 rather than the axial CTA images 104 and rather than the 3D MIP reconstruction 804.

In various aspects, as explained above, the axial CTA images 104 can be raw images generated by any suitable CTA scanning apparatus. However, different CTA scanning apparatuses that are owned/operated by different entities can generate CTA images that exhibit different patient orientations, different zoom levels, different angular rotations, different planar translations, and/or other different image characteristics. In other words, raw CTA images (e.g., 104) can exhibit much image heterogeneity and/or non-standardization, which can make it more difficult for the detection component 114 and/or the localization component 116 to generate correct and/or consistent results (e.g., indeed, sometimes, a patient can be orientated such that the skull obscures vessels of interest in the brain). Moreover, such raw CTA images can also depict irrelevant and/or unwanted anatomical structures (e.g., referred to as background anatomical structures) that are not necessary/helpful for LVO detection (e.g., if the LVO system 102 is configured to detect/localize LVOs in a patient's brain, then depictions of the patient's neck or torso are not needed, and computing resources can be wasted by executing the detection component 114 and/or the localization component 116 on such unneeded image regions).

In various aspects, implementation of the automatically registered CTA THINS images 2102 can solve these problems. Specifically, the automatically registered CTA THINS images 2102 can be processed CTA images (e.g., not raw images) that are automatically formatted so as to present LVO studies (e.g., images of a patient) from any suitable standardized projection and so as to exclude anatomically unnecessary image regions (e.g., pixels depicting anatomical structures where an LVO is not of concern can be removed and/or cropped out). Because the automatically registered CTA THINS images 2102 can be shown from a standardized projection and can contain fewer pixels than raw CTA images, the detection component 114 and/or the localization component 116 can produce more accurate, more precise, and/or more efficient results. FIGS. 22-26 explain how the automatically registered CTA THINS images 2102 can be generated from the axial CTA images 104.

Figure 22:
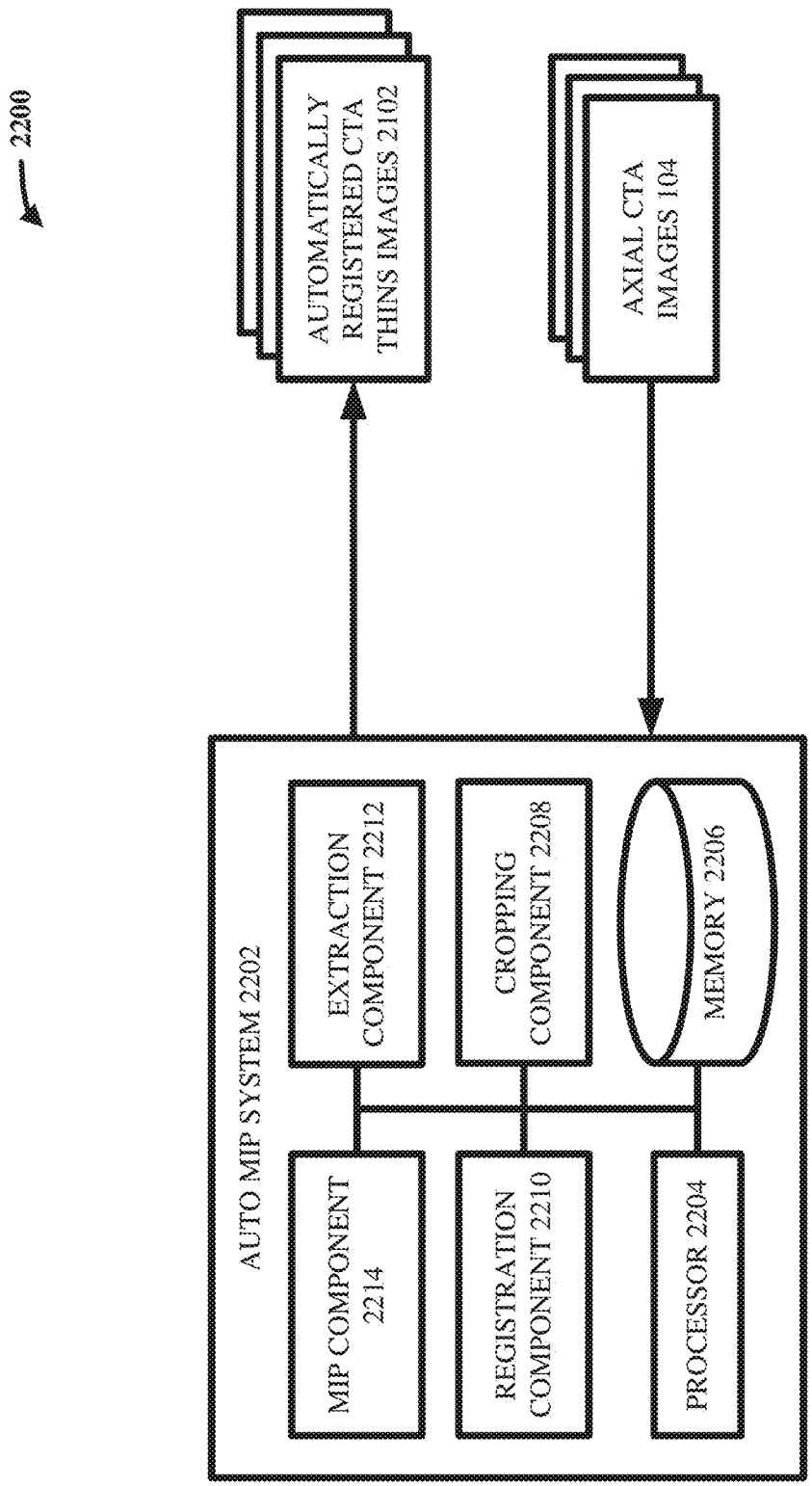
FIG. 22 illustrates a block diagram of an example, non-limiting system 2200 that facilitates automated generation of maximum intensity projections (MIPs) and/or automatically registered CTA THINS images in accordance with one or more embodiments described herein.

FIG. 22 illustrates a block diagram of an example, non-limiting system 2200 that can facilitate automated generation of maximum intensity projections (MIPs) and/or automatically registered CTA THINS images in accordance with one or more embodiments described herein. As shown, an auto MIP system 2202 can electronically receive in any suitable way the axial CTA images 104 as input and can electronically produce the automatically registered CTA THINS images 2102 as output.

In various embodiments, the auto MIP system 2202 can comprise a processor 2204 (e.g., computer processing unit, microprocessor, and so on) and a computer-readable memory 2206 that is operably and/or operatively and/or communicatively connected/coupled to the processor 2204. The memory 2206 can store computer-executable instructions which, upon execution by the processor 2204, can cause the processor 2204 and/or other components of the auto MIP system 2202 (e.g., cropping component 2208, registration component 2210, extraction component 2212, and MIP component 2214) to perform one or more acts. In various embodiments, the memory 2206 can store computer-executable components (e.g., cropping component 2208, registration component 2210, extraction component 2212, and MIP component 2214), and the processor 2204 can execute the computer-executable components.

In various embodiments, the auto MIP system 2202 can comprise a cropping component 2208. In various aspects, the cropping component 2208 can include any suitable machine learning model (e.g., neural network) that can be trained to receive as input the axial CTA images 104 and to determine as output one or more cutoff lines that demarcate and/or separate LVO-relevant anatomical regions depicted in the axial CTA images 104 from LVO-irrelevant anatomical regions depicted in the axial CTA images 104. For one CTA image, a cutoff line can be perceived as a row and/or column of pixels. For a series of CTA images, a cutoff line can be a horizontal and/or vertical plane of pixels (e.g., one image represents two-dimensional pixel data, and rows/columns of pixels can be used to segment two-dimensional pixel data; a series of images represents three-dimensional pixel data (voxels), and planes of pixels can be used to segment the three-dimensional pixel data (voxels)). Once the cutoff lines are determined, the cropping component 2208 can electronically crop the axial CTA images 104 (e.g., can remove the LVO-irrelevant anatomical regions from the axial CTA images 104). For instance, suppose that a series of raw CTA images depict a patient's head and neck (e.g., the three-dimensional pixel data can represent the patient's head and neck). In such case, the cropping component can, via the trained machine learning model, identify a cutoff line (e.g., a horizontal plane of pixels) that is positioned between a jaw of the patient (e.g., a mandible bone) and a neck of the patient (e.g., cervical vertebrae). In such case, the three-dimensional pixel data above the cutoff line can depict the skull, jaw, and brain of the patient (e.g., LVO-relevant anatomical regions) and the three-dimensional pixel data below the cutoff line can depict the neck and/or throat of the patient (e.g., LVO-irrelevant anatomical regions). The cropping component 2208 can then electronically remove the pixels below the cutoff line (e.g., can crop out the neck of the patient) from the series of raw CTA images, thereby leaving a series of cropped CTA images that depict the skull, jaw, and brain of the patient and that do not depict the neck of the patient. That is, the cropping component 2208 can convert the axial CTA images 104 into cropped CTA images.

In various embodiments, the auto MIP system 2202 can comprise a registration component 2210. In various aspects, the registration component 2210 can facilitate three-dimensional rigid body registration of the series of cropped CTA images produced by the cropping component 2208. In the field of medical imaging, registration can be the process of aligning and/or orienting medical imaging data to a desired projection (e.g., to a desired angular rotation, a desired zoom level, a desired translational position, a desired anatomical orientation, and/or so on). The registration component 2210 can facilitate such three-dimensional rigid body registration via any suitable computational techniques, such as by utilizing three-dimensional image perturbations based on a registration template. In various aspects, a registration template can be a pre-stored series of CTA images that depict LVO-relevant anatomical regions in a desired and/or standard projection. In various cases, the registration component 2210 can receive the series of cropped CTA images from the cropping component 2208, can compare the series of cropped CTA images to the registration template, and can continually perturb (e.g., rotate by small angles about any suitable axis in three-dimensional space, zoom in/out by small magnitudes along as suitable axis in three-dimensional space, translate by small magnitudes along any suitable axis in three-dimensional space) the series of cropped CTA images until they are aligned with (e.g., until they have the same projection as) the registration template. In some cases, such alignment can be defined according to any suitable registration margin of error and/or threshold. Thus, the registration component 2210 can convert the cropped CTA images of the cropping component 2208 into registered and cropped CTA images.

In various embodiments, the auto MIP system 2202 can comprise an extraction component 2212. In various aspects, the registration template leveraged by the registration component 2210 can include a predefined region of interest. In various cases, the extraction component 2212 can identify an analogous and/or corresponding region of interest in the registered and cropped CTA images and can extract such region (e.g., can crop away any pixels that are not within the analogous and/or corresponding region of interest), thereby removing even more anatomical structures that are not of interest and/or that are not desired to be checked for LVOs. For example, the registration template can be a three-dimensional pixel volume, and the predefined region can be some smaller three-dimensional pixel volume that is located at a particular position within the registration template. Likewise, the registered and cropped CTA images generated by the registration component 2210 can also be a three-dimensional pixel volume. In various cases, the extraction component 2212 can identify within the registered and cropped CTA images a smaller three-dimensional pixel volume that is located at the same particular position as the predefined region (e.g., the predefined region can be bounded by any suitable Cartesian coordinates $x_a$ to $x_b$, $y_a$ to $y_b$, and $z_a$ to $z_b$ within the registration template, and the extracted portion can be bounded by the same Cartesian coordinates $x_a$ to $x_b$, $y_a$ to $y_b$, and $z_a$ to $z_b$ within the registered and cropped CTA images). In some cases, the predefined region can be defined for a particular laterality, and mirroring can be implemented to obtain a predefined region for the other laterality (e.g., the predefined region might be a bounding box superimposed over a right-laterality in the registration template; in such case, a predefined region for the left-laterality can be obtained by simply reflecting the predefined region for the right-laterality over a suitable axis). In various aspects, the predefined region can be an isolated view of the ICA vessel, the MCA-M1 vessel, the MCA-M2 vessel, and/or any other suitable anatomical structure that is desired to be analyzed for LVOs. In various aspects, the regions extracted by the extraction component 2212 from the registered and cropped CTA images can be considered as the automatically registered CTA THINS images 2102 (e.g., they are presented according to a standardized and/or desired projection, and they exclude anatomical structures that are irrelevant and/or undesired for LVO detection/localization).

In various embodiments, the auto MIP system 2202 can comprise an MIP component 2214. In various aspects, the MIP component 2214 can receive as input the registered and cropped CTA images produced by the registration component 2210 and can generate strided maximum intensity projections along any suitable planes (e.g., axial, coronal, sagittal). In various aspects, the MIP component 2214 can then render on any suitable electronic display (not shown in FIG. 22) the strided maximum intensity projections as desired. For example, in some cases, the MIP component 2214 can visually display the strided maximum intensity projections on a computer screen/monitor so that they are visible to surgeons and/or other medical professionals. In some cases, the MIP component 2214 can receive input from such surgeons and/or medical professionals (e.g., via keyboards, keypads, touchscreens, voice commands, and/or any other suitable input device), which input can identify particular projections to be displayed (e.g., the MIP component 2214 can display a selected axial projection in response to input from a doctor, can display a selected coronal projection in response to input from the doctor, can display a selected sagittal projection in response to input from the doctor).

Figure 23:
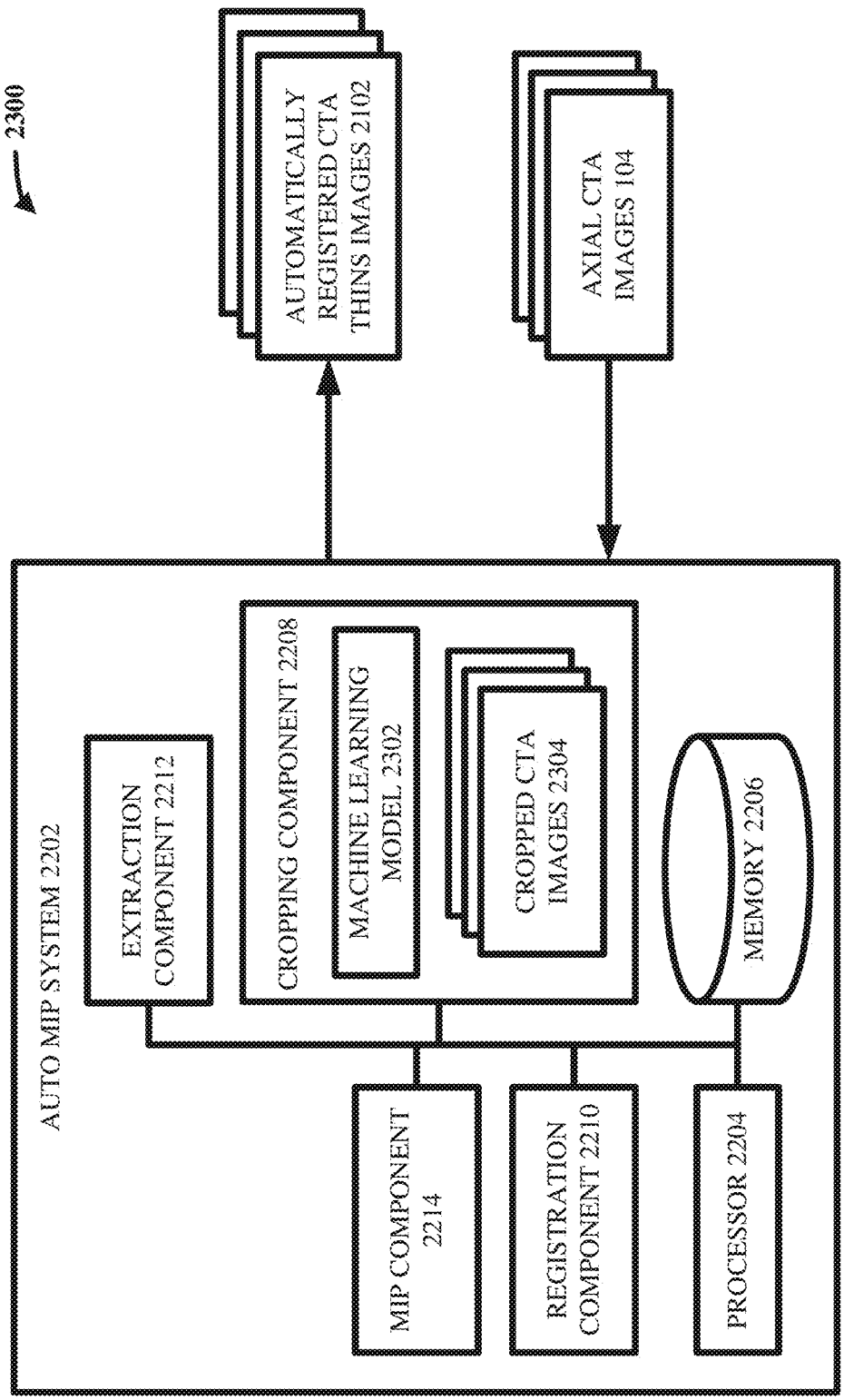
FIG. 23 illustrates a block diagram of an example, non-limiting system including cropped CTA images that facilitates automated generation of maximum intensity projections (MIPs) and/or automatically registered CTA THINS images in accordance with one or more embodiments described herein.

FIG. 23 illustrates a block diagram of an example, non-limiting system 2300 including cropped axial CTA images that can facilitate automated generation of maximum intensity projections (MIPs) and/or automatically registered CTA THINS images in accordance with one or more embodiments described herein. As shown, the system 2300 can, in some cases, comprise the same components as the system 2200, and can further comprise a machine learning model 2302 and cropped CTA images 2304.

In various aspects, the cropping component 2208 can comprise the machine learning model 2302. In various instances, the machine learning model 2302 can be any suitable computationally-implemented artificial intelligence algorithm that can be trained (e.g., via supervised learning, unsupervised learning, and/or reinforcement learning) to receive as input the axial CTA images 104 and to determine as output one or more cutoff lines in the axial CTA images 104. As mentioned, the axial CTA images 104 can represent a three-dimensional pixel volume, and such a volume can be partitioned, segmented, and/or separated by planes of pixels. Thus, in various cases, the machine learning model 2302 can identify one or more planes of pixels within the axial CTA images 104, which planes of pixels separate anatomical structures of interest from background anatomical structures (e.g., the machine learning model 2302 can be trained to recognize first pixels that represent a skull, jaw, and/or brain in the axial CTA images 104; to recognize second pixels that represent a neck and/or throat in the axial CTA images; and to identify a horizontal and/or vertical plane of pixels that separates and/or lies between the first and second pixels).

Once the machine learning model 2302 determines the one or more cutoff lines, the cropping component 2208 can remove and/or delete the second pixels that represent background anatomical structures while preserving the first pixels that represent anatomical structures of interest (e.g., can delete pixels that are positioned below the cutoff line and can maintain pixels that are positioned above the cutoff line). That is, the cropping component 2208 can crop the axial CTA images 104, thereby yielding the cropped CTA images 2304. In various aspects, the cropped CTA images 2304 can lack the background anatomical structures, which can make subsequent registration and/or subsequent detection/localization of LVOs easier.

In various embodiments, the machine learning model 2302 can be a DenseNet regression network and can implement a self-supervised training regime. In various aspects, the machine learning model 2302 can embed slices in a one-dimensional latent space such that distances in the latent space match distances in the corresponding real-world physical space.

Figure 24:
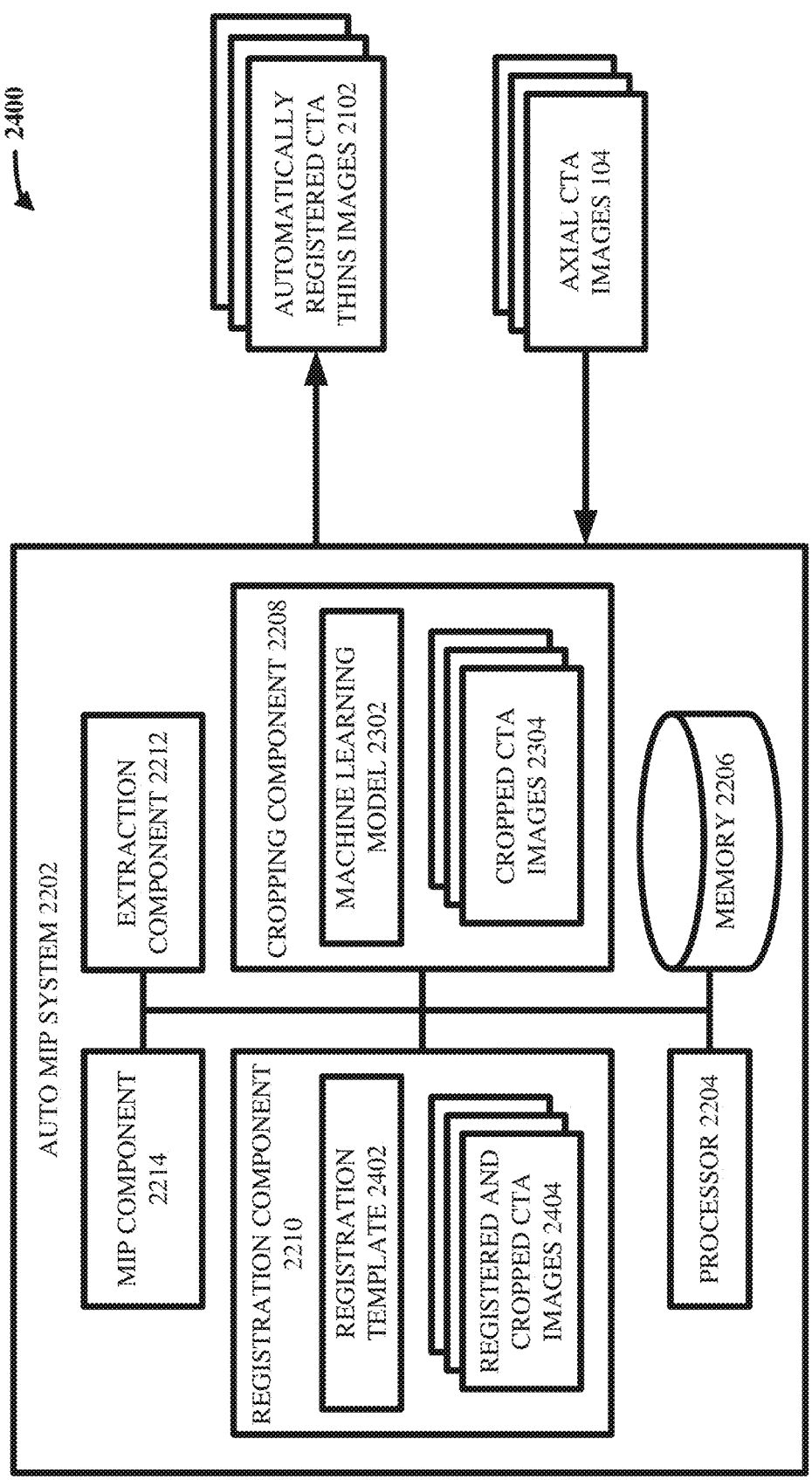
FIG. 24 illustrates a block diagram of an example, non-limiting system including a registration template and registered and cropped CTA images that facilitates automated generation of maximum intensity projections (MIPs) and/or automatically registered CTA THINS images in accordance with one or more embodiments described herein.

FIG. 24 illustrates a block diagram of an example, non-limiting system 2400 including a registration template and registered and cropped axial CTA images that can facilitate automated generation of maximum intensity projections (MIPs) and/or automatically registered CTA THINS images in accordance with one or more embodiments described herein. As shown, the system 2400 can, in some cases, comprise the same components as the system 2300, and can further comprise a registration template 2402 and registered and cropped CTA images 2404.

In various aspects, the registration component 2210 can electronically store, maintain, and/or otherwise have access to a registration template 2402. As mentioned above, the registration template 2402 can be three-dimensional pixel data that represent generic anatomical structures of interest from a desired and/or standardized projection. In various aspects, the registration component 2210 can leverage the registration template 2402 to perform three-dimensional rigid body registration (e.g., three-dimensional alignment) on the cropped CTA images 2304. In various cases, three-dimensional rigid body registration can be facilitated via image perturbations. That is, the registration component 2210 can compare the cropped CTA images 2304 with the registration template 2402, and can continually perturb (e.g., rotate, translate, reorient, zoom in/out) the cropped CTA images 2304 until the cropped CTA images 2304 exhibit a projection that matches the desired and/or standardized projection of the registration template 2402. In some cases, the projection of the cropped CTA images 2304 can be considered as matching the desired and/or standardized projection of the registration template 2402 if it is within any suitable error margin (e.g., 1%) of the desired and/or standardized projection. In some cases, studies having too high a registration error can be excluded and/or deleted. The result of such perturbation can be the registered and cropped CTA images 2404. In various aspects, the registered and cropped CTA images 2404 can exhibit the desired and/or standardized projection, which can make subsequent LVO detection/localization easier and/or more accurate (e.g., can ensure that vessels of interest are not obscured by other anatomical structures that are depicted in the cropped CTA images 2304).

In various aspects, the registration component 2210 can perform any suitable three-dimensional similarity transformation on a subsampled image, can implement iterative gradient descent (e.g., about 3 seconds per study), and can implement a mean square intensity distance loss function.

Figure 25:
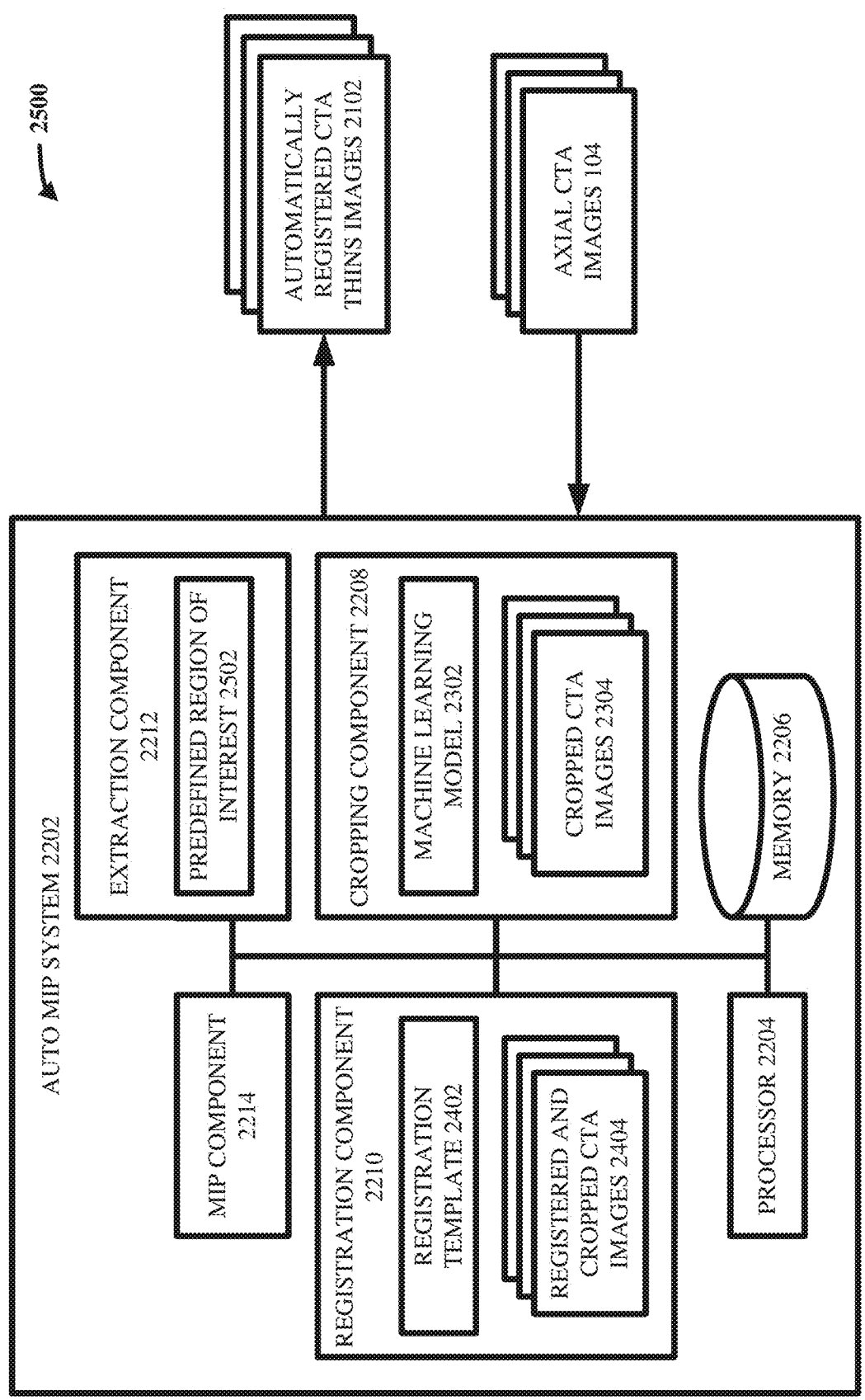
FIG. 25 illustrates a block diagram of an example, non-limiting system including a predefined region of interest that facilitates automated generation of maximum intensity projections (MIPs) and/or automatically registered CTA THINS images in accordance with one or more embodiments described herein.

FIG. 25 illustrates a block diagram of an example, non-limiting system 2500 including a predefined region of interest that can facilitate automated generation of maximum intensity projections (MIPs) and/or automatically registered CTA THINS images in accordance with one or more embodiments described herein. As shown, the system 2500 can, in some cases, comprise the same components as the system 2400, and can further comprise a predefined region of interest 2502.

In some embodiments, the registration template 2402 can comprise a predefined region of interest 2502. That is, the registration template 2402 can be a three-dimensional volume of pixel data, and the predefined region of interest 2502 can be a smaller three-dimensional volume of pixel data within the registration template 2402 and that is located in a position that is believed to be important for LVO detection. For example, the registration template 2402 can be three-dimensional data representing a patient's skull and brain, and the predefined region of interest 2502 can be three-dimensional data that is located at a particular site in the patient's brain (e.g., at the ICA site, at the MCA-M1 site, at the MCA-M2 site). In various aspects, the extraction component 2212 can crop the registered and cropped CTA images 2404 based on the predefined region of interest 2502. That is, the extraction component 2212 can identify within the registered and cropped CTA images 2404 a particular three-dimensional region that has the same and/or analogous location as the predefined region of interest 2502 in the registration template 2402. Then, the extraction component 2212 can preserve the pixel data of the registered and cropped CTA images 2404 that is within this particular three-dimensional region and can delete the pixel data that is outside of this particular three-dimensional region. The preserved pixel data can be considered as the automatically registered CTA THINS images 2102.

Overall, the axial CTA images 104 can be cropped (e.g., via 2208) a first time to remove background anatomical structures (e.g., to remove pixels representing the patient's neck and to preserve pixels representing the patient's head), thereby yielding the cropped CTA images 2304; the cropped CTA images 2304 can be registered (e.g., via 2210) so that they are aligned with a desired/standard projection (e.g., a standard cross-section of the patient's head is taken), thereby yielding the registered and cropped CTA images 2404; and particular regions of interest can be extracted (e.g., via 2212) from the registered and cropped CTA images 2404 (e.g., the pixels representing the ICA site, the MCA-M1 site, and/or the MCA-M2 site can be extracted and analyzed in isolation; pixels representing the cranial bone can be omitted since LVOs do not form in the cranial bone), thereby yielding the automatically registered CTA THINS images 2102. In various aspects, the automatically registered CTA THINS images 2102 can then be fed to the LVO system 102 for detection/localization.

Figure 26:
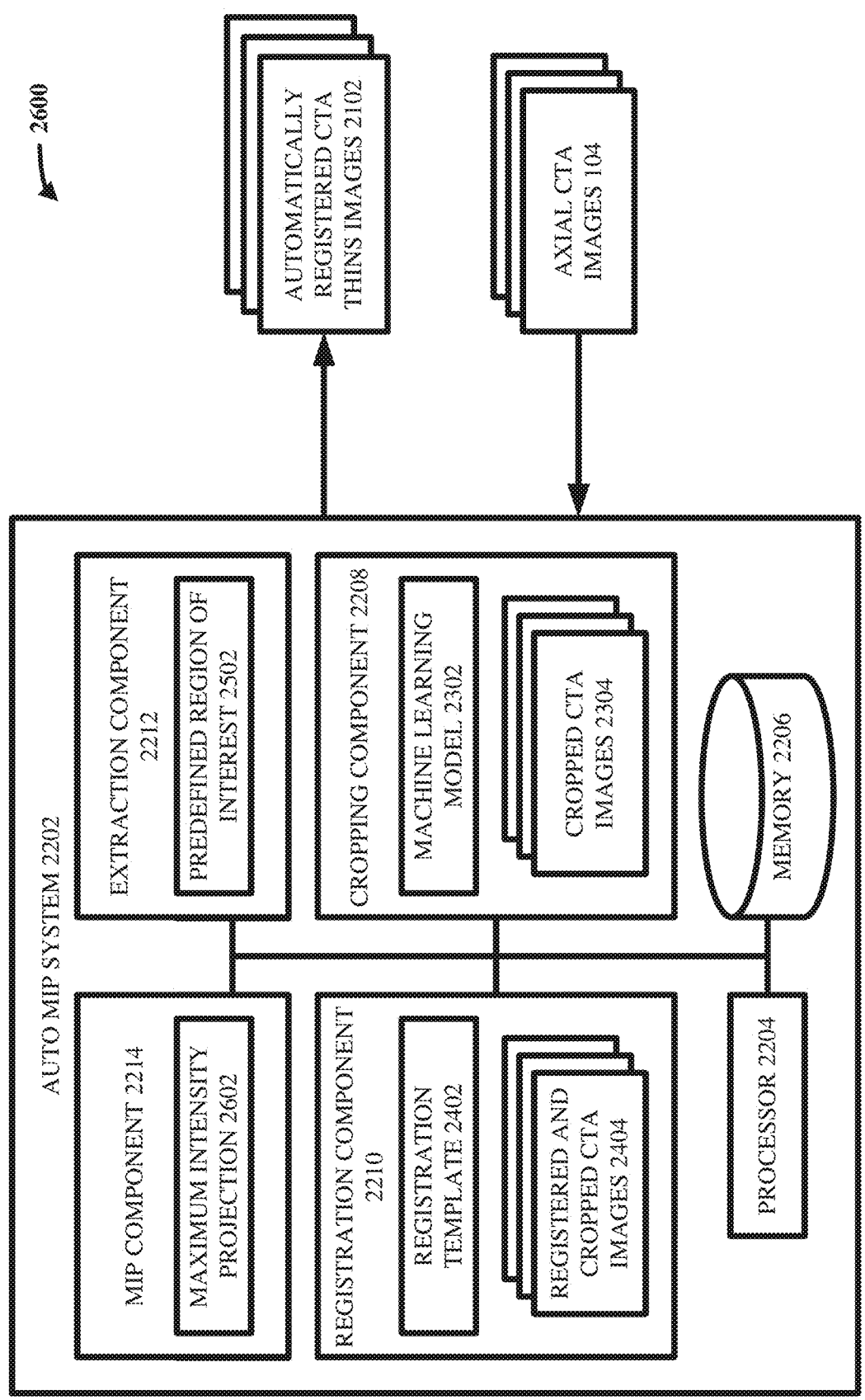
FIG. 26 illustrates a block diagram of an example, non-limiting system including a maximum intensity projection that facilitates automated generation of maximum intensity projections (MIPs) and/or automatically registered CTA THINS images in accordance with one or more embodiments described herein.

FIG. 26 illustrates a block diagram of an example, non-limiting system 2600 including a maximum intensity projection that can facilitate automated generation of maximum intensity projections (MIPs) and/or automatically registered CTA THINS images in accordance with one or more embodiments described herein. As shown, the system 2600 can, in some cases, comprise the same components as the system 2500, and can further comprise a maximum intensity projection 2602.

The above discussion explains how the auto MIP system 2202 can generate registered/aligned input image data that can be fed to the LVO system 102 (and/or to any other suitable machine learning system) to facilitate LVO detection and/or localization. In various embodiments, however, the MIP component 2214 can provide visualizations that can be used by medical professionals when diagnosing and/or treating LVOs. Specifically, the MIP component 2214 can generate a maximum intensity projection 2602 based on the registered and cropped CTA images 2404. As mentioned above, the registered and cropped CTA images 2404 can be three-dimensional pixel data (voxels) that depicts a patient's head (e.g., skull and/or brain). In some cases, the MIP component 2214 can take strided maximum intensity projections along any suitable axis and/or plane (e.g., axial, coronal, sagittal). In various aspects, the maximum intensity projection 2602 can be any of such plurality of strided maximum intensity projections. In various instances, the MIP component 2214 can electronically render the maximum intensity projection 2602 on any suitable computer screen/monitor (e.g., so that it can be visible to a medical professional). In some cases, the MIP component 2214 can receive input from a medical professional (e.g., via keyboard, touchscreen, voice command), which input indicates a selection of a particular maximum intensity projection that the medical professional would like to see. In such cases, the MIP component 2214 can render such selected maximum intensity projections on the computer screen/monitor. The inventors of various embodiments of the subject innovation experimentally verified that the maximum intensity projection 2602, in various embodiments, is not inferior to manually-created MIPs (e.g., repeated blind evaluations by radiologists were conducted; radiologists generally were not able to distinguish between automatically-generated MIPs and manually-generated MIPs).

In various aspects, the MIP component 2214 can transform THINS to a template space via any suitable known transformation, can resample on a grid with isotropic spacing in-place and a 0.5 mm spacing between places, can take an MIP with width 60 slices and stride 10 slices, and can then place the MIP in a DICOM file.

Overall, the auto MIP system 2202 can align (e.g., via 2210) an acquired CTA image to a canonical spatial reference frame. In this way, the resulting MIPS can have the correct spatial alignment (e.g., exhibited by 2402), which can be important for ensuring that the skull does not obscure the vessels. Prior to alignment, a slice selection neural network model (e.g., 2302) can be used to identify slices that represent the head and remove other areas of the image (such as the neck) that may interfere with the alignment process. The alignment process optimizes the translation, rotation and scaling parameters in order to best align the image to a canonical example. After alignment, strided maximum intensity projections can be taken (e.g., via 2214) along each of the three standard planes (axial, coronal and sagittal) to produce standard MIP images suitable for radiologist interpretation.

Figure 27:
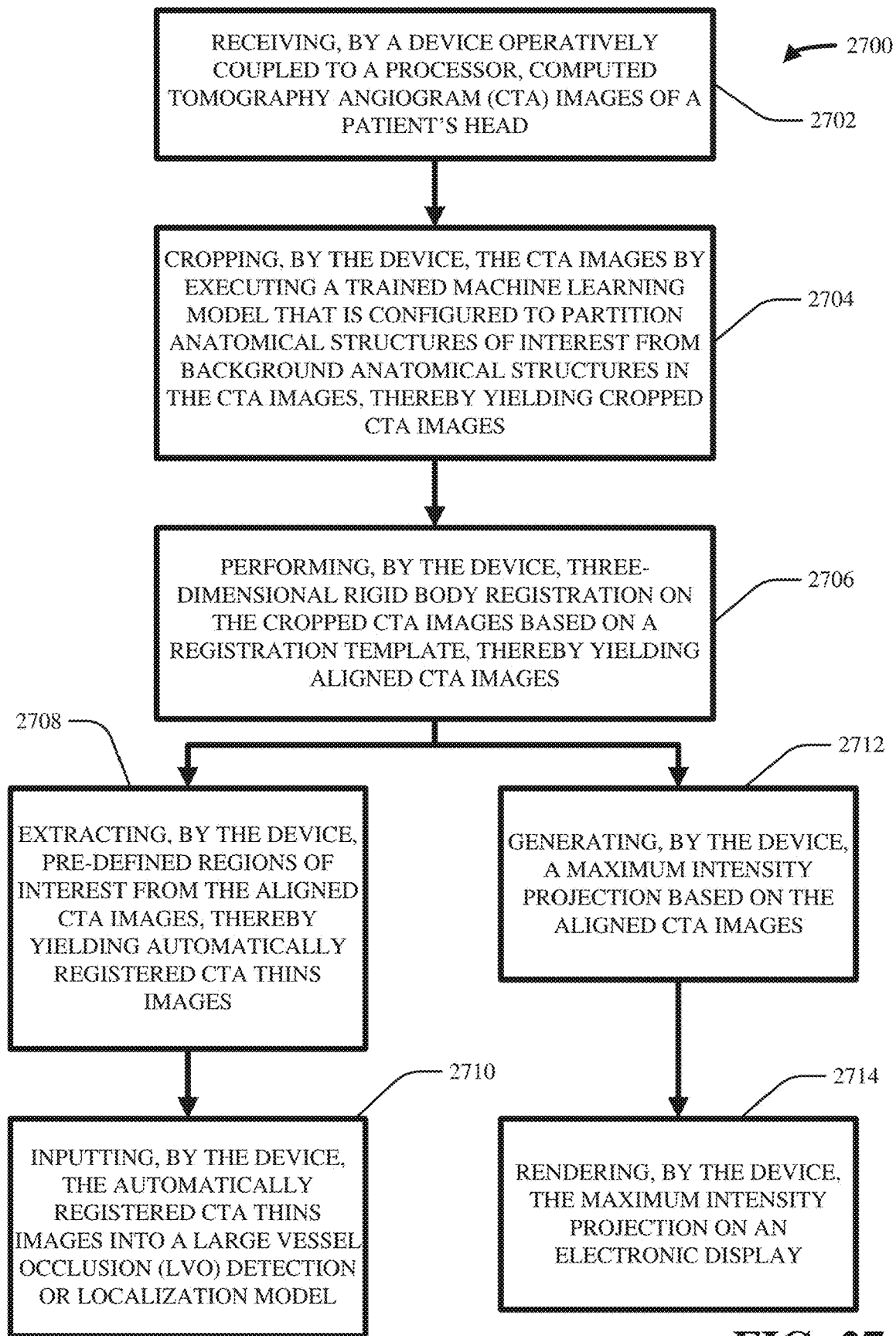
FIG. 27 illustrates a flow diagram of an example, non-limiting computer-implemented method that facilitates automated generation of maximum intensity projections (MIPs) and/or automatically registered CTA THINS images in accordance with one or more embodiments described herein.

FIG. 27 illustrates a flow diagram of an example, non-limiting computer-implemented method 2700 that can facilitate automated generation of maximum intensity projections (MIPs) and/or automatically registered CTA THINS images in accordance with one or more embodiments described herein. In some cases, the computer-implemented algorithm 2700 can be facilitated by the system 2600.

In various embodiments, act 2702 can include receiving, by a device operatively coupled to a processor (e.g., 2202), computed tomography angiogram (CTA) images of a patient's head (e.g., 104).

In various aspects, act 2704 can include cropping, by the device (e.g., 2208), the CTA images by executing a trained machine learning model (e.g., 2302) that is configured to partition anatomical structures of interest from background anatomical structures in the CTA images, thereby yielding cropped CTA images (e.g., 2304).

In various instances, act 2706 can include performing, by the device (e.g., 2210), three-dimensional rigid body registration on the cropped CTA images based on a registration template (e.g., 2402), thereby yielding aligned CTA images (e.g., 2404). In some cases, act 2708 can follow act 2706. In some cases, act 2712 can follow act 2706.

In various aspects, act 2708 can include extracting, by the device (e.g., 2212), predefined regions of interest (e.g., 2502) from the aligned CTA images, thereby yielding automatically registered CTA THINS images (e.g., 2102).

In various cases, act 2710 can include inputting, by the device, the automatically registered CTA THINS images into a large vessel occlusion (LVO) detection or localization model (e.g., 102).

In various instances, act 2712 can include generating, by the device (e.g., 2214), a maximum intensity projection (e.g., 2602) based on the aligned CTA images.

In various cases, act 2714 can include rendering, by the device (e.g., 2214), the maximum intensity projection on an electronic display.

As explained above, the auto MIP system 2202 can, in some cases, electronically generate image data that can be fed as input to a detection/localization model. In other cases, the auto MIP system 2202 can generate as output a MIP visualization that can be inspected and/or leveraged by medical professionals.

Figure 28:
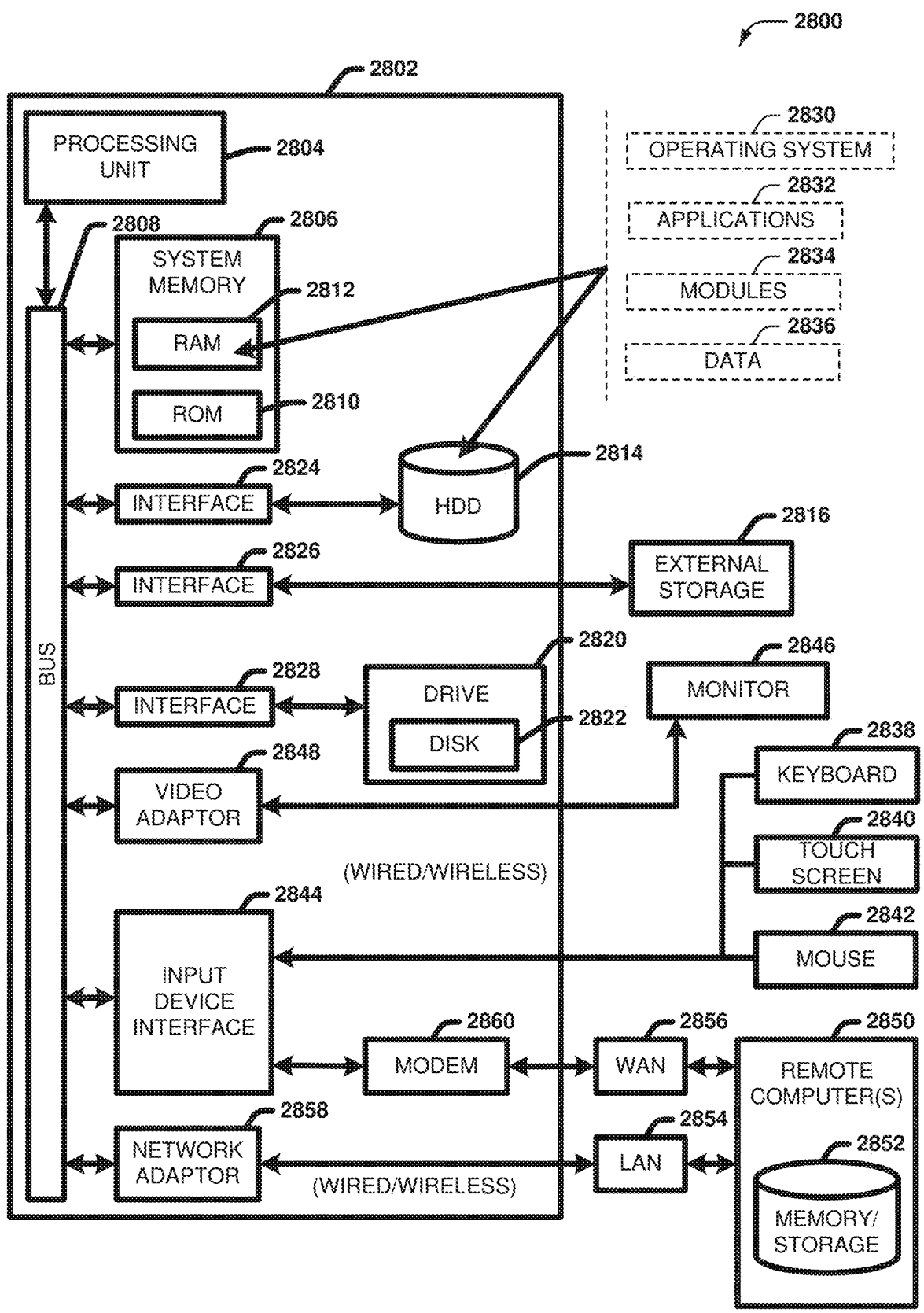
FIG. 28 illustrates a block diagram of an example, non-limiting operating environment in which one or more embodiments described herein can be facilitated.

In order to provide additional context for various embodiments described herein, FIG. 28 and the following discussion are intended to provide a brief, general description of a suitable computing environment 2800 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 28, the example environment 2800 for implementing various embodiments of the aspects described herein includes a computer 2802, the computer 2802 including a processing unit 2804, a system memory 2806 and a system bus 2808. The system bus 2808 couples system components including, but not limited to, the system memory 2806 to the processing unit 2804. The processing unit 2804 can be any of various commercially available processors. Dual microprocessors and other multi processor architectures can also be employed as the processing unit 2804.

The system bus 2808 can be any of several types of bus structure that can further interconnect to a memory bus (with or without a memory controller), a peripheral bus, and a local bus using any of a variety of commercially available bus architectures. The system memory 2806 includes ROM 2810 and RAM 2812. A basic input/output system (BIOS) can be stored in a non-volatile memory such as ROM, erasable programmable read only memory (EPROM), EEPROM, which BIOS contains the basic routines that help to transfer information between elements within the computer 2802, such as during startup. The RAM 2812 can also include a high-speed RAM such as static RAM for caching data.

The computer 2802 further includes an internal hard disk drive (HDD) 2814 (e.g., EIDE, SATA), one or more external storage devices 2816 (e.g., a magnetic floppy disk drive (FDD) 2816, a memory stick or flash drive reader, a memory card reader, etc.) and a drive 2820, e.g., such as a solid state drive, an optical disk drive, which can read or write from a disk 2822, such as a CD-ROM disc, a DVD, a BD, etc. Alternatively, where a solid state drive is involved, disk 2822 would not be included, unless separate. While the internal HDD 2814 is illustrated as located within the computer 2802, the internal HDD 2814 can also be configured for external use in a suitable chassis (not shown). Additionally, while not shown in environment 2800, a solid state drive (SSD) could be used in addition to, or in place of, an HDD 2814. The HDD 2814, external storage device(s) 2816 and drive 2820 can be connected to the system bus 2808 by an HDD interface 2824, an external storage interface 2826 and a drive interface 2828, respectively. The interface 2824 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 2802, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 2812, including an operating system 2830, one or more application programs 2832, other program modules 2834 and program data 2836. All or portions of the operating system, applications, modules, and/or data can also be cached in the RAM 2812. The systems and methods described herein can be implemented utilizing various commercially available operating systems or combinations of operating systems.

Computer 2802 can optionally comprise emulation technologies. For example, a hypervisor (not shown) or other intermediary can emulate a hardware environment for operating system 2830, and the emulated hardware can optionally be different from the hardware illustrated in FIG. 28. In such an embodiment, operating system 2830 can comprise one virtual machine (VM) of multiple VMs hosted at computer 2802. Furthermore, operating system 2830 can provide runtime environments, such as the Java runtime environment or the .NET framework, for applications 2832. Runtime environments are consistent execution environments that allow applications 2832 to run on any operating system that includes the runtime environment. Similarly, operating system 2830 can support containers, and applications 2832 can be in the form of containers, which are lightweight, standalone, executable packages of software that include, e.g., code, runtime, system tools, system libraries and settings for an application.

Further, computer 2802 can be enable with a security module, such as a trusted processing module (TPM). For instance with a TPM, boot components hash next in time boot components, and wait for a match of results to secured values, before loading a next boot component. This process can take place at any layer in the code execution stack of computer 2802, e.g., applied at the application execution level or at the operating system (OS) kernel level, thereby enabling security at any level of code execution.

A user can enter commands and information into the computer 2802 through one or more wired/wireless input devices, e.g., a keyboard 2838, a touch screen 2840, and a pointing device, such as a mouse 2842. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 2804 through an input device interface 2844 that can be coupled to the system bus 2808, but can be connected by other interfaces, such as a parallel port, an IEEE 1394 serial port, a game port, a USB port, an IR interface, a BLUETOOTH® interface, etc.

A monitor 2846 or other type of display device can be also connected to the system bus 2808 via an interface, such as a video adapter 2848. In addition to the monitor 2846, a computer typically includes other peripheral output devices (not shown), such as speakers, printers, etc.

The computer 2802 can operate in a networked environment using logical connections via wired and/or wireless communications to one or more remote computers, such as a remote computer(s) 2850. The remote computer(s) 2850 can be a workstation, a server computer, a router, a personal computer, portable computer, microprocessor-based entertainment appliance, a peer device or other common network node, and typically includes many or all of the elements described relative to the computer 2802, although, for purposes of brevity, only a memory/storage device 2852 is illustrated. The logical connections depicted include wired/wireless connectivity to a local area network (LAN) 2854 and/or larger networks, e.g., a wide area network (WAN) 2856. Such LAN and WAN networking environments are commonplace in offices and companies, and facilitate enterprise-wide computer networks, such as intranets, all of which can connect to a global communications network, e.g., the Internet.

When used in a LAN networking environment, the computer 2802 can be connected to the local network 2854 through a wired and/or wireless communication network interface or adapter 2858. The adapter 2858 can facilitate wired or wireless communication to the LAN 2854, which can also include a wireless access point (AP) disposed thereon for communicating with the adapter 2858 in a wireless mode.

When used in a WAN networking environment, the computer 2802 can include a modem 2860 or can be connected to a communications server on the WAN 2856 via other means for establishing communications over the WAN 2856, such as by way of the Internet. The modem 2860, which can be internal or external and a wired or wireless device, can be connected to the system bus 2808 via the input device interface 2844. In a networked environment, program modules depicted relative to the computer 2802 or portions thereof, can be stored in the remote memory/storage device 2852. It will be appreciated that the network connections shown are example and other means of establishing a communications link between the computers can be used.

When used in either a LAN or WAN networking environment, the computer 2802 can access cloud storage systems or other network-based storage systems in addition to, or in place of, external storage devices 2816 as described above, such as but not limited to a network virtual machine providing one or more aspects of storage or processing of information. Generally, a connection between the computer 2802 and a cloud storage system can be established over a LAN 2854 or WAN 2856 e.g., by the adapter 2858 or modem 2860, respectively. Upon connecting the computer 2802 to an associated cloud storage system, the external storage interface 2826 can, with the aid of the adapter 2858 and/or modem 2860, manage storage provided by the cloud storage system as it would other types of external storage. For instance, the external storage interface 2826 can be configured to provide access to cloud storage sources as if those sources were physically connected to the computer 2802.

The computer 2802 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further aspects of various embodiments of the subject innovation are provided in the subject matter that follows:

1. A system, comprising: a memory that stores computer-executable components; and a processor, operably coupled to the memory, that executes the computer-executable components stored in the memory, wherein the computer-executable components comprise: an input component that receives computed tomography angiogram (CTA) images of a patient's brain; and a localization component that determines, via a machine learning algorithm, a location of a large vessel occlusion (LVO) in the patient's brain based on the CTA images.

2. The system of any preceding clause, wherein the location of the LVO comprises a laterality and an occlusion site.

3. The system of any preceding clause, wherein the laterality indicates a right side or a left side of the patient's brain, and wherein the occlusion site indicates an internal carotid artery (ICA), an M1 segment of a middle cerebral artery (MCA), or an M2 segment of an MCA.

4. The system of any preceding clause, further comprising: a visualization component that generates and displays to a user a three-dimensional maximum intensity projection (MIP) reconstruction of the patient's brain based on the CTA images to facilitate visual verification of the LVO by the user.

5. The system of any preceding clause, wherein the CTA images of the patient's brain are automatically cropped and subjected to three-dimensional rigid body registration prior to being received by the input component.

6. The system of any preceding clause, wherein the machine learning algorithm comprises a 3D convolutional neural network having residual bottleneck blocks or dense blocks.

7. The system of any preceding clause, wherein the machine learning algorithm is trained on a collection of CTA images labelled by neuroradiologists, wherein a CTA image in the collection of CTA images labelled by neuroradiologists is randomly augmented to enhance training efficacy.

8. The system of any preceding clause, wherein the machine learning algorithm comprises an ensemble of separate machine learning algorithms having different architectures and different hyperparameters from each other.

9. A computer-implemented method, comprising: receiving, by a device operatively coupled to a processor, computed tomography angiogram (CTA) images of a patient's brain; and determining, by the device and via a machine learning algorithm, a location of a large vessel occlusion (LVO) in the patient's brain based on the CTA images.

10. The computer-implemented method of any preceding clause, wherein the location of the LVO comprises a laterality and an occlusion site.

11. The computer-implemented method of any preceding clause, wherein the laterality indicates a right side or a left side of the patient's brain, and wherein the occlusion site indicates an internal carotid artery (ICA), an M1 segment of a middle cerebral artery (MCA), or an M2 segment of an MCA.

12. The computer-implemented method of any preceding clause, further comprising: generating, by the device, a three-dimensional maximum intensity projection (MIP) reconstruction of the patient's brain based on the CTA images; and displaying, by the device, the three-dimensional MIP reconstruction to a user to facilitate visual verification of the LVO by the user.

13. The computer-implemented method of any preceding clause, wherein the CTA images of the patient's brain are automatically cropped and subjected to three-dimensional rigid body registration prior to the receiving.

14. The computer-implemented method of any preceding clause, wherein the machine learning algorithm comprises a 3D convolutional neural network having residual bottleneck blocks or dense blocks.

15. The computer-implemented method of any preceding clause, wherein the machine learning algorithm is trained on a collection of CTA images labelled by neuroradiologists, wherein a CTA image in the collection of CTA images labelled by neuroradiologists is randomly augmented to enhance training efficacy.

16. The computer-implemented method of any preceding clause, wherein the machine learning algorithm comprises an ensemble of separate machine learning algorithms having different architectures and different hyperparameters from each other.

17. A computer program product for facilitating automated localization of large vessel occlusions, the computer program product comprising a computer readable memory having program instructions embodied therewith, the program instructions executable by a processing component to cause the processing component to: receive computed tomography angiogram (CTA) images of a patient's brain; and determine, via a machine learning algorithm, a location of a large vessel occlusion (LVO) in the patient's brain based on the CTA images.

18. The computer program product of any preceding claim, wherein the location of the LVO comprises a laterality and an occlusion site.

19. The computer program product of any preceding claim, wherein the laterality indicates a right side or a left side of the patient's brain, and wherein the occlusion site indicates an internal carotid artery (ICA), an M1 segment of a middle cerebral artery (MCA), or an M2 segment of an MCA.

20. The computer program product of any preceding claim, wherein the program instructions are further executable to cause the processing component to: generate a three-dimensional maximum intensity projection (MIP) reconstruction of the patient's brain based on the CTA images; and display the three-dimensional MIP reconstruction to a user to facilitate visual verification of the LVO by the user.

What is claimed is:

1. A system, comprising:
a memory that stores computer-executable components; and
a processor, operably coupled to the memory, that executes the computer-executable components stored in the memory, wherein the computer-executable components comprise:
an input component that receives at least computed tomography angiogram (CTA) images of a patient's brain; and
a localization component that determines, via a machine learning algorithm, a location of a large vessel occlusion (LVO) in the patient's brain based on the at least CTA images, wherein the location of the LVO comprises a laterality, and wherein the machine learning algorithm comprises a three-dimensional convolutional neural network model that produces at least a first scalar output indicating the laterality.

2. The system of claim 1, wherein the location of the LVO further comprises an occlusion site, and wherein the three-dimensional convolutional neural network model produces a second scalar output indicating the occlusion site.

3. The system of claim 2, wherein the laterality indicates a right side or a left side of the patient's brain, and wherein the occlusion site indicates an internal carotid artery (ICA), an M1 segment of a middle cerebral artery (MCA), an M2 segment of an MCA, or a posterior cerebral artery (PCA).

4. The system of claim 1, further comprising:
a visualization component that generates and displays to a user a three-dimensional maximum intensity projection (MIP) reconstruction of the patient's brain based on the at least CTA images to facilitate visual verification of the LVO by the user.

5. The system of claim 1, wherein the at least CTA images of the patient's brain are automatically cropped and subjected to three-dimensional rigid body registration prior to being received by the input component.

6. The system of claim 1, wherein the three-dimensional convolutional neural network model has residual bottleneck blocks or dense blocks.

7. The system of claim 1, wherein the machine learning algorithm is trained on a collection of CTA images labelled by neuroradiologists, wherein a CTA image in the collection of CTA images labelled by neuroradiologists is randomly augmented to enhance training efficacy.

8. The system of claim 1, wherein the machine learning algorithm further comprises an ensemble of separate machine learning algorithms having different architectures and different hyperparameters from each other.

9. A computer-implemented method, comprising:
receiving, by a device operatively coupled to a processor, at least computed tomography angiogram (CTA) images of a patient's brain; and
determining, by the device and via a machine learning algorithm, a location of a large vessel occlusion (LVO) in the patient's brain based on the at least CTA images, wherein the location of the LVO comprises a laterality, and wherein the machine learning algorithm comprises a three-dimensional convolutional neural network model that produces at least a first scalar output indicating the laterality.

10. The computer-implemented method of claim 9, wherein the location of the LVO further comprises an occlusion site, and wherein the three-dimensional convolutional neural network model produces a second scalar output indicating the occlusion site.

11. The computer-implemented method of claim 10, wherein the laterality indicates a right side or a left side of the patient's brain, and wherein the occlusion site indicates an internal carotid artery (ICA), an M1 segment of a middle cerebral artery (MCA), an M2 segment of an MCA, or a posterior cerebral artery (PCA).

12. The computer-implemented method of claim 9, further comprising:
generating, by the device, a three-dimensional maximum intensity projection (MIP) reconstruction of the patient's brain based on the at least CTA images; and
displaying, by the device, the three-dimensional MIP reconstruction to a user to facilitate visual verification of the LVO by the user.

13. The computer-implemented method of claim 12, wherein the at least CTA images of the patient's brain are automatically cropped and subjected to three-dimensional rigid body registration prior to the receiving.

14. The computer-implemented method of claim 9, wherein the three-dimensional convolutional neural network model has residual bottleneck blocks or dense blocks.

15. The computer-implemented method of claim 9, wherein the machine learning algorithm is trained on a collection of CTA images labelled by neuroradiologists, wherein a CTA image in the collection of CTA images labelled by neuroradiologists is randomly augmented to enhance training efficacy.

16. The computer-implemented method of claim 9, wherein the machine learning algorithm further comprises an ensemble of separate machine learning algorithms having different architectures and different hyperparameters from each other.

17. A computer program product for facilitating automated localization of large vessel occlusions, the computer program product comprising a non-transitory computer readable medium having program instructions embodied therewith, the program instructions executable by a processing component to cause the processing component to:
receive at least computed tomography angiogram (CTA) images of a patient's brain; and
determine, via a machine learning algorithm, a location of a large vessel occlusion (LVO) in the patient's brain based on the at least CTA images, wherein the location of the LVO comprises a laterality, and wherein the machine learning algorithm comprises a three-dimensional convolutional neural network model that produces at least a first scalar output indicating the laterality.

18. The computer program product of claim 17, wherein the location of the LVO further comprises an occlusion site, and wherein the three-dimensional convolutional neural network model produces a second scalar output indicating the occlusion site.

19. The computer program product of claim 18, wherein the laterality indicates a right side or a left side of the patient's brain, and wherein the occlusion site indicates an internal carotid artery (ICA), an M1 segment of a middle cerebral artery (MCA), an M2 segment of an MCA, or a posterior cerebral artery (PCA).

20. The computer program product of claim 17, wherein the program instructions are further executable to cause the processing component to:
- generate a three-dimensional maximum intensity projection (MIP) reconstruction of the patient's brain based on the at least CTA images; and
- display the three-dimensional MIP reconstruction to a user to facilitate visual verification of the LVO by the user.

* * * * *